US007214511B1

(12) United States Patent
Evans et al.

(10) Patent No.: US 7,214,511 B1
(45) **Date of Patent: *May 8, 2007**

(54) HORMONE RECEPTOR COMPOSITIONS AND METHODS

(75) Inventors: Ronald M. Evans, San Diego, CA (US); Cary A. Weinberger, Silver Spring, MD (US); Stanley M. Hollenberg, San Kiego, CA (US); Estelita S. Ong, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/464,262

(22) Filed: Jun. 5, 1995
(Under 37 CFR 1.47)

Related U.S. Application Data

(60) Division of application No. 08/165,708, filed on Dec. 10, 1993, now Pat. No. 5,597,705, which is a division of application No. 07/667,602, filed on Mar. 7, 1991, now Pat. No. 5,312,732, which is a division of application No. 07/108,471, filed on Oct. 20, 1987, now Pat. No. 5,071,773, which is a continuation-in-part of application No. 06/922,585, filed on Oct. 24, 1986, now abandoned.

(51) Int. Cl.
*C12N 15/12* (2006.01)

(52) U.S. Cl. ............... 435/69.1; 435/252.3; 435/320.1; 536/23.5

(58) Field of Classification Search ............... 435/69.1, 435/25.3, 365, 326; 530/350; 536/23.5
See application file for complete search history.

(56) References Cited

OTHER PUBLICATIONS

Gorman et al 1982 (Mol. Cel. Biol. 2, 1044), 1982.*
Gorman et al 1982 (PNAS 79, 6777), 1982.*
Grusnstein et al 1979 (Meth. Enz. 68, 379), 1979.*
Woo et al 1979 (Meth. Enz. 68, 389), 1979.*
Miesfeld et al 1986 (Cell 46, 389), 1986.*
Miesfeld et al 1984 (Nature .312, 779), 1984.*
Govindan et al 1985 (NAR 13, 8293), 1985.*
Hollenberg et al. 1985 (Nature 318, 635), 1985.*
Eisen et al. Affinity Labeling of the Rat Liver Glucocorticoid Receptor with Dexamethasone 21-Mesylate. J. Biol. Chem. 256(24):12920-12925, Dec. 1981.*

* cited by examiner

*Primary Examiner*—John Ulm
(74) *Attorney, Agent, or Firm*—Foley & Lardner LLP; Stephen E. Reiter

(57) ABSTRACT

In accordance with the present invention, there are provided expression systems for the production of function glucocorticoid receptor proteins, methods for the recombinant production of glucocorticoid receptor proteins as well as sequences encoding novel members of the steroid/thyroid hormone superfamily of receptors (e.g., glucocorticoid receptor). Invention expression systems comprise host cells containing DNA encoding functional glucocorticoid receptor proteins, wherein the DNA is operably linked to control sequences compatible with host cells, thereby enabling the expression of functional receptor proteins. The invention method is carried out by culturing such recombinant host cells, and recovering the functional glucocorticoid receptor proteins produced thereby. In accordance with the present invention, there are also provided substantially pure DNA's comprised of sequences which encode members of the steroid/thyroid hormone receptor superfamily having the hormone-binding and/or transcription-activating characteristics of a glucocorticoid receptor. The invention also provides various plasmids containing receptor sequences which exemplify the DNA's of the invention. The invention further provides receptor proteins, including modified functional forms thereof, expressed from the DNA's (or mRNA's) of the invention.

16 Claims, 38 Drawing Sheets

```
TTTTTAGAAAAAAAAAATATATTTCCCTCCTGCTCCTTCTGCGTTCACAAGCTAAGTTGT
TTATCTCGGCTGCGGCGGGAACTGCGGACGGTGGCGGGCGAGCGGCTCCTCTGCCAGAGT    120

                                        10
              MetAspSerLysGluSerLeuThrProGlyArgGluGluAsnProSer
TGATATTCACTGATGGACTCCAAAGAATCATTAACTCCTGGTAGAGAAGAAAACCCCAGC

         20                             30
SerValLeuAlaGlnGluArgGlyAspValMetAspPheTyrLysThrLeuArgGlyGly
AGTGTGCTTGCTCAGGAGAGGGGAGATGTGATGGACTTCTATAAAACCCTAAGAGGAGGA    240

         40                             50
AlaThrValLysValSerAlaSerSerProSerLeuAlaValAlaSerGlnSerAspSer
GCTACTGTGAAGGTTTCTGCGTCTTCACCCTCACTGGCTGTCGCTTCTCAATCAGACTCC

         60                             70
LysGlnArgArgLeuLeuValAspPheProLysGlySerValSerAsnAlaGlnGlnPro
AAGCAGCGAAGACTTTTGGTTGATTTTCCAAAAGGCTCAGTAAGCAATGCGCAGCAGCCA    360

         80                             90
AspLeuSerLysAlaValSerLeuSerMetGlyLeuTyrMetGlyGluThrGluThrLys
GATCTGTCCAAAGCAGTTTCACTCTCAATGGGACTGTATATGGGAGAGACAGAAACAAAA

         100                            110
ValMetGlyAsnAspLeuGlyPheProGlnGlnGlyGlnIleSerLeuSerSerGlyGlu
GTGATGGGAAATGACCTGGGATTCCCACAGCAGGGCCAAATCAGCCTTTCCTCGGGGGAA    480

         120                            130
ThrAspLeuLysLeuLeuGluGluSerIleAlaAsnLeuAsnArgSerThrSerValPro
ACAGACTTAAAGCTTTTGGAAGAAAGCATTGCAAACCTCAATAGGTCGACCAGTGTTCCA

         140                            150
GluAsnProLysSerSerAlaSerThrAlaValSerAlaAlaProThrGluLysGluPhe
GAGAACCCCAAGAGTTCAGCATCCACTGCTGTGTCTGCTGCCCCCACAGAGAAGGAGTTT    600
```

FIG. 3A

```
        160                                170
ProLysThrHisSerAspValSerSerGluGlnGlnHisLeuLysGlyGlnThrGlyThr
CCAAAAACTCACTCTGATGTATCTTCAGAACAGCAACATTTGAAGGGCCAGACTGGCACC

        180                                190
AsnGlyGlyAsnValLysLeuTyrThrThrAspGlnSerThrPheAspIleLeuGlnAsp
AACGGTGGCAATGTGAAATTGTATACCACAGACCAAAGCACCTTTGACATTTTGCAGGAT      720

        200                                210
LeuGluPheSerSerGlySerProGlyLysGluThrAsnGluSerProTrpArgSerAsp
TTGGAGTTTTCTTCTGGGTCCCCAGGTAAAGAGACGAATGAGAGTCCTTGGAGATCAGAC

        220                                230
LeuLeuIleAspGluAsnCysLeuLeuSerProLeuAlaGlyGluAspAspSerPheLeu
CTGTTGATAGATGAAAACTGTTTGCTTTCTCCTCTGGCGGGAGAAGACGATTCATTCCTT      840

        240                                250
LeuGluGlyAsnSerAsnGluAspCysLysProLeuIleLeuProAspThrLysProLys
TTGGAAGGAAACTCGAATGAGGACTGCAAGCCTCTCATTTTACCGGACACTAAACCCAAA

        260                                270
IleLysAspAsnGlyAspLeuValLeuSerSerProSerAsnValThrLeuProGlnVal
ATTAAGGATAATGGAGATCTGGTTTTGTCAAGCCCCAGTAATGTAACACTGCCCCAAGTG      960

        280                                290
LysThrGluLysGluAspPheIleGluLeuCysThrProGlyValIleLysGlnGluLys
AAAACAGAAAAAGAAGATTTCATCGAACTCTGCACCCCTGGGGTAATTAAGCAAGAGAAA
```

FIG. 3B

```
         300                                310
LeuGlyThrValTyrCysGlnAlaSerPheProGlyAlaAsnIleIleGlyAsnLysMet
CTGGGCACAGTTTACTGTCAGGCAAGCTTTCCTGGAGCAAATATAATTGGTAATAAAATG     1080

         320                                330
SerAlaIleSerValHisGlyValSerThrSerGlyGlyGlnMetTyrHisTyrAspMet
TCTGCCATTTCTGTTCATGGTGTGAGTACCTCTGGAGGACAGATGTACCACTATGACATG

         340                                350
AsnThrAlaSerLeuSerGlnGlnGlnAspGlnLysProIlePheAsnValIleProPro
AATACAGCATCCCTTTCTCAACAGCAGGATCAGAAGCCTATTTTTAATGTCATTCCACCA     1200

         360                                370
IleProValGlySerGluAsnTrpAsnArgCysGlnGlySerGlyAspAspAsnLeuThr
ATTCCCGTTGGTTCCGAAAATTGGAATAGGTGCCAAGGATCTGGAGATGACAACTTGACT

         380                                390
SerLeuGlyThrLeuAsnPheProGlyArgThrValPheSerAsnGlyTyrSerSerPro
TCTCTGGGGACTCTGAACTTCCCTGGTCGAACAGTTTTTTCTAATGGCTATTCAAGCCCC     1320

         400                                410
SerMetArgProAspValSerSerProProSerSerSerSerThrAlaThrThrGlyPro
AGCATGAGACCAGATGTAAGCTCTCCTCCATCCAGCTCCTCAACAGCAACAACAGGACCA

         420                                430
ProProLysLeuCysLeuValCysSerAspGluAlaSerGlyCysHisTyrGlyValLeu
CCTCCCAAACTCTGCCTGGTGTGCTCTGATGAAGCTTCAGGATGTCATTATGGAGTCTTA     1440

         440                                450
ThrCysGlySerCysLysValPhePheLysArgAlaValGluGlyGlnHisAsnTyrLeu
ACTTGTGGAAGCTGTAAAGTTTTCTTCAAAAGAGCAGTGGAAGGACAGCACAATTACCTA

         460                                470
CysAlaGlyArgAsnAspCysIleIleAspLysIleArgArgLysAsnCysProAlaCys
TGTGCTGGAAGGAATGATTGCATCATCGATAAAATTCGAAGAAAAAACTGCCCAGCATGC     1560
```

FIG. 3C

```
          480                                     490
ArgTyrArgLysCysLeuGlnAlaGlyMetAsnLeuGluAlaArgLysThrLysLysLys
CGCTATCGAAAATGTCTTCAGGCTGGAATGAACCTGGAAGCTCGAAAAACAAAGAAAAAA

          500                                     510
IleLysGlyIleGlnGlnAlaThrThrGlyValSerGlnGluThrSerGluAsnProGly
ATAAAAGGAATTCAGCAGGCCACTACAGGAGTCTCACAAGAAACCTCTGAAAATCCTGGT    1680

          520                                     530
AsnLysThrIleValProAlaThrLeuProGlnLeuThrProThrLeuValSerLeuLeu
AACAAAACAATAGTTCCTGCAACGTTACCACAACTCACCCCTACCCTGGTGTCACTGTTG

          540                                     550
GluValIleGluProGluValLeuTyrAlaGlyTyrAspSerSerValProAspSerThr
GAGGTTATTGAACCTGAAGTGTTATATGCAGGATATGATAGCTCTGTTCCAGACTCAACT    1800

          560                                     570
TrpArgIleMetThrThrLeuAsnMetLeuGlyGlyArgGlnValIleAlaAlaValLys
TGGAGGATCATGACTACGCTCAACATGTTAGGAGGGCGGCAAGTGATTGCAGCAGTGAAA

          580                                     590
TrpAlaLysAlaIleProGlyPheArgAsnLeuHisLeuAspAspGlnMetThrLeuLeu
TGGGCAAAGGCAATACCAGGTTTCAGGAACTTACACCTGGATGACCAAATGACCCTACTG    1920
```

FIG. 3D

```
          600                                     610
GlnTyrSerTrpMetPheLeuMetAlaPheAlaLeuGlyTrpArgSerTyrArgGlnSer
CAGTACTCCTGGATGTTTCTTATGGCATTTGCTCTGGGGTGGAGATCATATAGACAATCA

          620                                     630
SerAlaAsnLeuLeuCysPheAlaProAspLeuIleIleAsnGluGlnArgMetThrLeu
AGTGCAAACCTGCTGTGTTTTGCTCCTGATCTGATTATTAATGAGCAGAGAATGACTCTA     2040

          640                                     650
ProCysMetTyrAspGlnCysLysHisMetLeuTyrValSerSerGluLeuHisArgLeu
CCCTGCATGTACGACCAATGTAAACACATGCTGTATGTTTCCTCTGAGTTACACAGGCTT

          660                                     670
GlnValSerTyrGluGluTyrLeuCysMetLysThrLeuLeuLeuLeuSerSerValPro
CAGGTATCTTATGAAGAGTATCTCTGTATGAAAACCTTACTGCTTCTCTCTTCAGTTCCT     2160

          680                                     690
LysAspGlyLeuLysSerGlnGluLeuPheAspGluIleArgMetThrTyrIleLysGlu
AAGGACGGTCTGAAGAGCCAAGAGCTATTTGATGAAATTAGAATGACCTACATCAAAGAG

          700                                     710
LeuGlyLysAlaIleValLysArgGluGlyAsnSerSerGlnAsnTrpGlnArgPheTyr
CTAGGAAAAGCCATTGTCAAGAGGGAAGGAAACTCCAGCCAGAACTGGCAGCGGTTTTAT     2280

          720                                     730
GlnLeuThrLysLeuLeuAspSerMetHisGluValValGluAsnLeuLeuAsnTyrCys
CAACTGACAAAACTCTTGGATTCTATGCATGAAGTGGTTGAAAATCTCCTTAACTATTGC

          740                                     750
PheGlnThrPheLeuAspLysThrMetSerIleGluPheProGluMetLeuAlaGluIle
TTCCAAACATTTTTGGATAAGACCATGAGTATTGAATTCCCCGAGATGTTAGCTGAAATC     2400

          760                                     770
IleThrAsnGlnIleProLysTyrSerAsnGlyAsnIleLysLysLeuLeuPheHisGln
ATCACCAATCAGATACCAAAATATTCAAATGGAAATATCAAAAAACTTCTGTTTCATCAA
```

FIG. 3E

```
LysSTOP
AAGTGACTGCCTTAATAAGAATGGTTGCCTTAAAGAAAGTCGAATTAATAGCTTTTATTG    2520
TATAAACTATCAGTTTGTCCTGTAGAGGTTTTGTTGTTTTATTTTTTATTGTTTTCATCT
GTTGTTTTGTTTTAAATACGCACTACATGTGGTTTATAGAGGGCCAAGACTTGGCAACAG    2640
AAGCAGTTGAGTCGTCATCACTTTTCAGTGATGGGAGAGTAGATGGTGAAATTTATTAGT
TAATATATCCCAGAAATTAGAAACCTTAATATGTGGACGTAATCTCCACAGTCAAAGAAG
GATGGCACCTAAACCACCAGTGCCCAAAGTCTGTGTGATGAACTTTCTCTTCATACTTTT
TTTCACAGTTGGCTGGATGAAATTTTCTAGACTTTCTGTTGGTGTATCCCCCCCTGTAT    2880
AGTTAGGATAGCATTTTTGATTTATGCATGGAAACCTGAAAAAAAGTTTACAAGTGTATA
TCAGAAAAGGGAAGTTGTGCCTTTTATAGCTATTACTGTCTGGTTTTAACAATTTCCTTT
ATATTTAGTGAACTACGCTTGCTCATTTTTTCTTACATAATTTTTTATTCAAGTTATTGT
ACAGCTGTTTAAGATGGGCAGCTAGTTCGTAGCTTTCCCAAATAAACTCTAAACATTAAT    3120
CAATCATCTGTGTGAAAATGGGTTGGTGCTTCTAACCTGATGGCACTTAGCTATCAGAAG
ACCACAAAAATTGACTCAAATCTCCAGTATTCTTGTCAAAAAAAAAAAAAAAAAAAGCTCA
TATTTTGTATATATCTGCTTCAGTGGAGAATTATATAGGTTGTGCAAATTAACAGTCCTA
```

FIG. 3F

```
ACTGGTATAGAGCACCTAGTCCAGTGACCTGCTGGGTAAACTGTGGATGATGGTTGCAAA    3360
AGACTAATTTAAAAAATAACTACCAAGAGGCCCTGTCTGTACCTAACGCCCTATTTTTGC
AATGGCTATATGGCAAGAAAGCTGGTAAACTATTTGTCTTTCAGGACCTTTTGAAGTAGT
TTGTATAACTTCTTAAAAGTTGTGATTCCAGATAACCAGCTGTAACACAGCTGAGAGACT
TTTAATCAGACAAAGTAATTCCTCTCACTAAACTTTACCCAAAAACTAAATCTCTAATAT    3600
GGCAAAAATGGCTAGACACCCATTTTCACATTCCCATCTGTCACCAATTGGTTAATCTTT
CCTGATGGTACAGGAAAGCTCAGCTACTGATTTTTGTGATTTAGAACTGTATGTCAGACA
TCCATGTTTGTAAAACTACACATCCCTAATGTGTGCCATAGAGTTTAACACAAGTCCTGT
GAATTTCTTCACTGTTGAAAATTATTTAAACAAAATAGAAGCTGTAGTAGCCCTTTCTG    3840
TGTGCACCTTACCAACTTTCTGTAAACTCAAAACTTAACATATTTACTAAGCCACAAGAA
ATTTGATTTCTATTCAAGGTGGCCAAATTATTTGTGTAATAGAAAACTGAAAATCTAATA
TTAAAAATATGGAACTTCTAATATATTTTTATATTTAGTTATAGTTTCAGATATATATCA
TATTGGTATTCACTAATCTGGGAAGGGAAGGGCTACTGCAGCTTTACATGCAATTTATTA    4080
```

FIG. 3G

```
AAATGATTGTAAAATAGCTTGTATAGTGTAAAATAAGAATGATTTTTAGATGAGATTGTT
TTATCATGACATGTTATATATTTTTTGTAGGGGTCAAAGAAATGCTGATGGATAACCTAT
ATGATTTATAGTTTGTACATGCATTCATACAGGCAGCGATGGTCTCAGAAACCAAACAGT
TTGCTCTAGGGGAAGAGGGAGATGGAGACTGGTCCTGTGTGCAGTGAAGGTTGCTGAGGC    4320
TCTGACCCAGTGAGATTACAGAGGAAGTTATCCTCTGCCTCCCATTCTGACCACCCTTCT
CATTCCAACAGTGAGTCTGTCAGCGCAGGTTTAGTTTACTCAATCTCCCCTTGCACTAAA
GTATGTAAAGTATGTAAACAGGAGACAGGAAGGTGGTGCTTACATCCTTAAAGGCACCAT
CTAATAGCGGGTTACTTTCACATACAGCCCTCCCCCAGCAGTTGAATGACAACAGAAGCT    4560
TCAGAAGTTTGGCAATAGTTTGCATAGAGGTACCAGCAATATGTAAATAGTGCAGAATCT
CATAGGTTGCCAATAATACACTAATTCCTTTCTATCCTACAACAAGAGTTTATTTCCAAA
TAAAATGAGGACATGTTTTTGTTTTCTTTGAATGCTTTTTGAATGTTATTTGTTATTTTC
AGTATTTTGGAGAAATTATTTAATAAAAAACAATCATTTGCTTTTTGAAAAAAAAAAA    4800
```

```
     720
---GlnLeuThrLysLeuLeuAspSerMetHisGlu
---GGTCTGACAAAACTCTTGGATTCTATGCATGAA

α
     730                                 740
     ValValGluAsnLeuLeuAsnTyrCysPheGlnThrPheLeuAspLysThrMetSerIle
     GTGGTTGAAAATCTCCTTAACTATTGCTTCCAAACATTTTTGGATAAGACCATGAGTATT  2373

     750                                 760
     GluPheProGluMetLeuAlaGluIleIleThrAsnGlnIleProLysTyrSerAsnGly
     GAATTCCCCGAGATGTTAGCTGAAATCATCACCAATCAGATACCAAAATATTCAAATGGA  2433

     770
     AsnIleLysLysLeuLeuPheHisGlnLysSTOP
     AATATCAAAAAACTTCTGTTTCATCAAAAGTGA....

β
     730                                 740
     AsnValMetTrpLeuLysProGluSerThrSerHisThrLeuIleSTOP
     AATGTTATGTGGTTAAAACCAGAAAGCACATCTCACACATTAATCTGATTTTCATCCCAA  2373

     CAATCTTGGCGCTCAAAAAATAGAACTCAATGAGAAAAAGAAGATTATGTGCACTTCGTT  2433
GTCAATAATAAGTCAACTGATGCTCATCGACAACTATAGGAGGCTTTTCATTAAATGGGAAAAAGAAGCTGTGCCCTTTTAGGATACGTGGGGGAAAAGAA
AGTCATCTTAATTATGTTTAATTGTGGATTTAAGTGCTATATGGTGGTGCTGTTTGAAAGCAGATTTATTTCCTATGTATGTGTTATCTGGCCATCCCAA  2633
CCCAAACTGTTGAAGTTTGTAGTAACTTCAGTGAGAGTTGGTTACTCACAACAAATCCTGAAAAGTATTTTTAGTGTTTGTAGGTATTCTGTGGGATACT
ATACAAGCAGAACTGAGGCACTTAGGACATAACACTTTTGGGGTATATATATCCAAATGCCTAAAACTATGGGAGGAAACCTTGGCCACCCCAAAAGGAA  2833
AACTAACATGATTTGTGTCTATGAAGTGCTGGATAATTAGCATGGGATGAGCTCTGGGCATGCCATGAAGGAAAGCCACGCTCCCTTCAGAATTCAGAGG
CAGGGAGCAATTCCAGTTTCACCTAAGTCTCATAATTTTAGTTCCCTTTTAAAAACCCTGAAAACTACATCACCATGGAATGAAAAATATTGTTATACAA  3033
TACATTGATCTGTCAAACTTCCAGAACCATGGTAGCCTTCAGTGAGATTTCCATCTTGGCTGGTCACTCCCTGACTGTAGCTGTAGGTGAATGTGTTTTT
GTGTGTGTGTGTCTGGTTTTAGTGTCAGAAGGGAAATAAAAGTGTAAGGAGGACACTTTAAACCCTTTGGGTGGAGTTTCGTAATTTCCCAGACTATTTT  3233
CAAGCAACCTGGTCCACCCAGGATTAGTGACCAGGTTTTCAGGAAAGGATTTGCTTCTCTCTAGAAAATGTCTGAAAGGATTTTATTTTCTGATGAAAGG
CTGTATGAAAATACCCTCCTCAAATAACTTGCTTAACTACATATAGATTCAAGTGTGTCAATATTCTATTTTGTATATTAAATGCTATATAATGGGGACA  3433
AATCTATATTATACTGTGTATGGCATTATTAAGAAGCTTTTTCATTATTTTTTATCACAGTAATTTTAAAATGTGTAAAAATTAAAACCAGTGACTCCTG
TTTAAAAATAAAAGTTGTAGTTTTTTATTCATGCTGAATAATAATCTGTAGTTAAAAAAAAAGTGTCTTTTTACCTACGCAGTGAAATGTCAGACTGTAA  3633
AACCTTGTGTGGAAATGTTTAACTTTTATTTTTTCATTTAAATTTGCTGTTCTGGTATTACCAAACCACACATTTGTACCGAATTGGCAGTAAATGTTAG
CCATTTACAGCAATGCCAAATATGGAGAAACATCATAATAAAAAAATCTGCTTTTTTCAAAAAAAAAAAAAAAAAAAAAAAAAAAA  3820
```

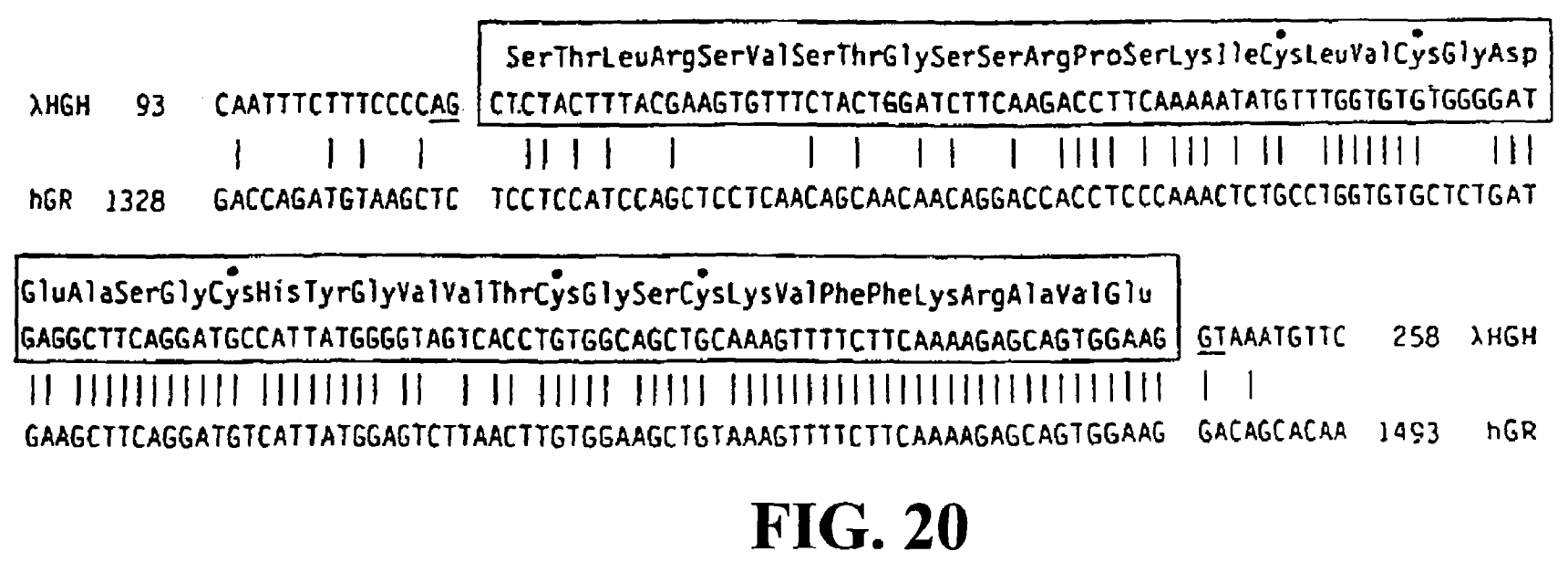

```
                           SerThrLeuArgSerValSerThrGlySerSerArgProSerLysIleCysLeuValCysGlyAsp
λHGH   93   CAATTTCTTTCCCCAG CTCTACTTTACGAAGTGTTTCTACTGGATCTTCAAGACCTTCAAAAATATGTTTGGTGTGTGGGGAT

hGR  1328   GACCAGATGTAAGCTC TCCTCCATCCAGCTCCTCAACAGCAACAACAGGACCACCTCCCAAACTCTGCCTGGTGTGCTCTGAT

GluAlaSerGlyCysHisTyrGlyValValThrCysGlySerCysLysValPhePheLysArgAlaValGlu
GAGGCTTCAGGATGCCATTATGGGGTAGTCACCTGTGGCAGCTGCAAAGTTTTCTTCAAAAGAGCAGTGGAAG GTAAATGTTC   258 λHGH

GAAGCTTCAGGATGTCATTATGGAGTCTTAACTTGTGGAAGCTGTAAAGTTTTCTTCAAAAGAGCAGTGGAAG GACAGCACAA  1493  hGR
```

FIG. 20

```
  1 GAATTCCGCGGGAGCCAACTTCAGGCTGCTCAGAGGAAGCCCGTGCAGTCAGTCACCTGGGTGCAAGAGCGTTGC
    TGCCTCGGGCTCTCCCGCTGCAGGGAGAGCGGCACTCGCTGGCCTGGATGTGGTTGGATTTAGGGGGGCTCCGCA

                                                                            Met
151 GCAGGGGTTTCGTGGCGGTGGCAAGCGCTGCAACAGGTAGACGGCGAGAGACGGACCCCGGCCGAGGCAGGGATG
                             10                          20
    GluThrLysGlyTyrHisSerLeuProGluGlyLeuAspMetGluArgArgTrpGlyGlnValSerGlnAlaVal
    GAGACCAAAGGCTACCACAGTCTCCCTGAAGGTCTAGATATGGAAAGACGGTGGGGTCAAGTTTCTCAGGCTGTG
             30                          40                                 50
    GluArgSerSerLeuGlyProThrGluArgThrAspGluAsnAsnTyrMetGluIleValAsnValSerCysVal
301 GAGCGTTCTTCCCTGGGACCTACAGAGAGGACCGATGAGAATAACTACATGGAGATTGTCAACGTAAGCTGTGTT
                             60                          70
    SerGlyAlaIleProAsnAsnSerThrGlnGlySerSerLysGluLysGlnGluLeuLeuProCysLeuGlnGln
    TCCGGTGCTATTCCAAACAACAGTACTCAAGGAAGCAGCAAAGAAAAACAAGAACTACTCCCTTGCCTTCAGCAA
             80                          90                                100
    AspAsnAsnArgProGlyIleLeuThrSerAspIleLysThrGluLeuGluSerLysGluLeuSerAlaThrVal
451 GACAATAATCGGCCTGGGATTTTAACATCTGATATTAAAACTGAGCTGGAATCTAAGGAACTTTCAGCAACTGTA
                            110                         120
    AlaGluSerMetGlyLeuTyrMetAspSerValArgAspAlaAspTyrSerTyrGluGlnGlnAsnGlnGlnGly
    GCTGAGTCCATGGGTTTATATATGGATTCTGTAAGAGATGCTGACTATTCCTATGAGCAGCAGAACCAACAAGGA
            130                         140                                150
    SerMetSerProAlaLysIleTyrGlnAsnValGluGlnLeuValLysPheTyrLysGlyAsnGlyHisArgPro
601 AGCATGAGTCCAGCTAAGATTTATCAGAATGTTGAACAGCTGGTGAAATTTTACAAAGGAAATGGCCATCGTCCT
                            160                         170
    SerThrLeuSerCysValAsnThrProLeuArgSerPheMetSerAspSerGlySerSerValAsnGlyGlyVal
    TCCACTCTAAGTTGTGTGAACACGCCCTTGAGATCATTTATGTCTGACTCTGGGAGCTCCGTGAATGGTGGCGTC
            180                         190                                200
    MetArgAlaIleValLysSerProIleMetCysHisGluLysSerProSerValCysSerProLeuAsnMetThr
751 ATGCGCGCCATTGTTAAAAGCCCTATCATGTGTCATGAGAAAAGCCCGTCTGTTTGCAGCCCTCTGAACATGACA
                            210                         220
    SerSerValCysSerProAlaGlyIleAsnSerValSerSerThrThrAlaSerPheGlySerPheProValHis
    TCTTCGGTTTGCAGCCCTGCTGGAATCAACTCTGTGTCCTCCACCACAGCCAGCTTTGGCAGTTTTCCAGTGCAC
            230                         240                                250
    SerProIleThrGlnGlyThrProLeuThrCysSerProAsnAlaGluAsnArgGlySerArgSerHisSerPro
901 AGCCCAATCACCCAGGGAACTCCTCTGACATGCTCCCCTAATGCTGAAAATCGAGGCTCCAGGTCGCACAGCCCT
                            260                         270
```

Fig. 22A

```
      AlaHisAlaSerAsnValGlySerProLeuSerSerProLeuSerSerMetLysSerSerIleSerSerProPro
      GCACATGCTAGCAATGTGGGCTCTCCTCTCTCAAGTCCGTTAAGTAGCATGAAATCCTCAATTTCCAGCCCTCCA
              280                           290                           300
      SerHisCysSerValLysSerProValSerSerProAsnAsnValThrLeuArgSerSerValSerSerProAla
1051  AGTCACTGCAGTGTAAAATCTCCAGTCTCCAGTCCCAATAATGTCACTCTGAGATCCTCTGTGTCTAGCCCTGCA
                            310                           320
      AsnIleAsnAsnSerArgCysSerValSerSerProSerAsnThrAsnAsnArgSerThrLeuSerSerProAla
      AATATTAACAACTCAAGGTGCTCTGTTTCCAGCCCTTCGAACACTAATAACAGATCCACGCTTTCCAGTCCGGCA
              330                           340                           350
      AlaSerThrValGlySerIleCysSerProValAsnAsnAlaPheSerTyrThrAlaSerGlyThrSerAlaGly
1201  GCCAGTACTGTGGGATCTATCTGTAGCCCTGTAAACAATGCCTTCAGCTACACTGCTTCTGGCACCTCTGCTGGA
                            360                           370
      SerSerThrLeuArgAspValValProSerProAspThrGlnGluLysGlyAlaGlnGluValProPheProLys
      TCCAGTACATTGCGGGATGTGGTTCCCAGTCCAGACACGCAGGAGAAAGGTGCTCAAGAGGTCCCTTTTCCTAAG
              380                           390                           400
      ThrGluGluValGluSerAlaIleSerAsnGlyValThrGlyGlnLeuAsnIleValGlnTyrIleLysProGlu
1351  ACTGAGGAAGTAGAGAGTGCCATCTCAAATGGTGTGACTGGCCAGCTTAATATTGTCCAGTACATAAAACCAGAA
                            410                           420
      ProAspGlyAlaPheSerSerSerCysLeuGlyGlyAsnSerLysIleAsnSerAspSerSerPheSerValPro
      CCAGATGGAGCTTTTAGCAGCTCATGTCTAGGAGGAAATAGCAAAATAAATTCGGATTCTTCATTCTCAGTACCA
              430                           440                           450
      IleLysGlnGluSerThrLysHisSerCysSerGlyThrSerPheLysGlyAsnProThrValAsnProPhePro
1501  ATAAAGCAAGAATCAACCAAGCATTCATGTTCAGGCACCTCTTTTAAAGGGAATCCAACAGTAAACCCGTTTCCA
                            460                           470
      PheMetAspGlySerTyrPheSerPheMetAspAspLysAspTyrTyrSerLeuSerGlyIleLeuGlyProPro
      TTTATGGATGGCTCGTATTTTTCCTTTATGGATGATAAAGACTATTATTCCCTATCAGGAATTTTAGGACCACCT
```

FIG. 22B

```
                 480                                     490                                     500
     ValProGlyPheAspGlyAsnCysGluGlySerGlyPheProValGlyIleLysGlnGluProAspAspGlySer
1651 GTGCCCGGCTTTGATGGTAACTGTGAAGGCAGCGGATTCCCAGTGGGTATTAAACAAGAACCAGATGACGGGAGC
                                         510                                     520
     TyrTyrProGluAlaSerIleProSerSerAlaIleValGlyValAsnSerGlyGlyGlnSerPheHisTyrArg
     TATTACCCAGAGGCCAGCATCCCTTCCTCTGCTATTGTTGGGGTGAATTCAGGTGGACAGTCCTTCCACTACAGG
                 530                                     540                                     550
     IleGlyAlaGlnGlyThrIleSerLeuSerArgSerAlaArgAspGlnSerPheGlnHisLeuSerSerPhePro
1801 ATTGGTGCTCAAGGTACAATATCTTTATCACGATCGGCTAGAGACCAATCTTTCCAACACCTGAGTTCCTTTCCT
                                         560                                     570
     ProValAsnThrLeuValGluSerTrpLysSerHisGlyAspLeuSerSerArgArgSerAspGlyTyrProVal
     CCTGTCAATACTTTAGTGGAGTCATGGAAATCACACGGCGACCTGTCGTCTAGAAGAAGTGATGGGTATCCGGTC
                 580                                     590                                     600
     LeuGluTyrIleProGluAsnValSerSerSerThrLeuArgSerValSerThrGlySerSerArgProSerLys
1951 TTAGAATACATTCCAGAAAATGTATCAAGCTCTACTTTACGAAGTGTTTCTACTGGATCTTCAAGACCTTCAAAA
                                         610                                     620
     IleCysLeuValCysGlyAspGluAlaSerGlyCysHisTyrGlyValValThrCysGlySerCysLysValPhe
     ATATGTTTGGTGTGTGGGGATGAGGCTTCAGGATGCCATTATGGGGTAGTCACCTGTGGCAGCTGCAAAGTTTTC
                 630                                     640                                     650
     PheLysArgAlaValGluGlyGlnHisAsnTyrLeuCysAlaGlyArgAsnAspCysIleIleAspLysIleArg
2101 TTCAAAAGAGCAGTGGAAGGGCAACACAACTATTTATGTGCTGGAAGAAATGATTGCATCATTGATAAGATTCGA
                                         660                                     670
     ArgLysAsnCysProAlaCysArgLeuGlnLysCysLeuGlnAlaGlyMetAsnLeuGlyAlaArgLysSerLys
     CGAAAGAATTGTCCTGCTTGCAGACTTCAGAAATGTCTTCAAGCTGGAATGAATTTAGGAGCACGAAAGTCAAAG
                 680                                     690                                     700
     LysLeuGlyLysLeuLysGlyIleHisGluGluGlnProGlnGlnGlnGlnProProProProProProProPro
2251 AAGTTGGGAAAGTTAAAAGGGATTCACGAGGAGCAGCCACAGCAGCAGCAGCCCCCACCCCCACCCCCACCCCCG
                                         710                                     720
     GlnSerProGluGluGlyThrThrTyrIleAlaProAlaLysGluProSerValAsnThrAlaLeuValProGln
     CAAAGCCCAGAGGAAGGGACAACGTACATCGCTCCTGCAAAAGAACCCTCGGTCAACACAGCACTGGTTCCTCAG
                 730                                     740                                     750
     LeuSerThrIleSerArgAlaLeuThrProSerProValMetValLeuGluAsnIleGluProGluIleValTyr
2401 CTCTCCACAATCTCACGAGCGCTCACACCTTCCCCCGTTATGGTCCTTGAAAACATTGAACCTGAAATTGTATAT
                                         760                                     770
```

FIG. 22C

```
      AlaGlyTyrAspSerSerLysProAspThrAlaGluAsnLeuLeuSerThrLeuAsnArgLeuAlaGlyLysGln
      GCAGGCTATGACAGCTCAAAACCAGATACAGCCGAAAATCTGCTCTCCACGCTCAACCGCTTAGCAGGCAAACAG
                 780                                     790                                     800
      MetIleGlnValValLysTrpAlaLysValLeuProGlyPheLysAsnLeuProLeuGluAspGlnIleThrLeu
2551  ATGATCCAAGTCGTGAAGTGGGCAAAGGTACTTCCAGGATTTAAAAACTTGCCTCTTGAGGACCAAATTACCCTA
                               810                                     820
      IleGlnTyrSerTrpMetCysLeuSerSerPheAlaLeuSerTrpArgSerTyrLysHisThrAsnSerGlnPhe
      ATCCAGTATTCTTGGATGTGTCTATCATCATTTGCCTTGAGCTGGAGATCGTACAAACATACGAACAGCCAATTT
                 830                                     840                                     850
      LeuTyrPheAlaProAspLeuValPheAsnGluGluLysMetHisGlnSerAlaMetTyrGluLeuCysGlnGly
2701  CTCTATTTTGCACCAGACCTAGTCTTTAATGAAGAGAAGATGCATCAGTCTGCCATGTATGAACTATGCCAGGGG
                               860                                     870
      MetHisGlnIleSerLeuGlnPheValArgLeuGlnLeuThrPheGluGluTyrThrIleMetLysValLeuLeu
      ATGCACCAAATCAGCCTTCAGTTCGTTCGACTGCAGCTCACCTTTGAAGAATACACCATCATGAAAGTTTTGCTG
                 880                                     890                                     900
      LeuLeuSerThrIleProLysAspGlyLeuLysSerGlnAlaAlaPheGluGluMetArgThrAsnTyrIleLys
2851  CTACTAAGCACAATTCCAAAGGATGGCCTCAAAAGCCAGGCTGCATTTGAAGAAATGAGGACAAATTACATCAAA
                               910                                     920
      GluLeuArgLysMetValThrLysCysProAsnAsnSerGlyGlnSerTrpGlnArgPheTyrGlnLeuThrLys
      GAACTGAGGAAGATGGTAACTAAGTGTCCCAACAATTCTGGGCAGAGCTGGCAGAGGTTCTACCAACTGACCAAG
                 930                                     940                                     950
      LeuLeuAspSerMetHisAspLeuValSerAspLeuLeuGluPheCysPheTyrThrPheArgGluSerHisAla
3001  CTGCTGGACTCCATGCATGACCTGGTGAGCGACCTGCTGGAATTCTGCTTCTACACCTTCCGAGAGTCCCATGCG
                               960                                     970
      LeuLysValGluPheProAlaMetLeuValGluIleIleSerAspGlnLeuProLysValGluSerGlyAsnAla
      CTGAAGGTAGAGTTCCCCGCAATGCTGGTGGAGATCATCAGCGACCAGCTGCCCAAGGTGGAGTCGGGGAACGCC
                 980      984
      LysProLeuTyrPheHisArgLysEnd
3151  AAGCCGCTCTACTTCCACCGGAAGTGACTGCCCGCTGCCCAGAAGAACTTTGCCTTAAGTTTCCCTGTGTTGTTC
      CACACCCAGAAGGACCCAAGAAAACCTGTTTTTAACATGTGATGGTTGATTCACACTTGTTCAACAGTTTCTCAA
```

FIG. 22D

```
3301 GTTTAAAGTCATGTCAGAGGTTTGGAGCCGGGAAAGCTGTTTTTCCGTGGATTTGGCGAGACCAGAGCAGTCTGA
     AGGATTCCCCACCTCCAATCCCCCAGCGCTTAGAAACATGTTCCTGTTCCTCGGGATGAAAAGCCATATCTAGTC
3451 AATAACTCTGATTTTGATATTTTCACAGATGGAAGAAGTTTTAACTATGCCGTGTAGTTTCTGGTATCGTTCGCT
     TGTTTTAAAAGGGTTCAAGGACTAACGAACGTTTTAAAGCTTACCCTTGGTTTGCACATAAAACGTATAGTCAAT
3601 ATGGGGCATTAATATTCTTTTGTTATTAAAAAAACACAAAAAAATAATAAAAAAATATATACAGATTCCTGTTGT
     GTAATAACAGAACTCGTGGCGTGGGGCAGCAGCTGCCTCTGAGCCCTCGCTCGTCCACGGTCTTCTGCATCACTG
3751 GTATACACACTCGTTAGCGTCCATTTCTTATTTAATTAGAATGGATAAGATGATGTTAAATGCCTTGGTTTGATT
     TCTAGTATCTATTGTGTTGGCTTTACAAATAATTTTTTGCAGTCTTTTGCTGTGCTGTACATTACTGTATGTATA
3901 AATTATGAAGGACCTGAAATAAGGTATAAGGATCTTTTGTAAATGAGACACATACAAAAAAAATCTTTAATGGTT
     AATAGGATGAATGGGAAAGTATTTTTGAAAGAATTCTATTTTGCTGGAGACTATTTAAGTACTATCTTTGTCTAA
4051 ACAAGGTAATTTTTTTTTGTAAAGTGCAATGTCCTGCATGCATAATGAACCGTTTACAGTGTATTTAAGAAAGGG
     AAAGCTGTGCCTTTTTTAGCTTCATATCTAATTTACCATTATTTTACAGTCTCTGTTGTAAATAACCACACTGAA
4201 ACCTCTTCGGTTGTCTTGAAACCTTTCTACTTTTTCTGTACTTTTTGTTTTGTTCTTGGTCTCCCGCTTGGGGCA
     TTTGTGGGACTCCAGCACGTTTTCTGGCTTCTGCTTCATCCTGCTCCATCGGGGAATGACACACTGCGGTGTCTG
4351 CAGCTCCTGGAAGGTGTCATTTGACAACACATGTGGGAGAGGAGGTCCTTGGAGTGCTGCAGCTTTGGGAAAGCC
     TGCCTCGTTTCCCTTTTCCTCTAGAAGCAGAACCAGCTCTACGAGAGTGAGACTGGGAACTTGATGGCTCAGAGA
4501 GCATCTTTTCCTCCCATTTTAGAAAATCAGATTTTCTCCTGTGGGAAAAAAAAATTCCATGCACTCTCTCTCTGT
     TAAAGATCAGCTATTCCCTTCTGATCTTGGAAAGAGGTTCTGCACTCCTGGAACCGGTCACAGGAACGCACAGAT
4651 CATGGCAGGATGCGCTGGGACGGCCCATCTTGGCAAGGTTCAGTCTGAATGGCATGGAGACCGGGAGATAGAGGG
     GTTTTAGATTTTTAAAAGGTAGGTTTTAAAAATAAGTTTTATACATAAACAGTTTTGGAGAAAAATTACAGATCA
4801 TATAAGCAAGACAGTGGCACTAAAATGTTTAATTCATTAATCTGTTTGTTTGGCACTGATGCAATGTATGGCTTT
     TCTCTTGCCCCAAATCACAAACATATGTATCTTTGGGGAAACTAACAATATGATTGCACTAAATAAACTACTTTG
4951 AATAGAGGCCAAATTAATCTTTTAAAAATGATGATAATCATCAGGTTTACTCAGTGAAATCATATTAATTATTTT
     CCAAAATCTAAAAGCTGTAGCTGGAGAAGCCCATGGCCACGAGGAAGCAGCAATTAATTAGATCAACACTTTTCT
5101 CCAGGGTTCACCATGCAGGCAACATTACCTTGTCTTTCAAAAGACACCTGCCTTAGTGCAAGGGGAAACCTGTGA
     AAGCTGCACTCAGAGGGAGGAGTCTTTCTTACATAATTTGCAATTTCAGGAATTTAATTTATAGGCAGATCTTTA
5251 AATACAGTCAACTTACGGTGCACAGTAATATGAAAGCCACACTTTGAAGGTAATAAATACACAGCATGCAGACTG
     GGAGTTGCTAGCAAACAAATGGCTTACTTACAAAAGCAGCTTTTAGTTCAGACTTAGTTTTTATAAAATGAGAAT
5401 TCTGACTTACTTAACCAGGTTTGGGATGGAGATGGTCTGCATCAGCTTTTTGTATTAACAAAGTTACTGGCTCTT
     TGTGTGTCTCCAGGTAACTTTGCTTGATTAAACAGCAAAGCCATATTCTAAATTCACTGTTGAATGCCTGTCCCA
5551 GTCCAAATTGTCTGTCTGCTCTTATTTTTGTACCATATTGCTCTTAAAAATCTTGGTTTGGTACAGTTCATAATT
     CACCAAAAGTTCATATAATTTAAAGAAACACTAAATTAGTTTAAAATGAAGCAATTTATATCTTTATGCAAAAAC
5701 ATATGTCTGTCTTTGCAAAGGACTGTAAGCAGATTACAATAAATCCTTTACTTTAAAAAAAAAAAAAAAAAAA
```

FIG. 22E

```
hMR  548  SSFPPVNTLVESWKSHGDLSSRRSDGYPVLEYIPENVSSSTLRSVSTGSS

hGR  374  NLTSLGTLNFPGRTVFSNGYSSPS........MRPDVSSPPSSSSTATTG
                    ┌─DNA─→
hMR  598  RPSKICLVCGDEASGCHYGVVTCGSCKVFFKRAVEGQHNYLCAGRNDCII

hGR  416  PPPKLCLVCSDEASGCHYGVLTCGSCKVFFKRAVEGQHNYLCAGRNDCII
                              ←─DNA─┐
hMR  648  DKIRRKNCPACRLQKCLQAGMNLGARKSKKLGKLKGIHEEQPQQQQPPPP

hGR  466  DKIRRKNCPACRYRKCLQAGMNLEARKTKKKIKGIQQATTGVSQ......
                                                  ┌─STEROID─→
hMR  698  PPPPQSPEEGTTYIAPAKEPSVNTALVPQLSTISRALTPSPVMVLENIEP

hGR  510  ..................ETSENPGNKTIVPATLPQLTPTLVSLLEVIEP
```

FIG. 23A

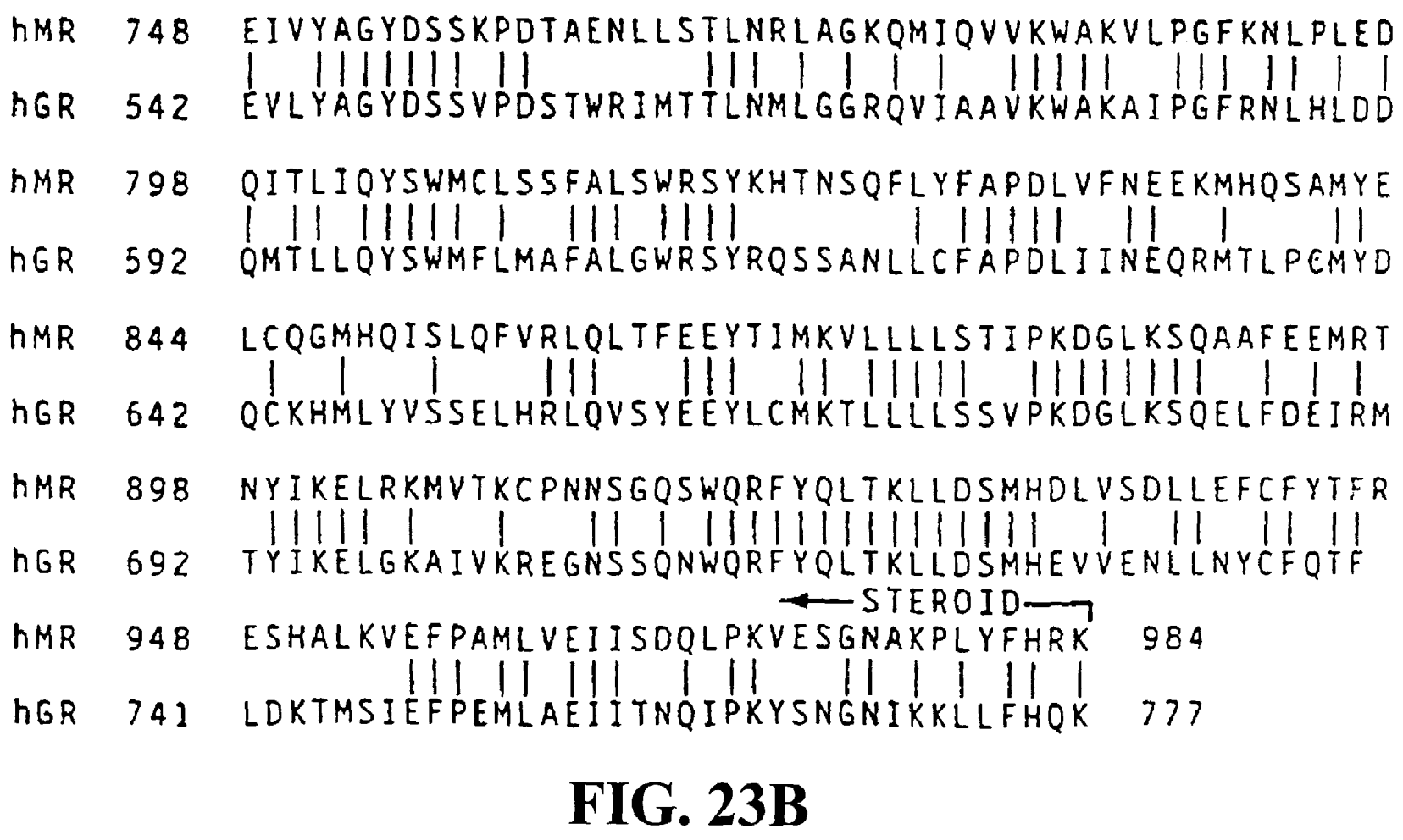

```
hMR  748  EIVYAGYDSSKPDTAENLLSTLNRLAGKQMIQVVKWAKVLPGFKNLPLED

hGR  542  EVLYAGYDSSVPDSTWRIMTTLNMLGGRQVIAAVKWAKAIPGFRNLHLDD

hMR  798  QITLIQYSWMCLSSFALSWRSYKHTNSQFLYFAPDLVFNEEKMHQSAMYE

hGR  592  QMTLLQYSWMFLMAFALGWRSYRQSSANLLCFAPDLIINEQRMTLPCMYD

hMR  844  LCQGMHQISLQFVRLQLTFEEYTIMKVLLLLSTIPKDGLKSQAAFEEMRT

hGR  642  QCKHMLYVSSELHRLQVSYEEYLCMKTLLLLSSVPKDGLKSQELFDEIRM

hMR  898  NYIKELRKMVTKCPNNSGQSWQRFYQLTKLLDSMHDLVSDLLEFCFYTFR

hGR  692  TYIKELGKAIVKREGNSSQNWQRFYQLTKLLDSMHEVVENLLNYCFQTF
                                        ←—STEROID—┐
hMR  948  ESHALKVEFPAMLVEIISDQLPKVESGNAKPLYFHRK  984

hGR  741  LDKTMSIEFPEMLAEIITNQIPKYSNGNIKKLLFHQK  777
```

FIG. 23B

HORMONE RECEPTOR COMPOSITIONS AND METHODS

This is a divisional application of U.S. Ser. No. 08/165,708, filed Dec. 10, 1993, now pending, which is, in turn a divisional application of U.S. Ser. No. 07/667,602, filed Mar. 7, 1991, now issued as U.S. Pat. No. 5,312,732, which is, in turn, a divisional application of U.S. Ser. No. 07/108,471, filed Oct. 20, 1987, now issued as U.S. Pat. No. 5,071,773, which is, in turn, a continuation-in-part of U.S. Ser. No. 06/922,585, filed Oct. 24, 1986, now abandoned, each of which is hereby incorporated by reference.

ACKNOWLEDGMENT

This invention was made with government support under a grant from the National Institutes of Health (Grant No. GM 26444).

FIELD OF THE INVENTION

The present invention relates to hormone receptor proteins and genes encoding them, modification of such receptors and genes by recombinant DNA and other genetic engineering techniques, plus uses of such receptors and genes, both unmodified and modified. More particularly, the invention concerns steroid and thyroid hormone receptors and associated genes. Most particularly, it concerns human glucocorticoid, mineralocorticoid and thyroid hormone receptors and genes for them. In addition the invention relates to a novel bioassay system for determining the functionality of hormone receptor proteins coded for by receptor DNA clones, plus novel methods for inducing and controlling expression of genes whose transcription is activated by hormones complexed with receptor proteins.

BACKGROUND OF THE INVENTION

Transcriptional regulation of development and homeostasis in complex eukaryotes, including humans and other mammals, birds, and fish, is controlled by a wide variety of regulatory substances, including steroid and thyroid hormones. These hormones exert potent effects on development and differentiation in phylogenetically diverse organisms and their actions are mediated as a consequence of their interactions with specific, high affinity binding proteins referred to as receptors. See generally, Jensen, et al., (1972); Gorski, et al., (1976); Yamamoto, et al., (1976); O'Malley, et al., (1969); Hayward, et al., (1982); and Asburner, et al., (1978).

Receptor proteins, each especially specific for one of the several classes of cognate steroid hormones (i.e., estrogens (estrogen receptor), progestogens (progesterone receptor), glucocorticoids (glucocorticoid receptor), androgens (androgen receptor), aldosterones (mineralocorticoid receptor) or for cognate thyroid hormones (thyroid hormone receptor), are known and distributed in a tissue specific fashion. See Horwitz, et al., (1978) and Pamiter, et al., (1976).

Turning now to the interaction of hormones and receptors, it is known that a steroid or thyroid hormone enters cells by facilitated diffusion and binds to its specific receptor protein, initiating an allosteric alteration of the protein. As a result of this alteration, the hormone/receptor complex is capable of binding to certain specific sites on chromatin with high affinity. See Yamamoto, et al., (1972) and Jensen, et al., (1968).

It is also known that many of the primary effects of steroid and thyroid hormones involve increased transcription of a subset of genes in specific cell types. See Peterkofsky, et al., (1968) and McKnight, et al., (1968). Moreover, there is evidence that activation of transcription (and, consequently, increased expression) of genes which are responsive to steroid and thyroid hormones (through interaction of chromatin with hormone receptor/hormone complex) is effected through binding of the complex to enhancers associated with the genes. (See Khoury, et al., 1983.)

In any case, a number of steroid hormone and thyroid hormone responsive transcriptional control units, some of which have been shown to include enhancers, have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens, and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic alpha$_{2u}$-globulin gene transcriptional control units, responsive to androgens, estrogens, thyroid hormones and glucocorticoids. (See the Introduction portion of Experimental Section I of this Specification for references.)

A major obstacle to further understanding and more practical use of the steroid and thyroid hormone receptors has been the lack of availability of the receptor proteins, in sufficient quantity and sufficiently pure form, to allow them to be adequately characterized. The same is true for the DNA gene segments which encode them. Lack of availability of these DNA segments has prevented in vitro manipulation and in vivo expression of the receptor-coding genes, and consequently the knowledge such manipulation and expression will yield.

The present invention is directed to overcoming these problems of short supply of adequately pure receptor material and lack of DNA segments which encode the receptors.

REFERENCE LIST

The Background section of the specification refers to the following publications.

Publications

1. Asburner, M., and Berendes, H. D. in *The Genetics and Biology of Drosophila*, Eds. Ashburner, M., and Wright, T. R. F., Vol. 2, pp. 315–395, Academic, London (1978).
2. Gorski, J., and Gannon, F., *A. Rev. Physiol.,* 38:425–450 (1976).
3. Hayward, M. A., Brock, M. L. and Shapiro, D. J., *Nucleic Acids Res.,* 10:8273–8284 (1982).
4. Horwitz, K. B., and McGuire, W. L., *J. Biol. Chem.,* 253:2223–2228 (1978).
5. Jensen, E. V., and DeSombre, E. R., *A. Rev. Biochem.,* 41:203–230 (1972).
6. Jensen, E. V., et al., *Proc. Natl. Acad. Sci. U.S.A.,* 59:632–638 (1968).
7. Khoury, G., and Gruss, P., *Cell,* 33:313–314 (1983).
8. McKnight, G. S., and Palmiter, R. D., *J. Biol. Chem.,* 254:9050–9058 (1968).

9. O'Malley, B. W., McGuire, W. L., Kohler, P. O., and Kornman, S. G., *Recent Prog. Horm. Res.,* 25:105–160 (1969).

10. Pamiter, R. D., Moore, P. B., Mulvihill, E. R. and Emtage, S., *Cell,* 8:557–572 (1976).

11. Peterkofsky, B., and Tomkins, G., *Proc. Natl. Acad. Sci. U.S.A.,* 60:222–228 (1968).

12. Yamamoto, K. R., and Alberts, B. M., *A. Rev. Biochem.,* 45:721–746 (1976).

13. Yamamoto, K. R., and Alberts, B. M., *Proc. Natl. Acad. Sci. U.S.A.,* 69:2105–2109 (1972).

Other Publications

Some of the information disclosed in this specification has been published:

The study disclosed in Experimental Section I has been published as: Hollenberg, S. M., Weinberger, C., Ong, E. S., Cerelli, G., Oro, A., Lebo, R., Thompson, E. B., Rosenfeld, M. G., and Evans, R. M., "Primary Structure and Expression of a Functional Human Glucocorticoid Receptor cDNA", *Nature* (London), 318:635–641 (December, 1985).

The study disclosed in Experimental Section II has been published as: Giguere, V., Hollenberg, S. M., Rosenfield, M. G., and Evans, R. M., "Functional Domains of the Human Glucocorticoid Receptor", *Cell,* 46:645–652 (August, 1986)

The study disclosed in Experimental Section III has been published as: Arriza, J. L., Weinberger, C., Cerelli, G., Glaser, T. M., Handelin, B. L., Houseman, D. E., and Evans, R. M., "Cloning of Human Mineralocorticoid Receptor Complementary DNA: Structural and Functional Kinship with the Glucocorticoid Receptor", *Science,* 237:268–275 (July, 1987).

BRIEF DESCRIPTION OF THE DRAWINGS

The following is a brief description of the drawings. More detailed descriptions are found in the Experimental Sections of this sepcification.

The drawings comprise 33 Figures, of which:

EXPERIMENTAL SECTION I

Figure 1:
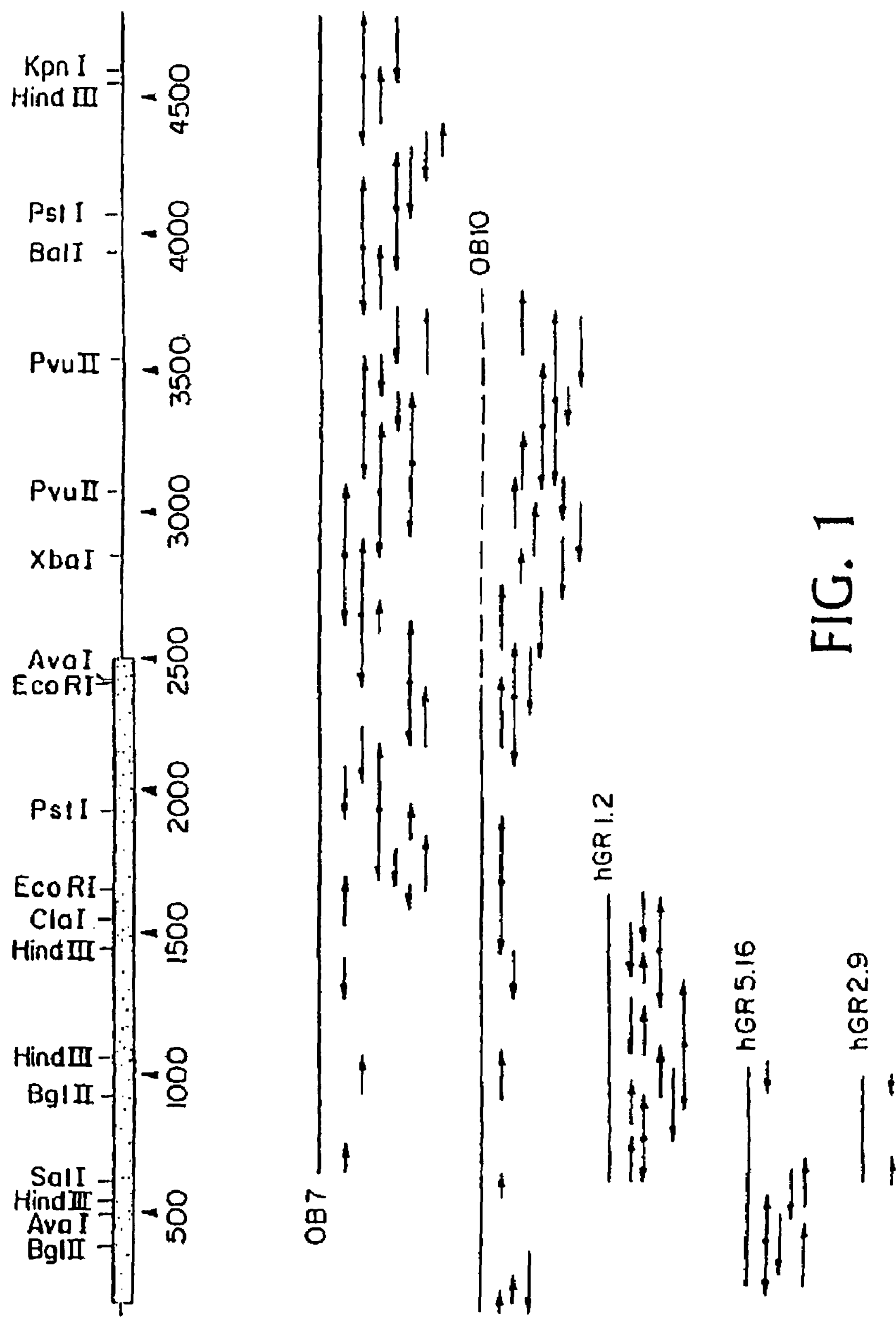
Figure 2:
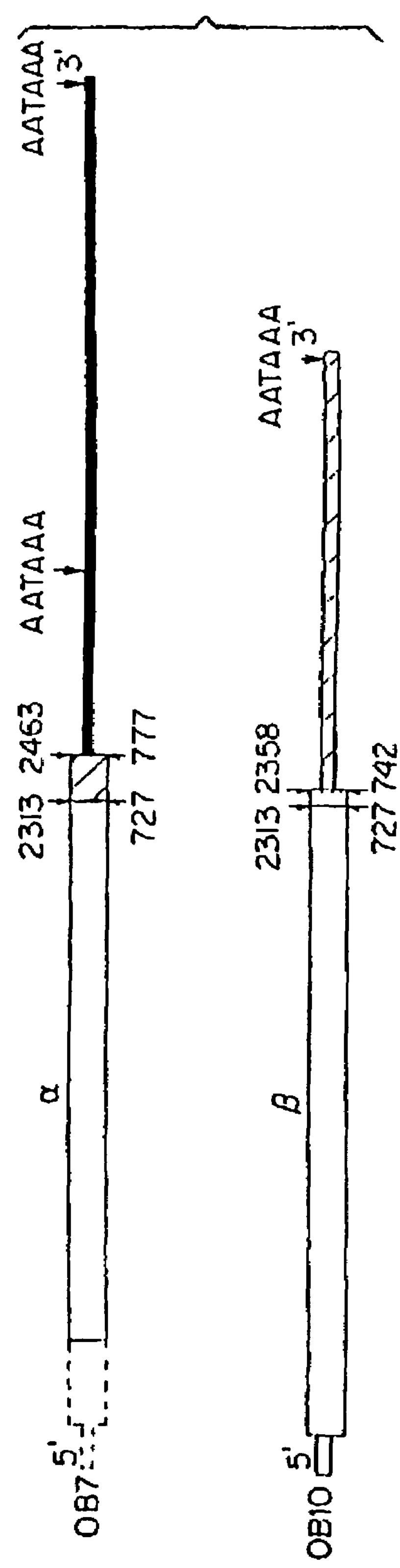

FIGS. 1 and 2 comprise a drawing which shows the human glucocorticoid receptor cDNA sequencing strategy (FIG. 1), plus a schematic representation of cDNA clones (FIG. 2).

FIGS. 3A–H are drawings which show the cDNA and predicted primary protein sequence of human glucocorticoid receptor (hGR).

Figure 4:
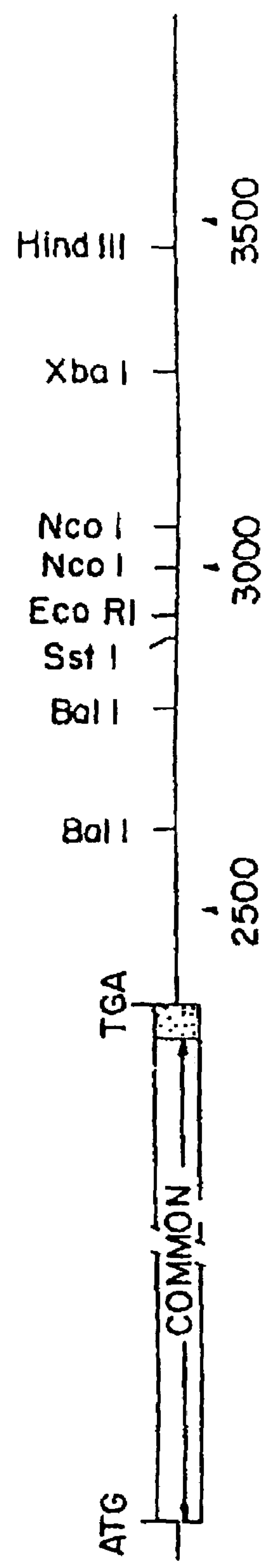

FIGS. 4 and 5 comprise a drawing which shows the restriction map (FIG. 4) and nucleotide sequence (FIG. 5) of the 3' end of the human glucocorticoid receptor beta cDNA (beta-hGR).

Figure 6:
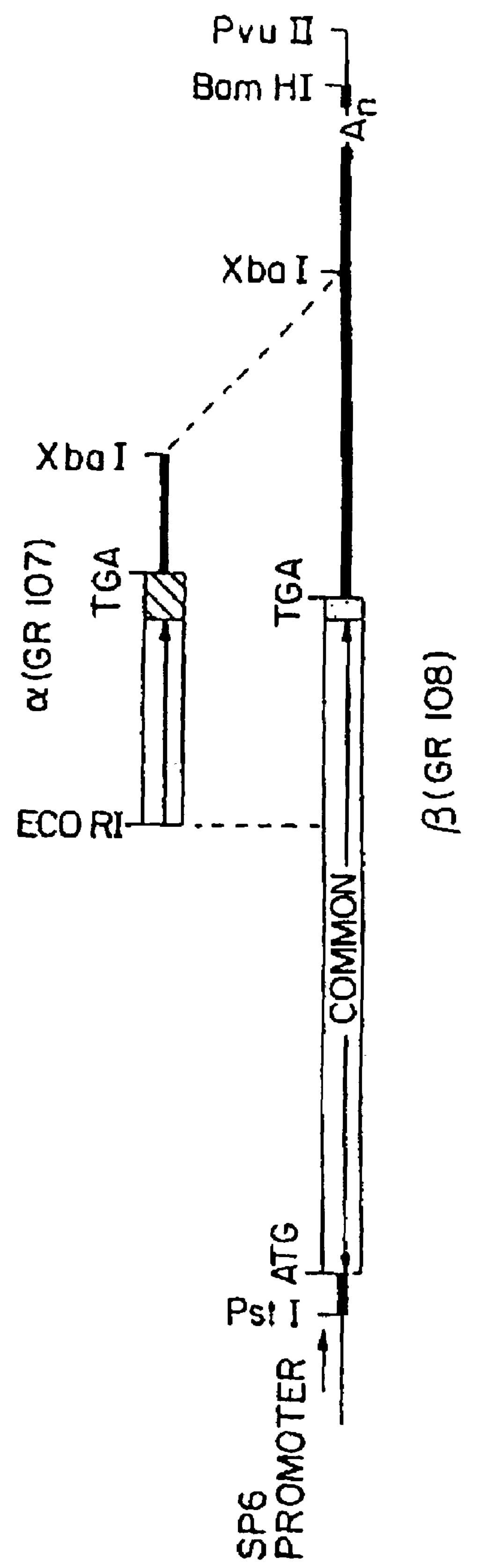
Figure 7:
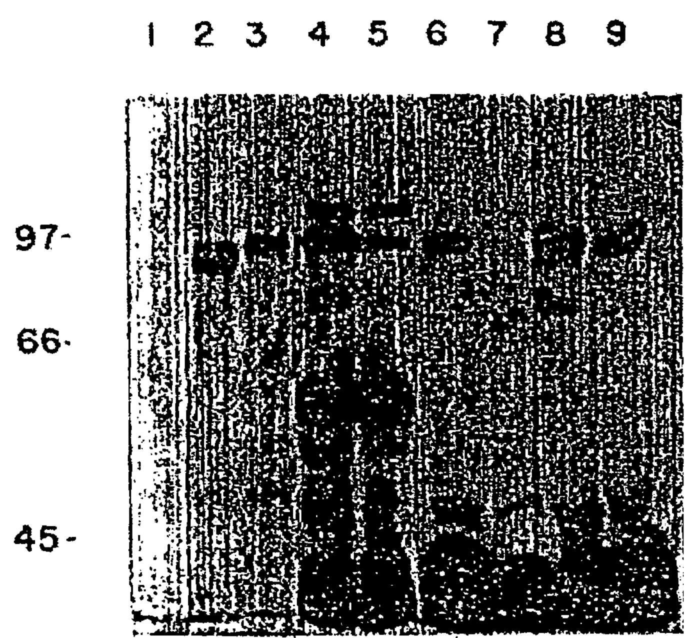

FIGS. 6 and 7 relate to an immunoblot comparison of hGR translated in vitro with in vivo hGR from cell extracts. FIG. 6 is a drawing showing the vectors constructed for in vitro transcription of the hGR cDNA sequence. FIG. 7 is a photograph showing a Western blot analysis of in vitro translation products and cell extracts.

Figure 8:
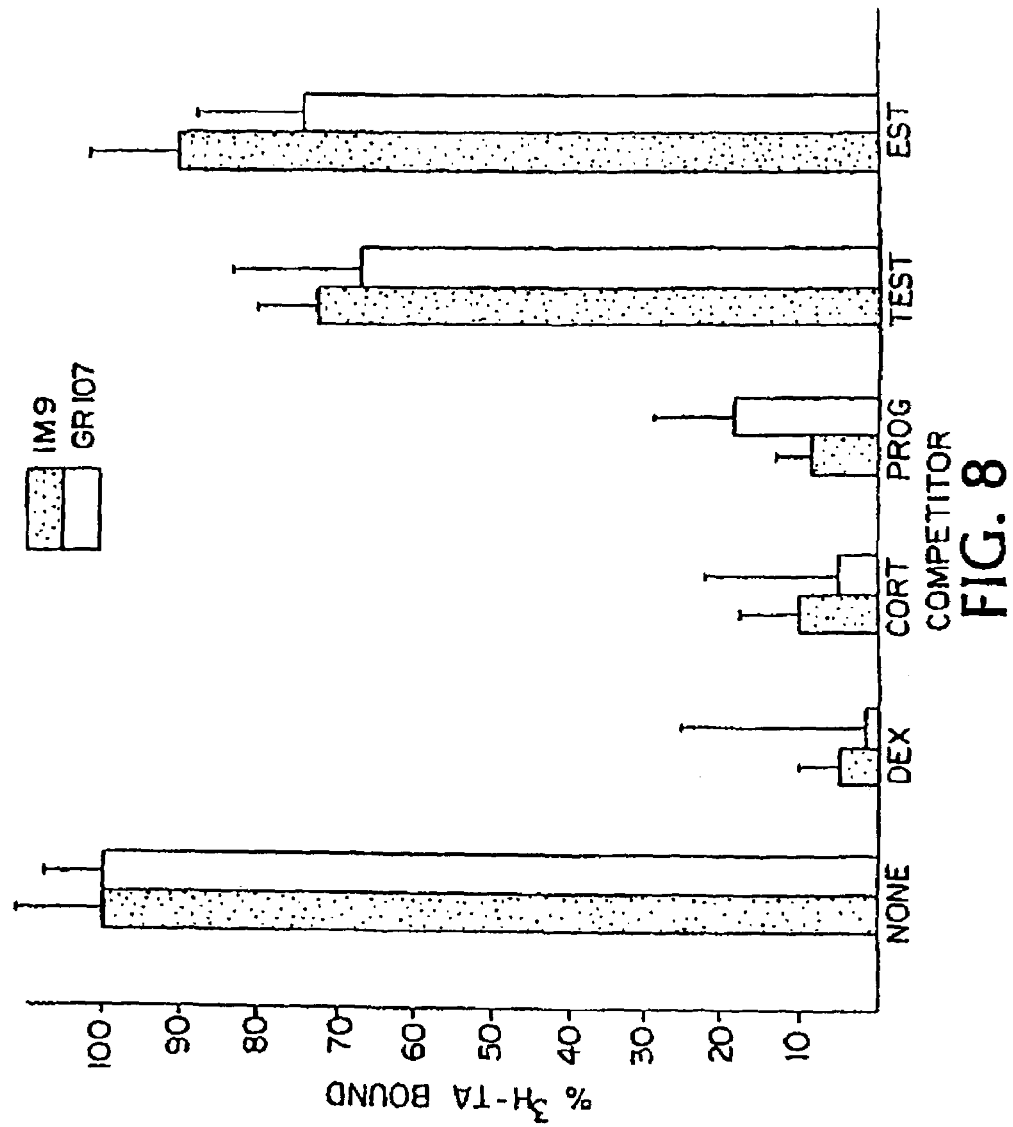

FIG. 8 is a graph showing steroid-binding of alpha-hGR (GR107) translated in vitro.

Figure 10:
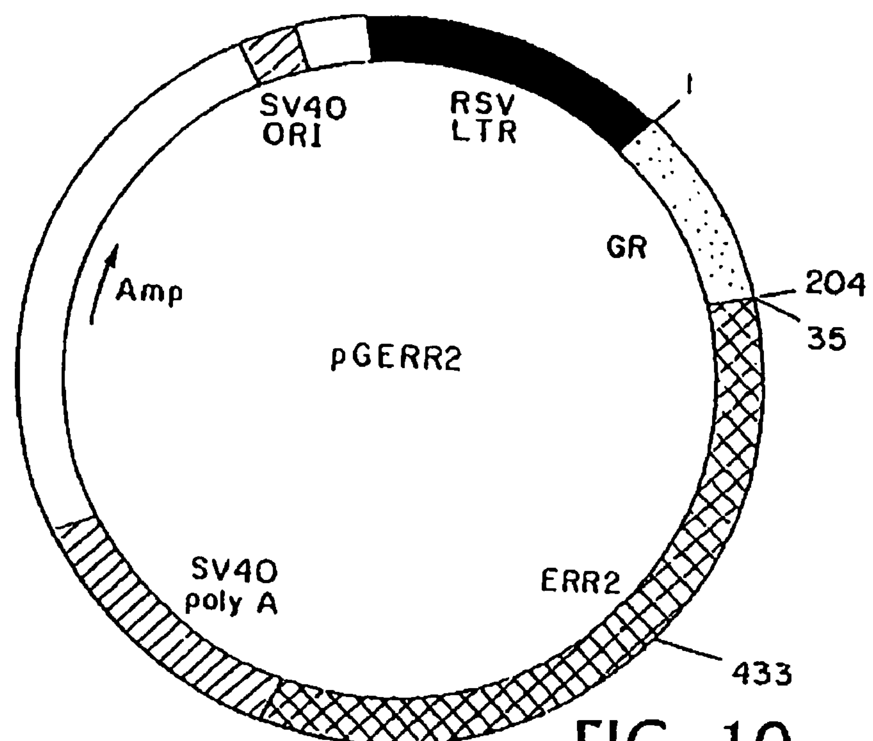
Figure 9:
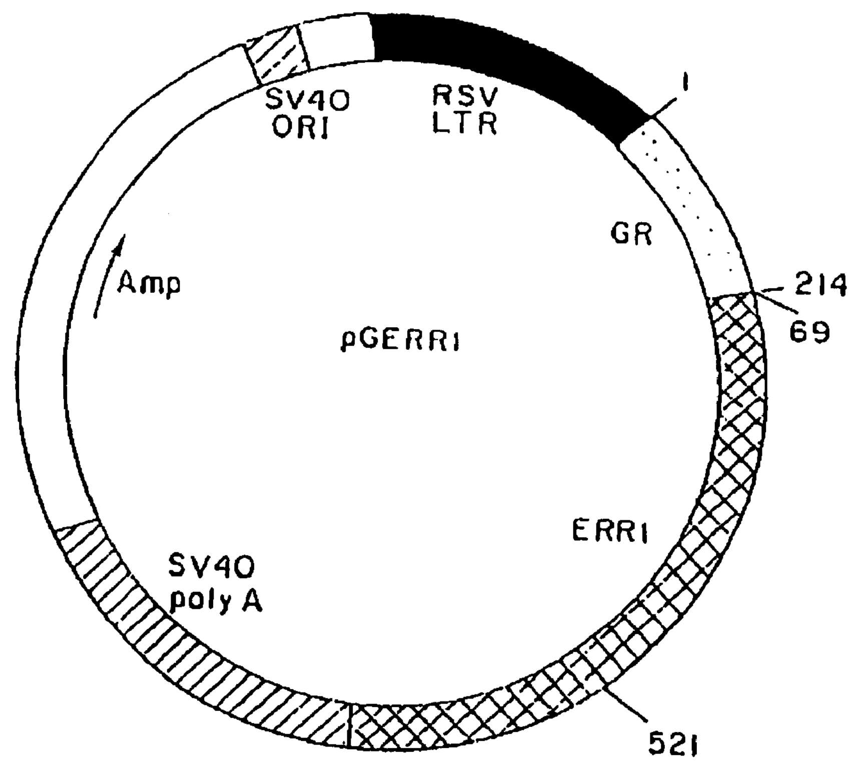

FIGS. 9 and 10 are schematic drawings of expression plasmids pGERR1 and pGERR2. Plasmid pGERR1 was used to express estrogen related receptor hERR1; pGERR2 was used to express hERR2.

EXPERIMENTAL SECTION II

Figure 11:
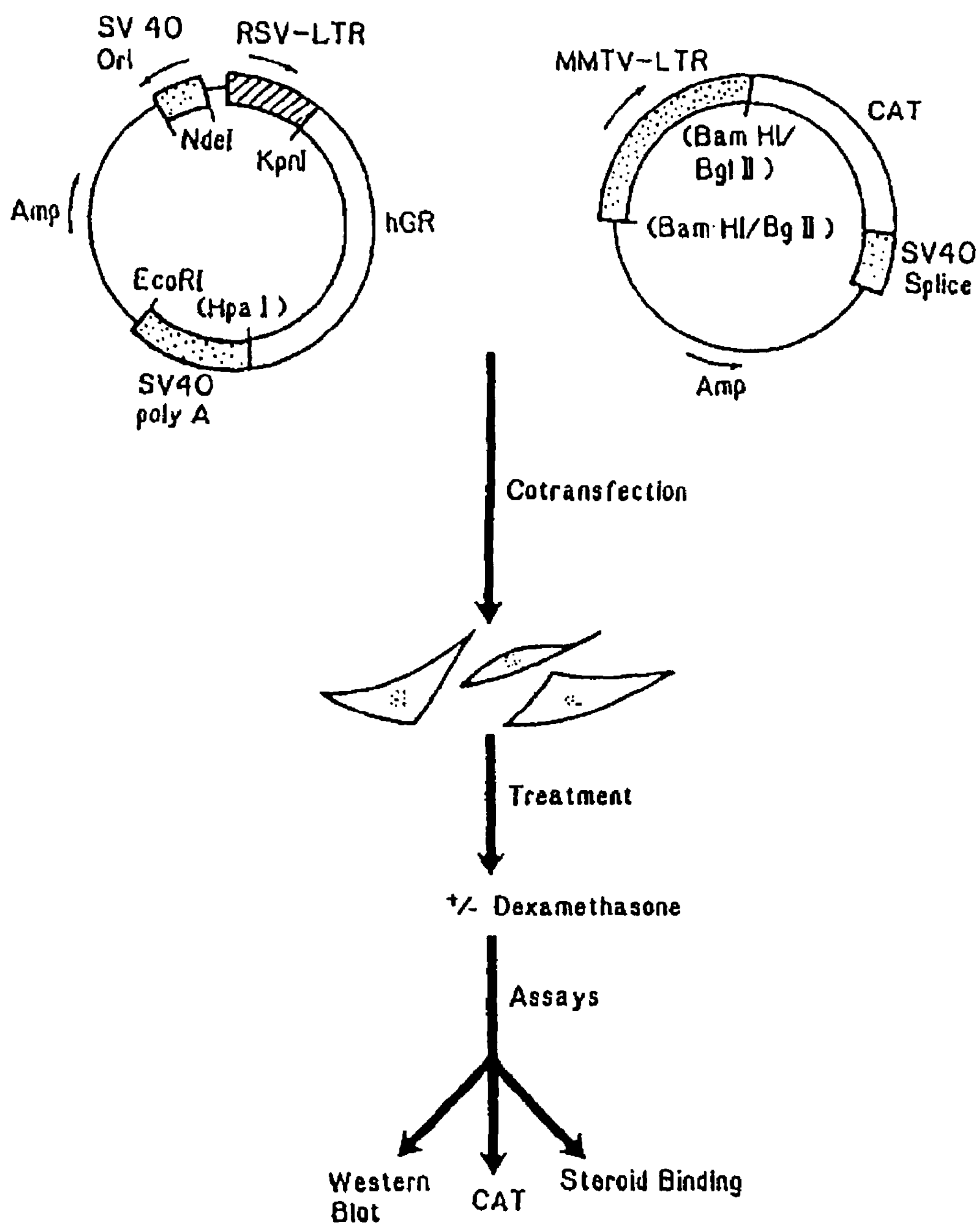

FIG. 11 is a drawing showing a schematic representation of the hGR functional assay.

Figure 12:
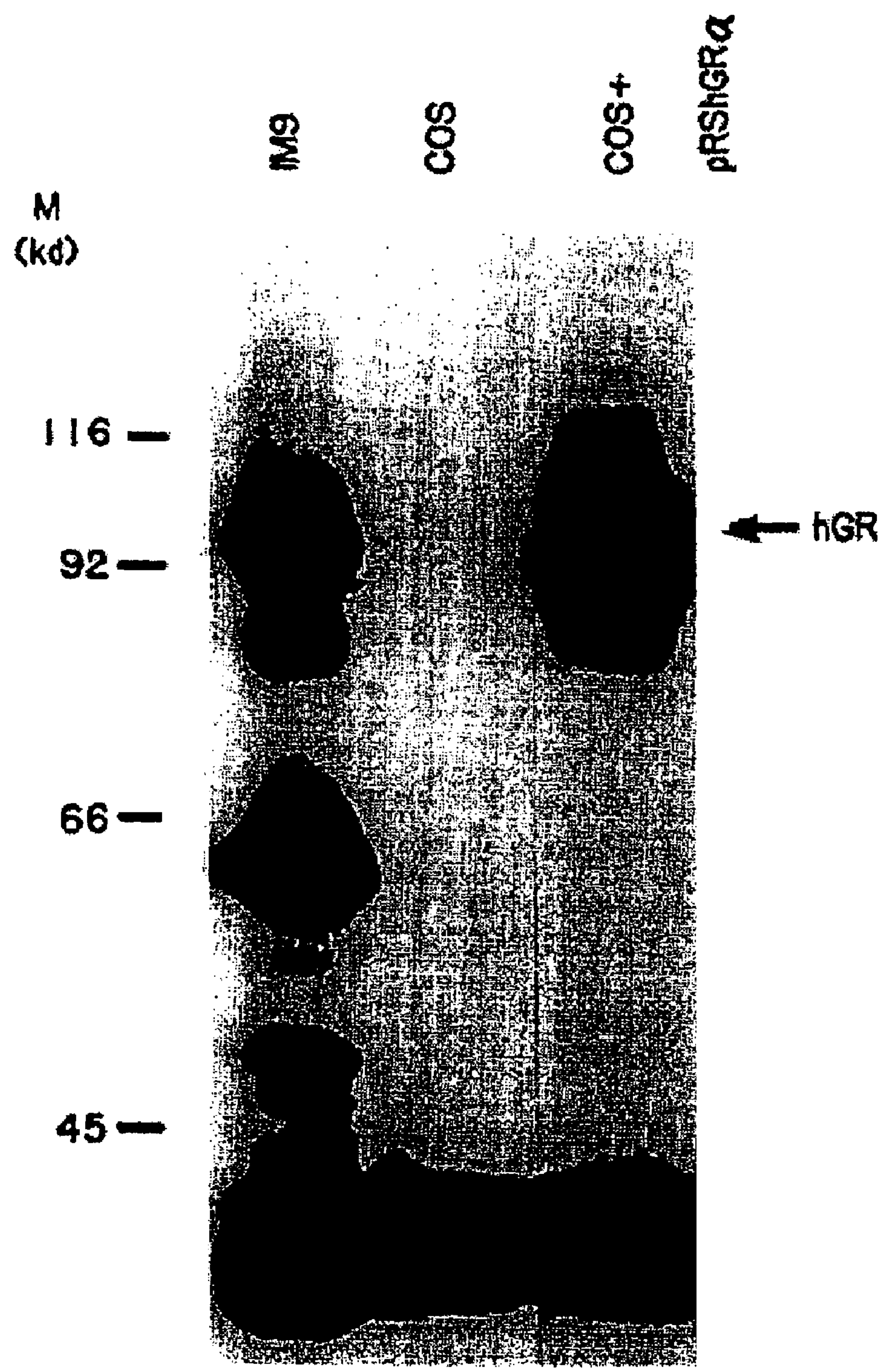

FIG. 12 is a photograph showing a Western blot analysis which illustrates expression of hGR protein.

Figure 13:
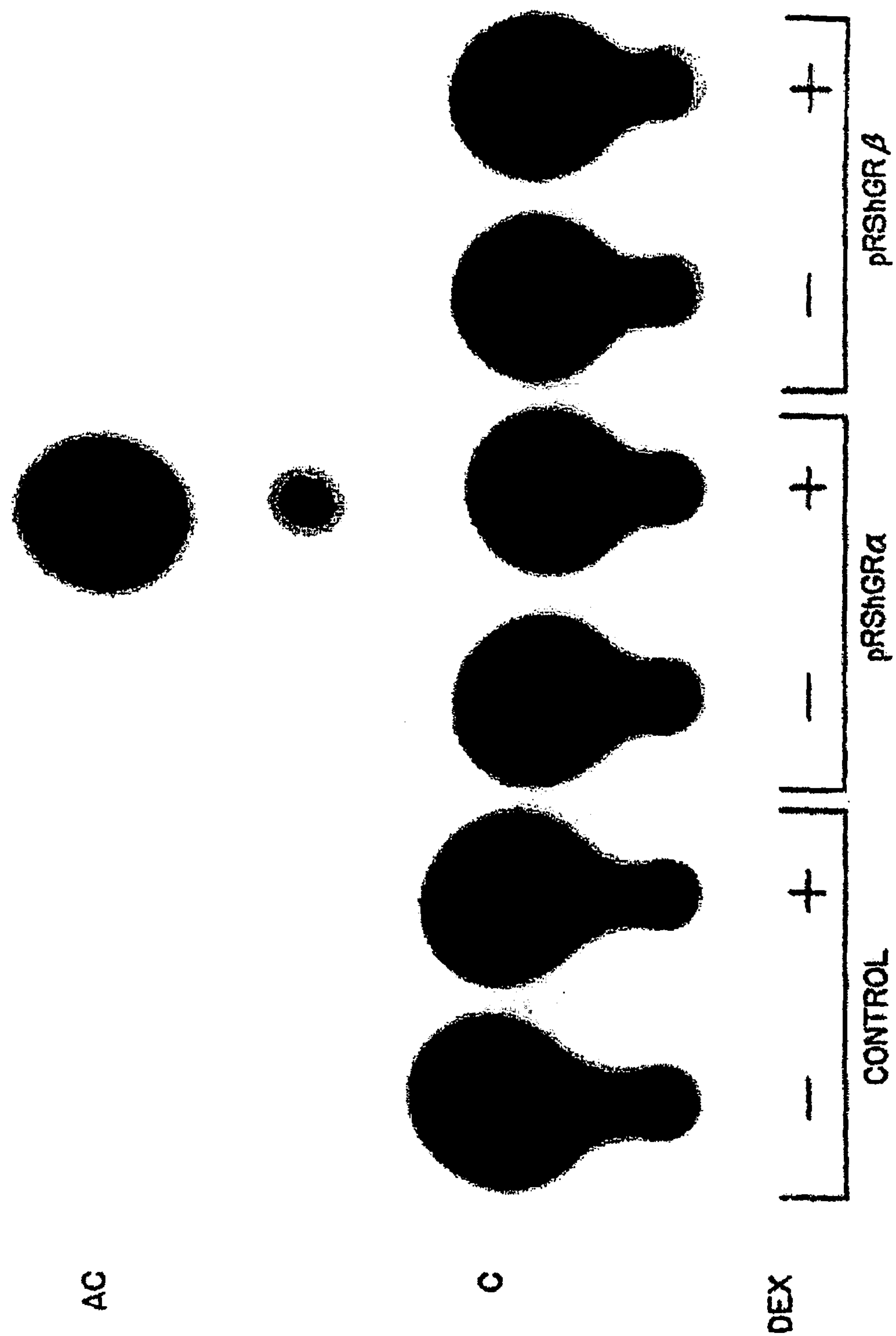

FIG. 13 is a photograph of a blot which illustrates induction of CAT activity by hGR.

Figure 15:
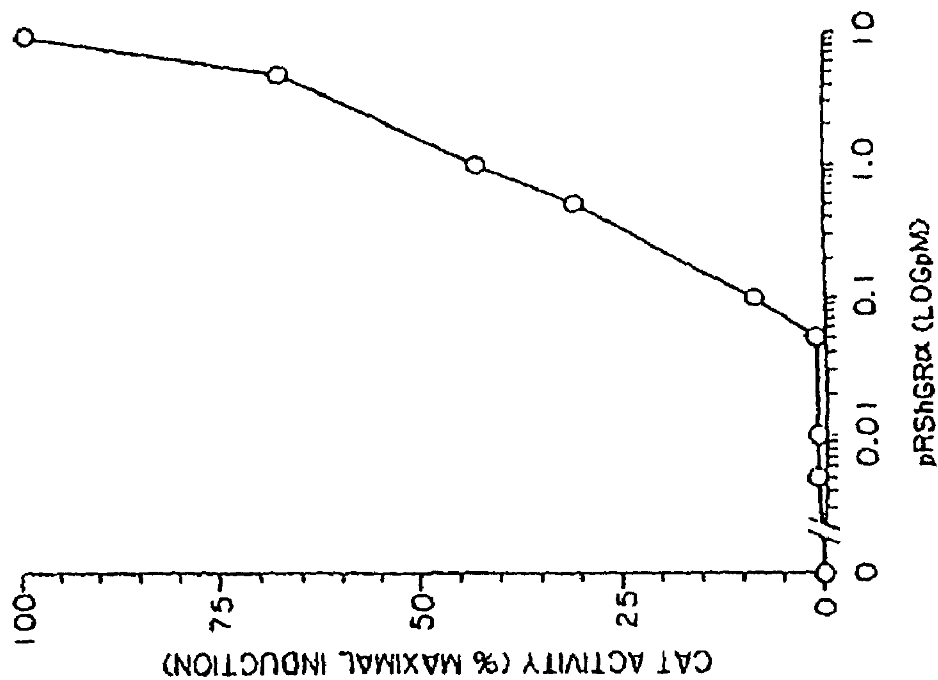
Figure 14:
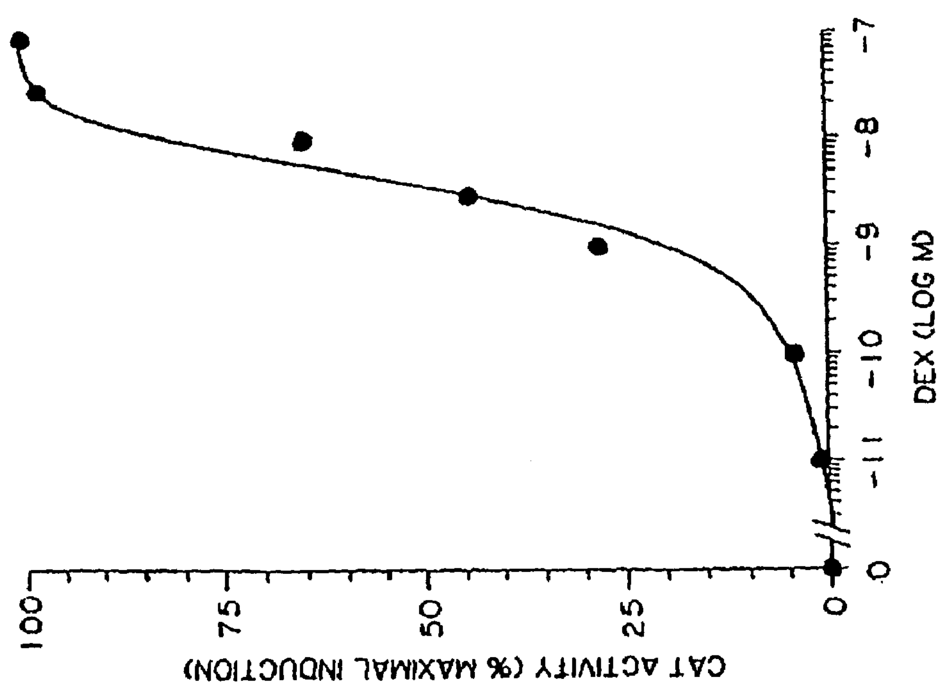

FIGS. 14 and 15 comprise a graph. FIG. 14 shows the dose-response to DEX of pRShGR alpha; FIG. 15 shows the titration of pRShGRa.

Figure 16:
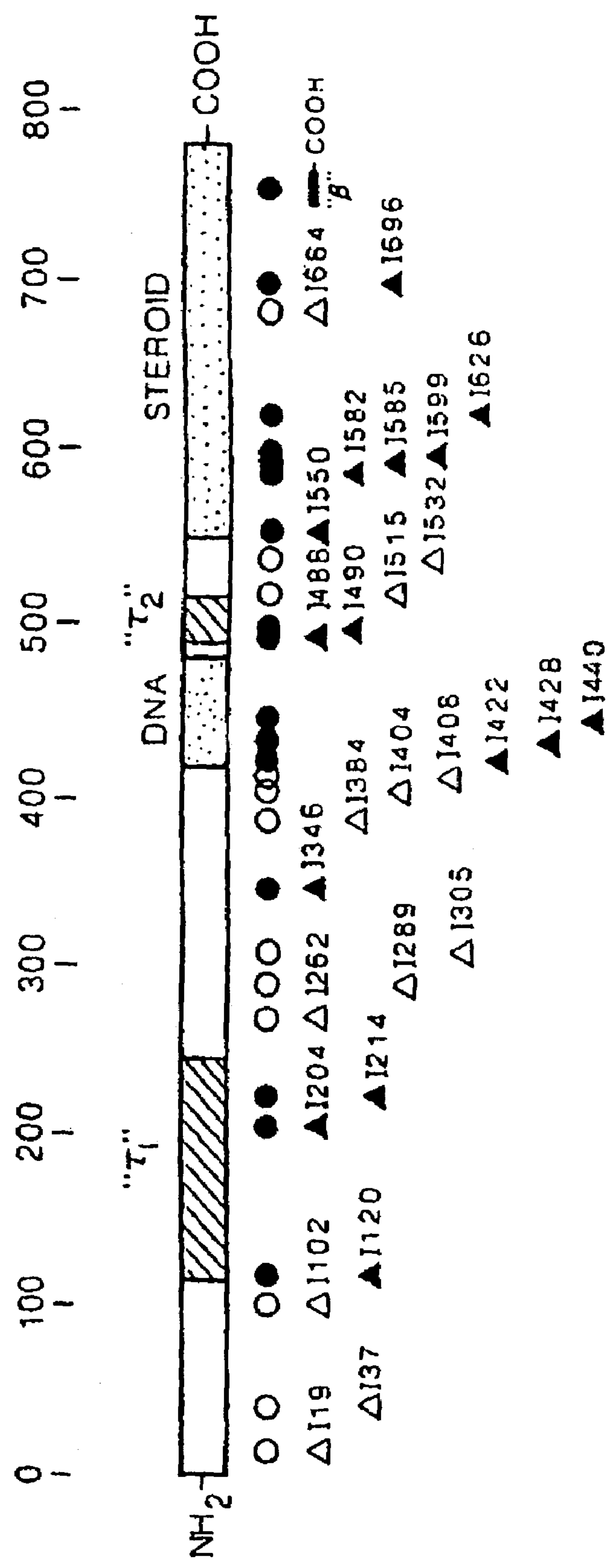

FIG. 16 is a schematic drawing showing the location of functional domains in hGR.

EXPERIMENTAL SECTION III

Figure 19:
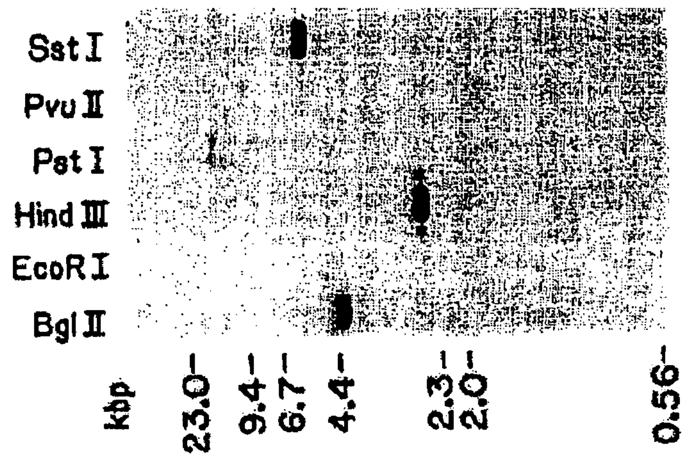
Figure 18:
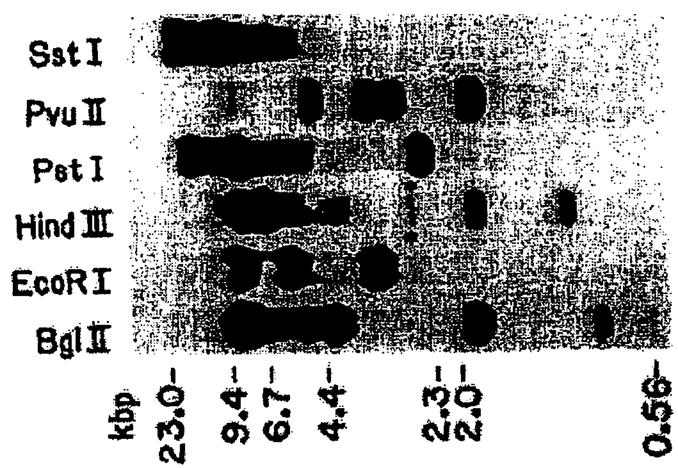
Figure 17:
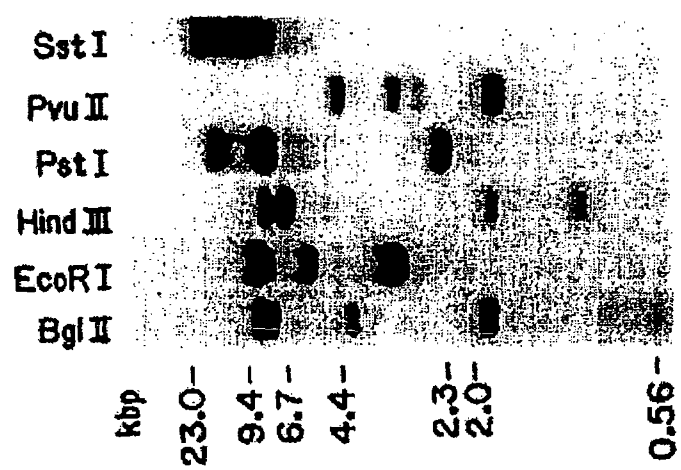

FIGS. 17–20 are comprised of three photographs and one schematic drawing, all of which concern to isolation of a genomic sequence related to the hGR gene. FIG. 17 is a photograph showing high-stringency Southern analysis of human placenta DNA digested with the indicated nucleases. FIG. 18 is similar except that it shows low-stringency Southern analysis. FIG. 19 is also a photograph of a Southern blot; it demonstrates isolation of the genomic sequence in a clone designated lambda HGH. FIG. 20 is a schematic drawing which shows the intron-exon structure of lambda HGH genomic fragment and its homology with hGR.

Figure 21:
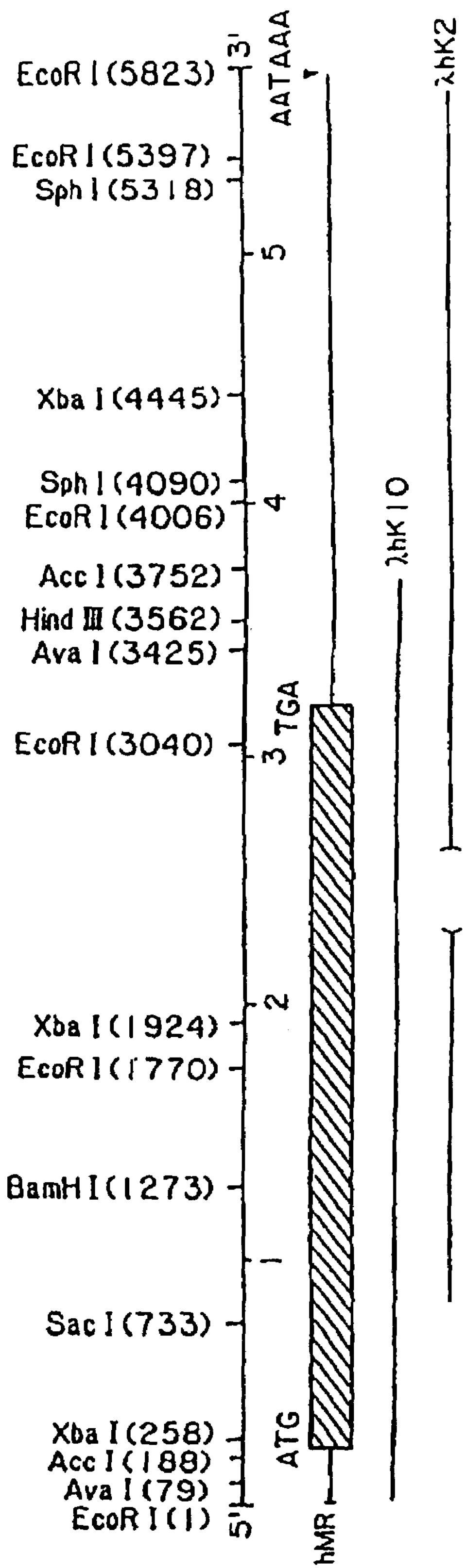

FIGS. 21 and 22A–E are drawings which show the cDNA nucleotide sequence and the predicted primary protein sequence of human mineralocorticoid receptor. FIG. 21 shows the composite structure of hMR aligned with a line diagram of some restriction endonuclease cleavage sites. FIGS. 22A–E show the complete nucleotide sequence of hMR and its primary predicted amino acid sequence.

FIGS. 23A and B are drawings which show the amino acid homology between mineralocorticoid receptor and glucocorticoid receptor.

Figure 24:
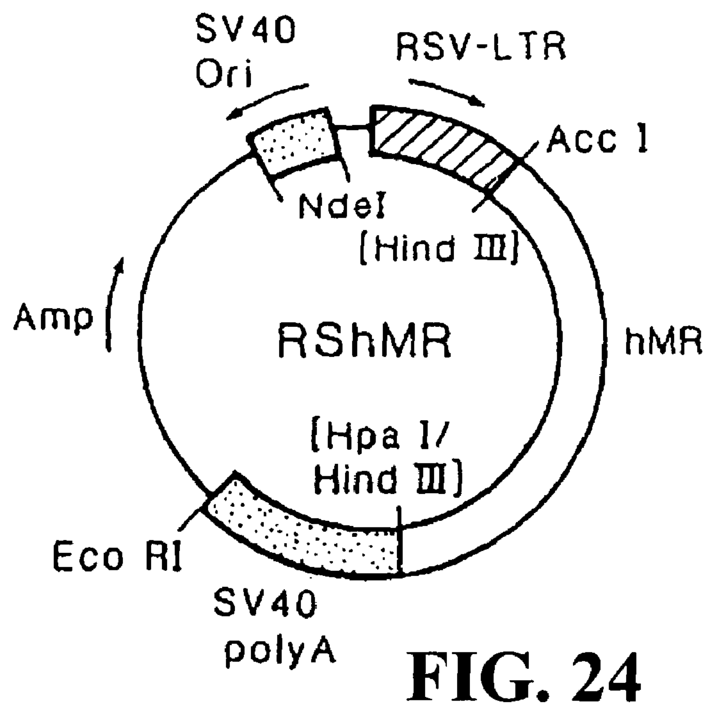
Figure 25:
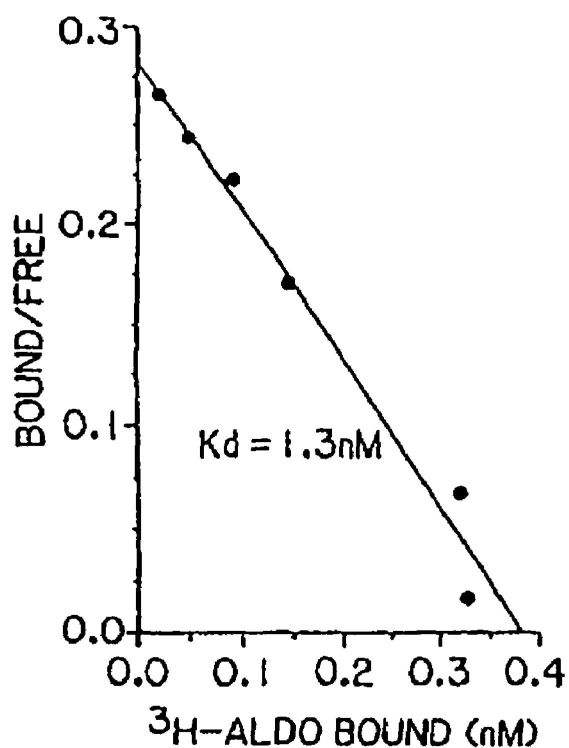
Figure 26:
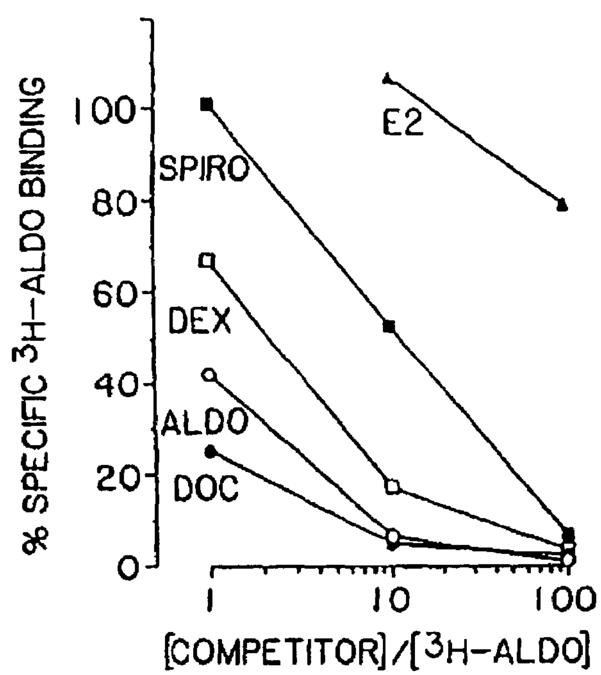
Figure 27:
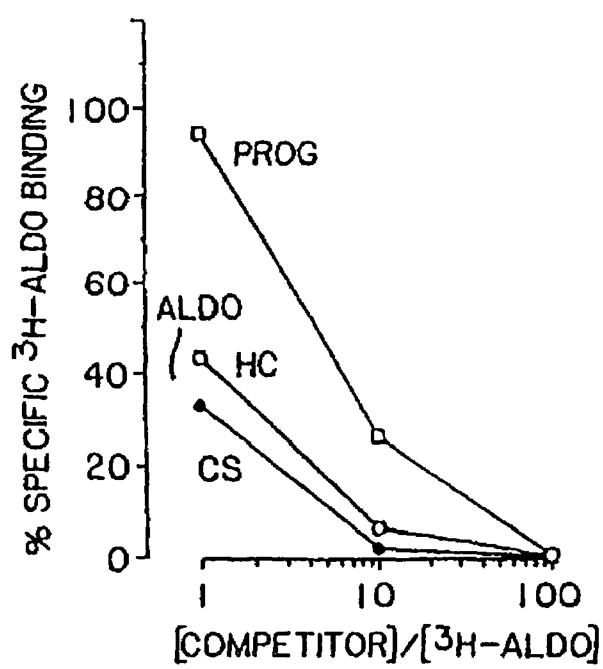

FIGS. 24–27 comprise a drawing and three graphs which relate to the steroid-binding properties of expressed hMR. FIG. 24 shows the structure of expression plasmid pRShMR, the plasmid used to express hMR. FIG. 25 is a graph showing Scatchard analysis of tritiated aldosterone binding in extracts prepared from pRShMR-transfected COS cells. FIGS. 26 and 27 are graphs showing competition of unlabeled steroids for binding with [$^3$H]aldosterone in transfected COS cells.

Figure 28:
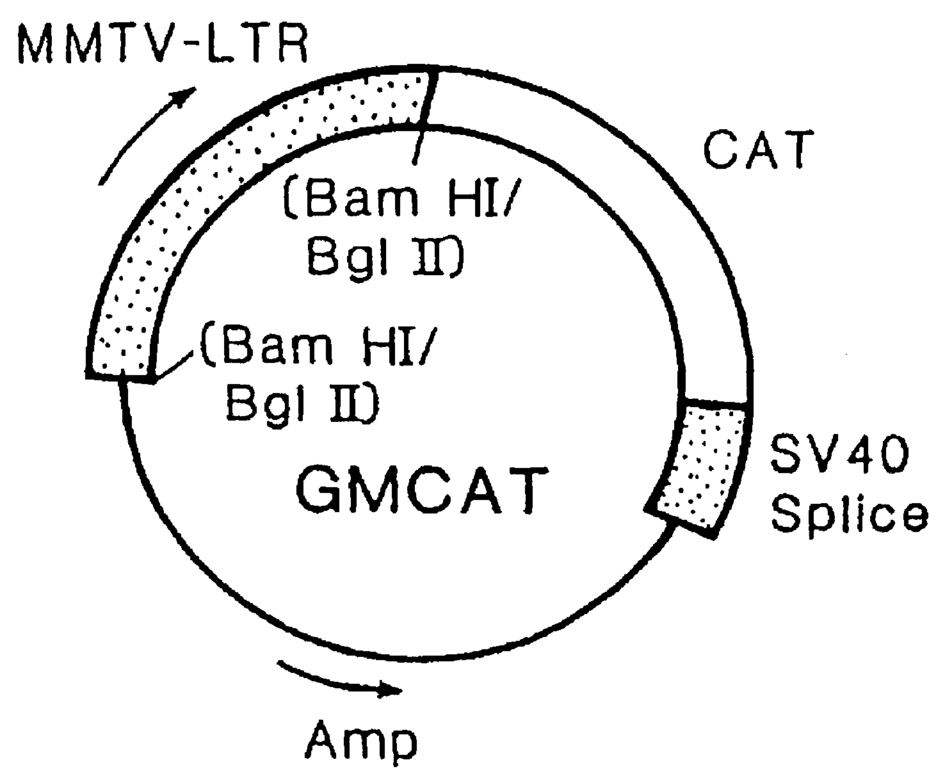
Figure 29:
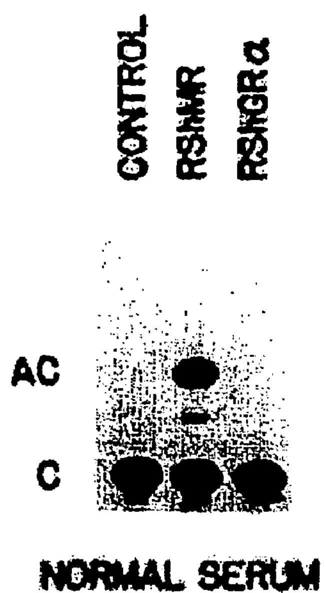
Figure 30:
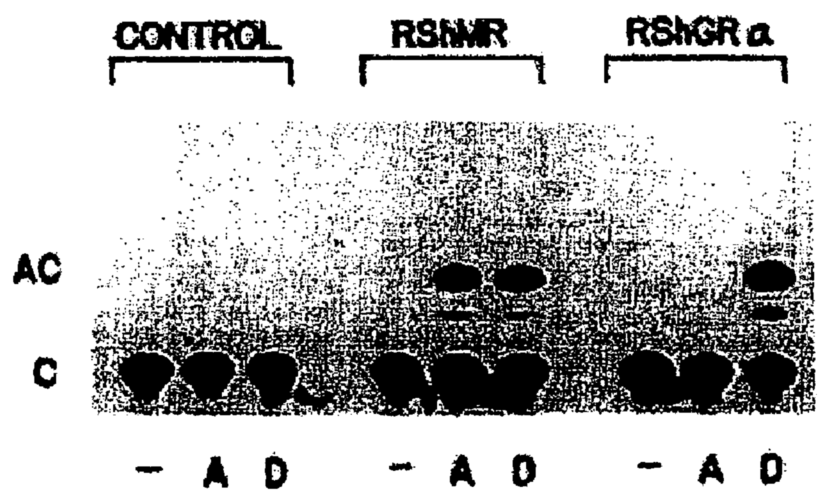

FIGS. 28–30 are drawings and two photographs which show transcriptional activation of MMTV LTR by hMR and hGR expression plasmids in transfected CV-1 cells. FIG. 28 is a schematic drawing of plasmid GMCAT. FIG. 29 is a photograph of a blot which shows differential CAT enzyme activity found after hMR or hGR transfection with normal serum. FIG. 30 is a photograph of a blot which shows differential induction of CAT activity by aldosterone or dexamethasone in cells transfected with hMR or hGR.

Figure 31:
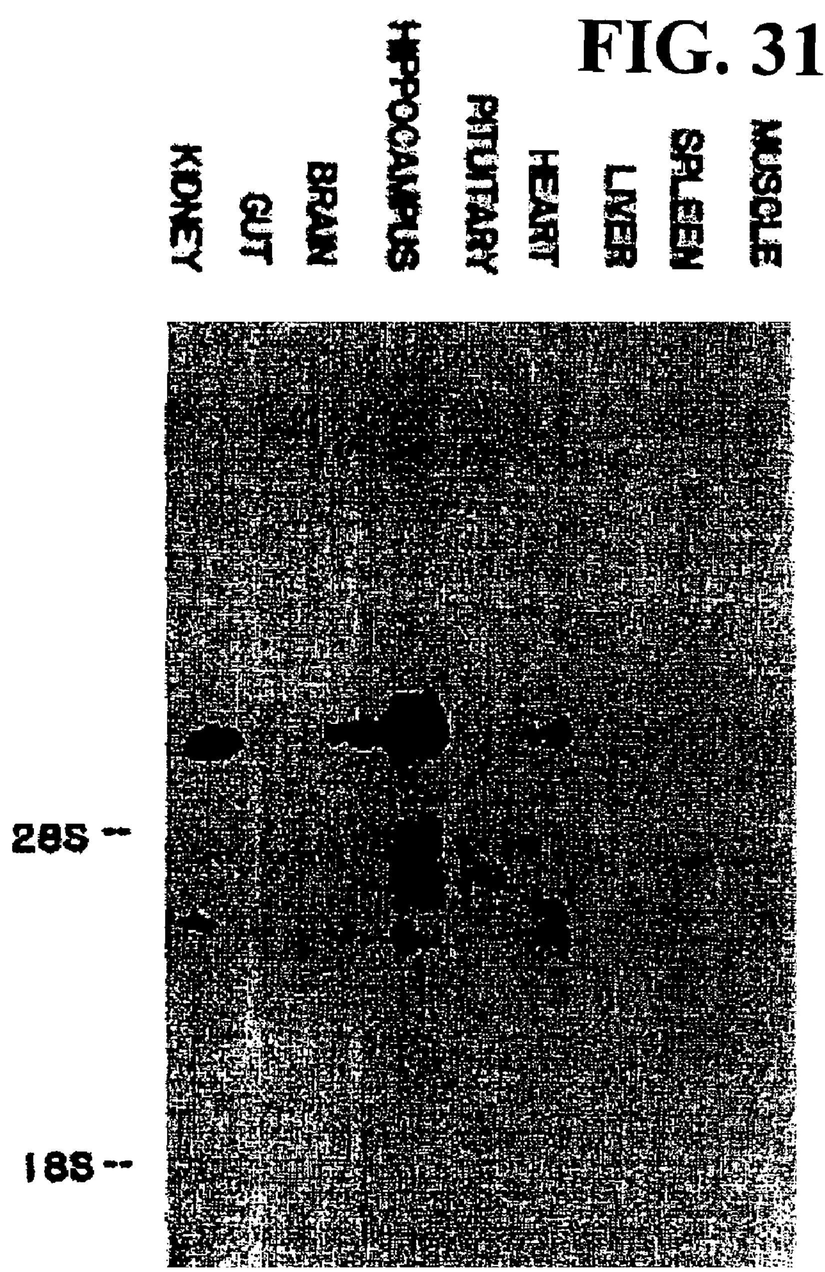

FIG. 31 is a photograph of a blot showing Northern analysis of mineralocorticoid receptor mRNA's in rat tissues.

Figure 32:
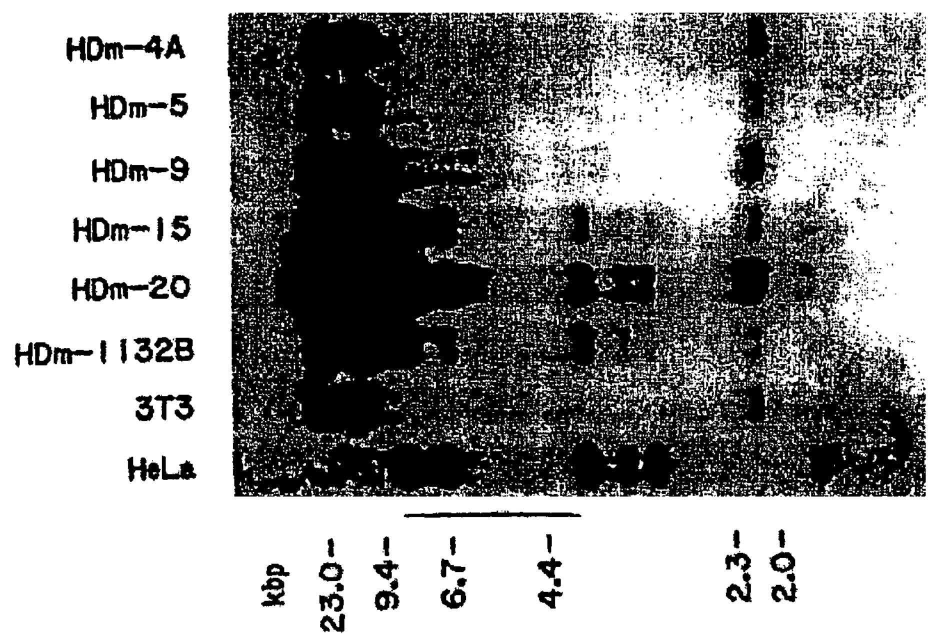

FIG. 32 is a photograph showing chromosomal localization of hMR gene by Southern analysis of microcell hybrids.

Figure 33:
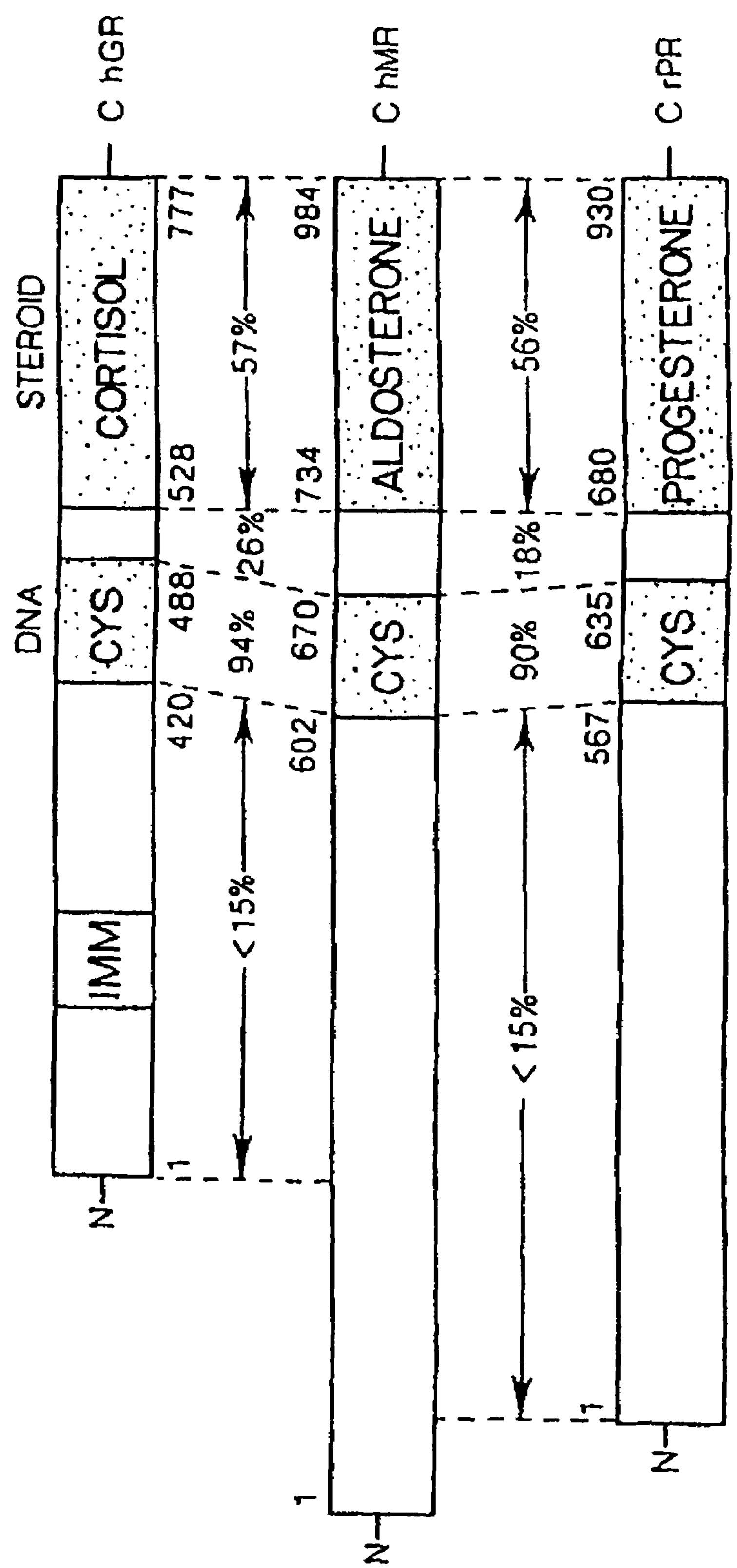

FIG. 33 is a schematic drawing showing amino acid comparisons of the hGR, hMR, and hPR structures.

DEFINITIONS

In the present specification and claims, reference will be made to phrases and terms of art which are expressly defined for use herein as follows:

As used herein, GR means glucocorticoid receptor. Disclosed DNA hGR codes for glucocorticoid receptor GR.

As used herein, MR means mineralocorticoid receptor. Disclosed DNA hMR codes for mineralocorticoid receptor MR.

As used herein, TR means thyroid receptor. Disclosed human DNA's c-erb-A, hERBA 8.7 and hFA8, and rat rbeA12, all code for thyroid receptor.

As used herein, hERR1 and hERR2 designate DNA's which code for estrogen-related receptor proteins.

As used herein, glucocorticoid hormones include cortisol, hydrocortisone (HC), and corticosterone (CS), and analogs thereof include dexamethasone (Dex), deoxycorticosterone (Doc), and triamcinolone acetonide.

As used herein, mineralocorticoids include aldosterone (Aldo), as well as corticosterone (CS), and deoxycorticosterone (Doc).

As used herein, thyroid hormones include thyroxine (T4) and triiodothyronine (T3).

As used herein, estrogens (or oestrogens) include estradiol-17 beta, and analogs thereof include diethylstilbestrol.

As used herein, progestogens include progesterone (Prog), and analogs thereof include promegestone.

As used herein, androgens include dihydroxytestosterone, and analogs thereof include methyltrienolone.

As used herein, MTV means mammary tumor virus; MMTV means mouse mammary tumor virus.

As used herein, RSV means Rous sarcoma virus; SV means Simian virus.

As used herein, CAT means chloramphenicol acetyltransferase.

As used herein, COS means monkey kidney cells which express T antigen (Tag). See Gluzman, *Cell,* 23:175 (1981). COS cells are useful in the bioassay system of the present invention.

As used herein, CV-1 means mouse kidney cells from the cell line referred to as "CV-1". CV-1 is the parental line of COS. Unlike COS cells, which have been transformed to express SV40 T antigen (Tag), CV-1 cells do not express T antigen. Like COS cells, CV-1 cells are useful in the bioassay system and methods of the present invention.

As used herein, when it is said that a protein has "hormone-binding properties characteristic of a hormone receptor", it means that, if, in any standard assay for binding-affinity between a hormone from a species, or a synthetic analog thereof, and its cognate receptor(s) from that species, the affinity of the protein for the hormone or synthetic analog is at least about 10% of the affinity of the hormone or analog and the cognate receptor(s) from that species.

As used herein, when it is said that the transcription-activating property of a protein (X) is "characteristic" of that of a hormone receptor (R), it means that, if, when tested in an assay such as the "cis-trans" receptor functionality bioassay system of the invention, (See Description of the Invention; also see Experimental Section II, especially FIG. 11, plus the subsections labeled "Results" and "Experimental Procedures" which relate to use of the bioassay to show functional expression of hGR), the rate of expression from a gene (G) (whose transcription is activated by binding of: a receptor complexed with hormone or hormone analog) is, when protein (X) is employed in place of receptor (R), at least about 10% that shown when receptor (R) itself is used, as long as, in both the case of the "receptor" (R) and "protein (X)", the involved cells are bathed in the same concentration of hormone or analog thereof.

As used herein, when it is said that a protein has "hormone-binding or transcription-activating properties characteristic of a hormone receptor", it is intended that the hormone receptor itself be encompassed within this definition.

As used herein, when it is said that the transcription of a gene (G) is "substantially activated by hormone (H), or hormone analog (aH)", it means that the transcription of gene (G) is induced by binding of: a hormone/receptor [(H) or (aH)/(R) or (r)] complex to chromatin near where gene (G) is located. Under this definition (R) is meant to designate "wild-type" or unaltered hormone receptors. The lower case (r) notation is meant to designate functional "engineered" or "modified" receptor proteins, or proteins encoded by mRNA variants of "wild-type" receptor genes.

As used herein, GRE's mean glucocorticoid response elements and TRE's mean thyroid receptor enhancer-like DNA sequences. GRE's are enhancer-like DNA sequences that confer glucocorticoid responsiveness via interaction with the GR. See Payvar, et al., *Cell,* 35:381 (1983) and Schiedereit, et al., *Nature,* 304:749 (1983). TRE's are similar to GRE's except that they confer thyroid hormone responsiveness via interaction with TR.

As used herein, the terms "transcriptional control unit", "transcriptional control element", "hormone responsive promoter/enhancer element" and "DNA sequences which mediate transcriptional stimulation" mean the same thing, and are used interchangeably.

As used herein, in the phrase "operative hormone responsive promoter/enhancer element functionally linked to an operative reporter gene", the word "operative" means that the respective DNA sequences (represented by the terms "hormone responsive promoter/enhancer element" and "reporter gene") are operational, i.e., work for their intended purposes; the word "functionally" means that after the two segments are linked, upon appropriate activation by a hormone-receptor complex, the reporter gene will be expressed as the result of the fact that the "hormone responsive promoter" was "turned on" or otherwise activated.

As used herein, the term "receptor-negative" means that no receptor is detectable in the cell, or if it is, only a de minimus amount (i.e.) a barely detectable amount) of receptor is present.

As used herein, a "mutant" of a DNA of the invention means a DNA of the invention which has been genetically engineered to be different from the "wild-type" or unmodified sequence. Such genetic engineering can include the insertion of new nucleotides into the wild-type sequences, deletion of nucleotides from the wild-type sequences, or a substitution of nucleotides in the wild-type sequences.

Use of the term "substantial sequence homology" in the present specification and claims means it is intended that DNA or RNA sequences which have de minimus sequence variations from the actual sequences disclosed and claimed herein are within the scope of the appended claims.

The amino acids which comprise the various amino acid sequences appearing herein may be identified according to the following three-letter or one-letter abbreviations:

| Amino Acid | Three Letter Abbreviation | One-Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

The nucleotides which comprise the various nucleotide sequences appearing herein have their usual single-letter designations (A, G, T, C or U) used routinely in the art.

In the textual portion of the present specification and claims, references to Greek letters are written as alpha, beta, etc. In the Figures the corresponding Greek letter symbols are sometimes used.

Expression plasmid pGEM3 is commercially available from Promega Biotec, 2800 South Fish Hatchery Road, Madison, Wis. 53711.

DEPOSITS

Plasmids pRShGR-alpha, pRShMR, peA101, rbeA12 and GMCAT, all of which are in *E. coli* HB101, plasmids pE4 and pHKA, both of which are in *E. coli* DH5, plus plasmids phH3, phERBA 8.7 and phFA 8, have been deposited at the American Type Culture Collection, Rockville, Md., U.S.A. (ATCC) under the terms of the Budapest Treaty on the International Recognition of Deposits of Microorganisms for Purposes of Patent Procedure and the Regulations promulgated under this Treaty. Samples of the plasmids are and will be available to industrial property offices and other persons legally entitled to receive them under the terms of said Treaty and Regulations and otherwise in compliance with the patent laws and regulations of the United States of America and all other nations or international organizations in which this application, or an application claiming priority of this application, is filed or in which any patent granted on any such application is granted.

The ATCC Deposit Numbers for the ten deposits are as follows:

| | |
|---|---|
| pRShGR-alpha | 67200 |
| pRShMR | 67201 |
| peAl01 | 67244 |
| rbeAl2 | 67281 |
| GMCAT | 67282 |
| pE4 | 67309 |
| pHKA | 67310 |
| phERBA 8.7 | 40374 |
| phFA 8 | 40372 |
| phH 3 | 40373 |

SUMMARY OF THE INVENTION

In one aspect, the present invention comprises a double-stranded DNA segment wherein the plus or sense strand of the segment contains a sequence of triplets coding for the primary sequence of a protein which has hormone-binding and/or transcription-activating properties characteristic of a hormone receptor protein selected from the group consisting of: a glucocorticoid receptor, a mineralocorticoid receptor and a thyroid hormone receptor. According to this aspect of the invention, the double-stranded DNA segment is one which is capable of being expressed into the receptor protein.

In another aspect, the invention comprises a single-stranded DNA, which is the sense strand of a double-stranded DNA according to the invention, and an RNA made by transcription of a double-stranded DNA of the invention.

In another aspect, the invention comprises plasmids which contain DNA illustrative of the DNA of the present invention. These plasmids have been deposited with the American Type Culture Collection for patent purposes. The plasmids of the invention include plasmids selected from the group consisting of: pRShGR-alpha (ATCC #67200), pRShMR (ATCC #67201), peA101 (ATCC #67244), rbeA12 (ATCC #67281), GMCAT (ATCC #67282), pE4 (ATCC #67309), pHKA (ATCC #67310), phERBA 8.7 (ATCC #40374), phFA8 (ATCC #40372), and phH3 (ATCC #40373).

In still another aspect, the invention comprises a cell, preferably a mammalian cell, transformed with a DNA of the invention. According to this aspect of the invention, the transforming DNA is capable of being expressed in the cell, thereby increasing the amount of receptor, encoded by this DNA, in the cell.

Further the invention comprises cells, including yeast cells and bacterial cells such as those of *E. coli* and *B. subtilis*, transformed with DNA's of the invention.

Still further the invention comprises novel receptors made by expression of a DNA of the invention, or translation of an mRNA of the invention. According to this aspect of the invention, the receptors will be protein products of "unmodified" DNA's and mRNA's of the invention, or will be modified or genetically engineered protein products which, as a result of engineered mutations in the receptor DNA sequences, will have one or more differences in amino acid sequence from the corresponding naturally occurring "wild-type" or cognate receptor (i.e., the naturally occurring receptor of known sequence with the greatest amino acid sequence homology to the novel receptor). Preferably these receptors, whether "unmodified" or "engineered", will have at least about 10% of the hormone binding activity and/or at least about 10% of the transcription-activating activity of the corresponding naturally occurring cognate receptor.

The invention also comprises a novel method for determining the functionality of hormone receptor proteins produced from the DNA's (or mRNA's) of the invention. The new method, which is referred to herein as the "cis-trans" bioassay system, utilizes two plasmids: an "expression" plasmid and a "reporter" plasmid. According to the invention, the expression plasmid can be any plasmid which contains and is capable of expressing a receptor DNA of the invention, or an engineered mutant thereof, in a suitable receptor-negative host cell. Also according to the invention, the reporter plasmid can be any plasmid which contains an operative hormone responsive promoter/enhancer element functionally linked to an operative reporter gene.

In practicing the "cis-trans" bioassay of the invention, the expression plasmid (containing a "receptor" DNA of the invention) and the reporter plasmid are cotransfected into suitable receptor-negative host cells. The transfected host cells are then cultured in the presence and absence of a hormone, or analog thereof, which is able to activate the hormone responsive promoter/enhancer element of the reporter plasmid. Next the transfected and cultured host cells are monitored for induction (i.e., the presence) of the product of the reporter gene sequence. Finally, according to the invention, the expression and steroid binding-capacity of the receptor protein (coded for by the receptor DNA sequence on the expression plasmid and produced in the transfected and cultured host cells), is measured. (See FIG. 12 for a schematic drawing of this "cis-trans" bioassay system.)

The "cis-trans" bioassay system is especially useful for determining whether a receptor DNA of the invention has been expressed in a transformed host cell; it is also useful in determining whether a receptor of the invention has at least about 10% of the binding activity of the corresponding naturally occurring cognate receptor, as well as whether such a receptor has at least about 10% of the transcription-activating activity of the corresponding naturally occurring cognate receptor.

Finally, it has been discovered, with the use of the DNA's of the invention, that a necessary and sufficient condition, for activation of transcription of a gene (G) whose transcription is activated by hormones complexed with receptors, is the presence of the hormone and its receptor in the same cell as (G). This discovery has enabled us to provide improved compositions and methods for producing desired proteins in genetically engineered cells.

Two of these methods are methods of the present invention. The first is a method for inducing transcription of a gene whose transcription is activated by hormones complexed with the receptors. The second is a method for genetically engineering a cell and then increasing and controlling production of a protein coded for by a gene whose transcription is activated by hormones complexed with receptor proteins.

In discussing these two methods, a gene whose ranscription is activated by hormones complexed with receptor proteins will be referred to as gene (G). The hormone which activates gene (G) will be referred to as (H), and any of its analogs as (aH). The receptor protein will be referred to as (R), and functional modifications thereof as (r). Finally, the cell where gene (G) is located will be referred to as (C), and the protein coded for by gene (G) will be referred to as (P).

According to the gene induction method of the invention, cell (C), which contains gene (G), is transformed by a DNA of the invention, which is capable of being expressed in cell (C) and which codes for receptor (R) or a modified functional form (r) thereof; and the concentration of hormone (H), or analog (aH), in cell (C) is increased to a level at least sufficient to assure induction of expression of gene (G).

According to the method for engineering a cell and then producing protein (P): gene (G), which codes for protein (P), is placed in cell (C) so that it is under the control of a transcriptional control element to which hormone (H), when complexed with receptor (R), can bind, thereby inducing transcription of gene (G). Also according to this protein production method, both hormone (H) and receptor (R) are present in cell (C). The presence of receptor (R) is assured by transforming cell (C) with a DNA of the invention which codes for receptor (R), or a functional modified form (r) thereof. The presence of hormone (H), or its synthetic analog (aH) is assured by bathing transformed cell (C) in a bathing solution which contains hormone (H) or analog (aH). Then, according to the method, the transcription of gene (G) is controlled by controlling the concentration of (H) or (aH) in the bathing solution used to bath transformed cell (C). By so controlling the transcription of gene (G), it is possible to control the production of protein (P) in cell (C).

As those skilled in the art will appreciate, based on this teaching, it will now be possible to engineer cells so that production of a protein (P), encoded by a gene (G) whose transcription is activated by a hormone/receptor complex, is controlled by simply assuring the presence of hormone (H) and its receptor in cell (C) where gene (G) is located, and then controlling the concentration of hormone (H) or its analog that is present in cell (C).

DESCRIPTION OF THE INVENTION

The present invention relates, in part, to DNA segments which code for proteins having the hormone-binding and/or transcription-activating properties characteristic of glucocorticoid, mineralocorticoid and thyroid hormone receptors. According to this aspect of the invention, these DNA segments are ones capable of being expressed, in suitable host cells, thereby producing glucocorticoid, mineralocorticoid and thyroid hormone receptors or receptor-like proteins. The invention also relates to mRNA's produced as the result of transcription of the sense stands of the DNA's of the invention.

The DNA's of the invention are exemplified by DNA's referred to herein as: human glucocorticoid receptor DNA (hGR); human thyroid hormone receptor DNA's (hTR: hTR alpha and hTR beta; hTR alpha is exemplified by hERBA 8.7 and hFA 8; hTR beta is exemplified by cellular or "c-erb-A"); rat thyroid hormone receptor (rbeA12), which is the rat homolog of human thyroid receptor alpha; human mineralocorticoid receptor (hMR); and new human steroid hormone receptors (hERR1 and hERR2). The sense strand cDNA nucleotide sequences, and the predicted primary protein sequences coded for thereby, are shown in FIGS. 3-A–H for hGR; in FIGS. 21 and 22 for hMR.

DNA's hGR, human c-erb-A, hERBA 8.7, hFA8, hMR, hERR1, and hERR2 are preferred DNA's of the invention. Also preferred are the plasmids which carry these and other DNA's of the invention. Preferred plasmids include: pRShGR-alpha, pRShMR, peA101, rbeA12, GMCAT, pE4, pHKA, phERBA 8.7, phFA 8, and phH3.

In addition to pRShGR-alpha, preferred DNA's include modifications of pRShGR-alpha which are designated herein as I9, I37, I102, I120, I204, I214, I262, I289, I305, I346, I384, I403, I408, I422, I428, I440, I448, I490, I515, I532, I550, and I684, where "I" stands for "Insert", and the number following the "I" represents the DNA modification designation. Most preferred of the modified pRShGR DNA's are those which encode proteins having at least about 10% of the transcription-activating properties characteristic of human glucocorticoid receptor; those DNA's include I9, I37, I102, I120, I204, I214, I262, I289, I305, I346, I384, I403, I408, I422, I428, I440, I448, I490, I515, I532, I550, and I684.

Construction of pRShGR-alpha is detailed in the part of the specification labeled "Experimental Section II". (See especially subsection II. F. (b), "Recombinant Plasmids".) Experimental Section II also details construction and properties of the pRShGR-alpha modifications referred to in the preceding paragraph.

With regard to the cDNA sequence for hGR shown in FIG. 12, the two C's at the 5'-end of the indicated sequence are part of the KpnI site joining the indicated segment to the 3' end of the segment which includes the RSV-LTR, and the T at the 3'-end of the indicated sequence is a few bases 5' of the point where the indicated segment is joined to the segment which includes the SV40 polyadenylation signal.

pRShMR was constructed in essentially the same manner as pRShGR-alpha and is essentially the same as pRShGR-alpha. Stated another way, with the exception of minor modifications at the insertion sites, the hMR segment shown in FIGS. 21 and 22 replaces hGR, the sequence of which is shown in FIGS. 3A–H. Like pRShGR-alpha, pRShMR contains the receptor protein DNA coding sequence under the control of the promoter from Rous Sarcoma virus, plus the SV40 origin of replication. See Footnote 41 in the Reference portion of Experimental Section IV; also see FIG. 25; compare with FIG. 11.

With regard to the hMR sequence shown in FIGS. 21 and 22 A–E, the AG at the 5'-end of the segment is a few base pairs downstream of a HindIII site, whereby the hMR segment is joined to the RSV-LTR-containing segment. The AA at the 3'-end of the segment shown in FIGS. 21 and 22A–E is a few bases upstream of the 5'-end of the segment which includes the SV40 polyadenylation signal.

Turning now to plasmid GMCAT, it is a reporter plasmid that contains the MTV LTR linked to the bacterial gene for chloramphenicol acetyltransferase (CAT). As a result of this linkage, use of pGMCAT provides an enzymatic assay for assessing transcriptional activity of the MTV promoter. Since the MTV promoter contains several glucocorticoid response elements (GRE's), reporter plasmid pGMCAT can be cotransfected with expression plasmids carrying glucocorticoid or mineralocorticoid receptor DNA's, now known or later discovered, into suitable host cells. (Such cotransfection is part of the receptor "cis-trans" functionality bioassay system of the present invention. This aspect of the invention is discussed more fully below.) Detection of CAT activity in the co-transfected host cells shows that the polypeptides produced by the receptor expression plasmids are functional, i.e., have transcription activating properties characteristic of receptor proteins. Plasmid pGMCAT has been deposited with the ATCC for patent purposes; it has been accorded ATCC # 67282. (See FIGS. 28–30 for a schematic drawing of pGMCAT.)

Plasmid GHCAT is an example of another reporter plasmid which is useful in the present invention. pGHCAT contains a portion of the growth hormone promoter functionally linked to the bacterial gene for chloramphenicol acetyltransferase (CAT). Because of this linkage, use of pGHCAT provides an enzymatic assay for assessing transcriptional activity of the growth hormone (GH) promoter. Since the GH promoter contains a thyroid hormone response element (TRE), reporter plasmid pGHCAT can be cotransfected with expression plasmids carrying thyroid hormone receptor DNA's, now known or later discovered, into suitable host cells. (Such cotransfection is also part of the "cis-trans" receptor functional bioassay system of the present invention. This aspect of the invention is discussed more fully below.) When pGHCAT is used with a TR expression plasmid (which for example could carry hTR alpha or hTR beta DNA) to cotransfect suitable host cells, detection of CAT activity in the co-transfected host cells can be used to show that the polypeptides produced by the thyroid receptor (TR) expression plasmids are functional, i.e., have transcription activating properties characteristic of thyroid receptor proteins.

One of the added discoveries we have made employing the DNA's of the invention is the remarkable sequence homology among the various hormone receptors, within one species, and, for any particular receptor, among species. (See for example, FIG. 23A and B which compare the amino acid homology between mineralocorticoid receptor and glucocorticoid receptor; FIG. 33 which shows the amino acid comparisons between hGR, hMR, and hPR structures.) As a result of this homology the DNA's and RNA's of the invention can be used to probe for and isolate a gene from virtually any species coding for a hormone receptor which activates transcription by binding to chromatin DNA after completing with hormone. By so using the DNA's and RNA's of the invention, especially the preferred DNA's that have been deposited with the ATCC for patent purposes, those skilled in the art, without undue experimentation, can screen genomic libraries to find other glucocorticoid, mineralocorticoid and thyroid hormone receptors which fall within the scope of the present invention. This aspect of the invention is illustrated by our discovery of estrogen-related receptors hERR1 and hERR2, and rat thyroid receptor and human thyroid receptors TR alpha.

DNA's and sense strand RNA's of the invention can be employed, in conjunction with the induction and protein production methods of the invention for example, to make large quantities of substantially pure receptor proteins. In addition, the substantially pure receptor proteins thus produced can be employed, using well known techniques, in diagnostic assays to determine the presence of specific hormones in various body fluids and tissue samples.

Further, the receptor proteins of the invention can be employed in screening for receptor-agonists and receptor-antagonists by using binding assays such as the one discussed in Experimental Section III for binding $T_3$ to the receptor encoded by peA101, or in the "cis-trans" receptor functionality bioassay of the invention, which will be discussed below.

Finally, because the receptor proteins of the invention can be produced in substantially pure form they can be crystallized, and their structure can be determined by x-ray diffraction techniques. As will be apparent to those skilled in the art, such determinations are very useful when engineering "synthetic" or modified receptor protein analogs.

In addition to DNA's and RNA's, and the novel receptor proteins produced thereby, the present invention discloses three general methods: one relates to a bioassay for determining the functionality of receptor proteins; the other two relate methods for inducing and controlling expression of genes whose transcription is activated by a hormone-receptor complex bound to chromatin DNA. Each of the three general methods will be discussed separately.

The new bioassay system for testing receptor functionality, which we refer to as the "cis-trans" bioassay system, utilizes two plasmids: an "expression" plasmid and a "reporter" plasmid. According to the invention, the expression plasmid can be any plasmid capable of expressing a receptor DNA of the invention, or a mutant thereof, in a suitable receptor-negative host cell. Also according to the invention, the reporter plasmid can be any plasmid which contains an operative hormone responsive promoter/enhancer element, functionally linked to an operative reporter gene. (See the Definitions section of this Specification for an explanation of the terms used herein.) The plasmids pGMCAT arid pGHCAT are examples of reporter plasmids which contain an operative hormone responsive promoter/enhancer element functionally linked to an operative reporter gene, and can therefore be used in the receptor functionality bioassay of the invention. In pGMCAT, the operative hormone responsive promoter/enhancer element is the MTV LTR; in pGHCAT it is the functional portion of the growth hormone receptor. In both pGMCAT and GHCAT the operative reporter gene is the bacterial gene for chloramphenicol acetyltransferase (CAT).

In practicing the "cis-trans" receptor functionality bioassay of the invention, the expression plasmid and the reporter plasmid are cotransfected into suitable receptor-negative host cells. The transfected host cells are then cultured in the presence and absence of a hormone, or analog thereof, able to activate the hormone responsive promoter/enhancer element of the reporter plasmid. Next the transfected and cultured host cells are monitored for induction (i.e., the presence) of the product of the reporter gene sequence. Finally, according to the invention, the expression and/or steroid binding-capacity of the hormone receptor protein, or mutant thereof (coded for by the receptor DNA sequence on the expression plasmid and produced in the transfected and cultured host cells), is measured. (See FIG. 12 for a schematic drawing of this "cis-trans" bioassay system.)

When using the "cis-trans" receptor functionality bioassay system of the invention to determine the functionality of glucocorticoid or mineralocorticoid receptors, in preferred forms, plasmids will carry a selectable marker such as the amp gene. In addition, in preferred forms the reporter plasmids will have the MTV LTR or a functional portion of the growth hormone promoter as the hormone responsive promoter/enhancer element. MTV LTV is preferred because it is known that glucocorticoid hormones stimulate the rate of transcription of MTV DNA by increasing the efficiency of transcription initiation at a unique site within the MTV LTR. Moreover, glucocorticoid receptors bind specifically to DNA sequences mapped within the MTV LTR, and thus can confer glucocorticoid responsiveness to a heterologous promoter. (See Experimental Section II, especially subsection C. (a), Assay System and Experimental Design.) It is also known that mineralocorticoid receptor shows functional kinship with the glucocorticoid receptor, and that the DNA binding domain of hMR recognizes the MTV LTR. (See Experimental Section IV, especially subsection E.: Expression and Hormone Binding, and subsection F.: Transcriptional Activation). Growth hormone promoter is preferred because its activation is responsive to binding by the thyroid hormone-receptor complex.

Preferred host cells for use with the "cis-trans" bioassay system of the invention are COS cells and CV-1 cells. (See Experimental Section II, subsection C. (a) Assay System and Experimental Design, for use of the preferred host cells in the bioassay system of the present invention.) COS-1 (referred to as COS) cells are mouse kidney cells that express SV40 T antigen (Tag); CV-1 do not express SV40 Tag. CV-1 cell are convenient because they lack any endogenous glucocorticoid or mineralocorticoid or other known steroid or thyroid hormone receptors. Thus, via gene transfer with appropriate expression vectors, it is possible to convert these host cells from receptor negative to receptor positive. The presence of Tag in the COS-1 derivative lines allows the introduced expression plasmid to replicate and provides a relative increase in the amount of receptor produced during the assay period.

Expression plasmids containing the SV40 origin of replication (ori) can propagate to high copy number in any host cell which expresses SV40 Tag. Thus our expression plasmids carrying the SV40 "ori" can replicate in COS cells, but not in CV-1 cells. Although the increased expression afforded by high copy number is desired, it is not critical to the disclosed bioassay system. The use of any particular cell line as a "host" is also not critical. The expression vectors are so efficient that, in our hands, the assay has worked in all the hosts we have examined. CV-1 cells are preferred only because they are particularly convenient for gene transfer studies and provide a sensitive and well-described host cell system.

The "cis-trans" bioassay system is especially useful for determining whether a receptor DNA of the invention has been expressed in a transformed host cell; it is also useful in determining whether a receptor of the invention has at least about 10% of the binding activity of the corresponding naturally occurring cognate receptor, plus whether such a receptor has at least about 10% of the transcription-activating activity of the corresponding naturally occurring cognate receptor.

FIG. 12 schematically illustrates use of the of "cis-trans" receptor functionality bioassay system of the invention when used to determine the functionality of receptor polypeptides coded for by hGR cDNA. Details of the bioassay, and its effectiveness as a quantifiable bioassay system to test receptor functionality, are disclosed and discussed in Experimental Section II. (See especially, subsection F., Experimental Procedures, and subsection C., (b), Expression of Functional hGR.) As that experimental section shows, in addition to the CAT enzymatic assay, which can be used to show activation of the hormone responsive promoter/enhancer element, Western blot analysis of the transfected host cells can be used to demonstrate synthesis of receptor polypeptides which are indistinguishable with respect to mobility from the cognate receptors used as controls. Moreover, by using the "cis-trans" bioassay system of the invention, activation of the receptors (produced in the transfected and cultured host cells) by specific hormones can also be examined, as can their hormone-binding capabilities and characteristics. As Experimental Section II demonstrates, when this was done for hER, it was shown that the hGR of the invention is functional and binds with glucocorticoid hormones with the same specificity and concentrations as does the cognate receptor.

Finally, as stated in the Summary section, by using the DNA's of the invention we have discovered that a necessary and sufficient condition for activation of transcription of a gene (G), whose transcription is activated by hormones complexed with receptors, is the presence of the hormone and its receptor in the cell (C) where (G) is located. The method by which hormone (H) and receptor (R) effect gene G's transcription is not fully understood. However, it is believed that receptor (R), when complexed with hormone (H), binds to specific DNA sites, referred to in the art as "transcriptional control elements" or "DNA sequences which mediate transcriptional stimulation", which are located on the chromatin near where gene (G) is located. This binding by the hormone/receptor, or (H)/(R), complex seems to act in a way not yet understood, as a hormone dependent "switch" that "turns on", or in some other manner activates, the promoter for gene (G), and thus stimulates the transcription of the (G) gene.

Our discovery has enabled us to provide improved compositions and methods for producing desired proteins in genetically engineered cells. Two of these methods are methods of the present invention. The first is a method for inducing transcription of a gene whose transcription is activated by hormones complexed with the receptors. The second is a method for engineering a cell and then increasing and controlling production of a protein encoded by a gene whose transcription is activated by hormones complexed with receptor proteins.

Again, in discussing these two methods, a gene whose transcription is activated by hormones complexed with receptor proteins will be referred to as gene (G). The hormone which activates gene (G) will be referred to as (H), and any of its analogs as (aH). Receptor protein will be referred to as (R), and functional modifications thereof as (r). Finally, the cell where gene (G) is located will be referred to as (C), and the protein coded for by gene (G) will be referred to as (P).

According to the gene induction method of the invention, cell (C), which contains gene (G), is transformed by a DNA of the invention, which is capable of being expressed in cell (C) and which codes for receptor (R) or a modified functional form (r) thereof; arid the concentration of hormone (H), or analog (aH), in cell (C) is increased to a level at least sufficient to assure induction of expression of gene (G).

As we show in Experimental Section II, when we used the induction method of the invention, to our great surprise, the presence of (H) and (R) in the cell (C) where gene (G) was located not only induced transcription of gene (G) but also increased production of protein (P) 500–1000 fold. This finding showed us that the induction method can be used to not only induce transcription, but to increase and control it as well. This finding also led us to develop our method for engineering a cell and then controlling production proteins (P) coded for by genes (G) whose transcription is activated by hormones complexed with receptors. This method will be discussed more fully below.

Our induction method can also be used to increase and control production of protein (P) by simply adjusting the concentration of hormone (H), or analog (aH), available to cell (C). (As those skilled in the art will understand, by transforming cell (C) with a DNA of the invention, an adequate supply of (R) or (r) can be assured in cell (C) so that lack of (R) or (r) will no longer be a limiting factor in the transcription of gene (G). This being the case, by simply increasing the amount of (H) or (aH) in the culture solution, it will be possible to increase transcription of gene (G) and consequently the amount of protein (P) that is produced in (C) cells.)

The induction method of our invention can be used to induce expression of any gene (G) that is under transcriptional control of a transcriptional control element activated by binding of a steroid or thyroid hormone receptor complexed with one of its hormones (H), or analogs (aH) thereof, as long as: (1), a DNA is available which codes for receptor (R), or a functional modified form (r) thereof which has the transcription-activating properties of (R); (2), cell (C) is a cell that can be cultured; and (3), cell (C) can be transformed to express the (R)- or (r)-coding DNA needed to complex with hormone (H) or analog (aH).

Without undue experimentation those skilled in the art can use any of the deposited DNA's of the invention as probes to search genomic libraries for (R)- or (r)-coding DNA's which are not now available. Once found, these DNA's, if expressible in the cell (C) where gene (G) is located, can be used to transform (C) cells. Methods for transforming cultured cells are well known and can be used by those skilled in the art without undue experimentation. Also without undue experimentation, those skilled in the art can determine what the base level of (H) is in cell (C), if any is present, as well as what the concentration of (H) or (aH) must be in order to induce and control transcription of gene (G), and thus production of protein (P). The requisite concentrations of (H) can be supplied to transformed (C) cells by adding (H) or (aH) to the culture solutions used to bath cultured (C) cells.

We have taught that a necessary and sufficient condition for transcription of gene (G) is the presence of (H) or (aH) and (R) or (r) in the cell (C) where gene (G) is located, and that transcription of gene (G), and therefore production of protein (P), can be induced and controlled by simply increasing the amount of (H) or (aH) in the culture solutions used to bath transformed (C) cells. As those skilled in the art will appreciate, based on these teachings, it will now be possible to engineer cells so that production of a protein (P), encoded by a gene (G) whose transcription is activated by a hormone/receptor complex, is controlled by simply assuring the presence of hormone (H) and its receptor in cell (C) where gene (G) is located, and then controlling the concentration of hormone (H) or its analog that is present in cell (C). This concept is the basis for the cell engineering and protein production method of our invention.

According to our engineered cell and protein production method: (1), cell (C) is engineered to contain gene (G) so that transcription of gene (G) is under the control of a transcriptional control element to which an appropriate hormone/receptor, (H)/(R), complex can bind, thereby activating transcription of gene (G); (2), cell (C), which now contains gene (G) under the control of a transcriptional control element, is transformed by a DNA of the invention, which is capable of being expressed in cell (C) and which codes for receptor (R) or a modified functional form (r) thereof; and (3), finally the concentration of hormone (H), or analog thereof, in cell (C) is adjusted so that the transcription of gene (G) is not only induced but effectively increased and controlled by increasing controlling the amount of hormone (H) that is available to cell (C) from the culture solution used to bath transformed (C) cells. By so increasing and controlling gene (G)'s transcription, production of protein (P) is also increased and controlled.

As with the induction method, in our engineered cell and protein production method, both hormone (H) and receptor (R) are present in cell (C). Again, as with the induction method, the presence of receptor (R), or a functional modified form (r) thereof is assured by transforming cell (C) with a (R)- or (r)-coding DNA of the present invention. As stated above, methods for transforming cultured cells are well known and can be used by those skilled in the art without undue experimentation. The presence of (H), or its analog (aH), is assured, and the concentration of (H) or (aH) is controlled, by simply bathing transformed (C) cells in bathing solutions which contain appropriate concentrations of (H) or (aH). Appropriate concentration, i.e., concentrations of (H) or (aH) needed to for cell (C) to produce a given amount of protein (P) can be determined in a given situation by those skilled in the art, without undue experimentation.

Again, as those skilled in the art will understand, by transforming cell (C) with a DNA of the invention, an adequate supply of (R) or (r) can be assured in cell (C) so that lack of (R) or (r) will no longer be a limiting factor in the transcription of gene (G). This being the case, by simply increasing the amount of (H) or (aH) in the culture solution, it will be possible to increase the amount of protein (P) that is produced in (C) cells.

As was true with our induction method, the engineered cell and protein production method of our invention can be used to control expression of any gene (G) that can be inserted into cell (C) so that it is under transcriptional control of a transcriptional control element activated by binding of a steroid or thyroid hormone receptor (R) complexed with one of its hormones (H)), or analogs thereof, as long as: (1), a DNA is available which codes to receptor (R), or a functional modified form (r) thereof which has the transcription-activating properties of (R); (2), cell (C) is a cell that can be cultured; and (3), the (R)- or (r)-coding DNA is capable of being expressed in cell (C) where gene (G) is located.

Again, without undue experimentation, those skilled in the art can use any of the deposited DNA's of the invention as probes to search genomic libraries for (R)- or (r)-coding DNA sequences not now available. Once found, these DNA's, if expressible in cell (C) where gene (G) is located, can be used in the engineered protein production method of the present invention.

Also without undue experimentation, those skilled in the art can determine what the base level of (H) is in cell (C), if any is present, as well as what the concentration of (H) or (aH) must be in order to induce and control transcription of gene (G), and thus production of protein (P). The requisite concentration of (H) needed to assure the production of a desired amount of protein (P) can be supplied to transformed (C) cells by adding (H) or (aH) to the culture solutions used to bath cultured (C) cells.

Various aspects of the present invention are further explained and exemplified in the seven experimental sections which follow. Experimental Section I relates to human glucocorticoid receptor. More specifically, that section discloses the primary structure of hGR cDNA, as well its expression into a polypeptide which is functionally indistinguishable from previously disclosed hGR proteins. Experimental Section II relates to functional domains of hGR. As that section discloses, GR contains at least four functional domains, two of which were expected and correspond to the predicted DNA- and steroid-binding domains, and two of which were not expected, and have potent effects on transcription. Experimental Section III relates to human mineralocorticoid receptor, which we show has a structural and functional similarity to glucocorticoid receptor.

Without further elaboration, it is believed that one of ordinary skill in the art, can, using the preceding description, and the following Experimental sections, utilize the present invention to its fullest extent. The material disclosed in the experimental sections, unless otherwise indicated, is disclosed for illustrative purposes and therefore should not be construed as being limitive in any way of the appended claims.

EXPERIMENTAL SECTION I

Primary Structure and Expression of a Functional Human Glucocorticoid Receptor cDNA

I. A. Summary

Here we report the complete amino-acid sequence of the human glucocorticoid receptor (hGR), deduced from human lymphoid and fibroblast cDNA clones. The sequence reveals various structural features of the receptor, including the major immunogenic domain and a cysteine/arginine/lysine-rich region which may constitute a portion of the DNA-binding domain. We describe the use of the SP6 transcription vector system to generate analytical amounts of full-length protein, and demonstrate that the cell-free translated protein is both immunoreactive and possesses steroid-binding properties characteristic of the native glucocorticoid receptor. Weinberger, et al., (1985b) describes the homology of the hGR sequence to that of the oncogene v-erb-A.

I. B. Introduction

The glucocorticoid receptor is widely distributed and expressed in many cultured cell lines, and the control of gene expression by glucocorticoids, therefore, has been widely studied as a model for transcriptional regulation. A number of glucocorticoid-responsive transcription units, including mouse mammary tumor virus (MMTV) (Ringold, et al., 1975; Parks, et al., 1974), mouse and human metallothionein (Eager, et al., 1981; Karin, et al., 1980), rat alpha$_{2M}$-globulin (Kurtz, et al., 1977) and rat and human growth hormone (Spindler, et al., 1982; Evans, et al., 1982; Robins, et al., 1982) genes have been identified. DNA sequences mediating transcriptional stimulation of several of these genes have been localized. For MMTV, these sequences are discrete genomic regions upstream of the transcriptional start site which appear to exert their actions independently of orientation and position (Chandler, et al., 1983; Ostrowski, et al., 1984). The steroid/receptor complex appears to bind to these regulatory sequences and purified receptor has been used to define the specific binding sites (Govinda, et al., 1982; Scheidereit, et al., 1983; Pfahl, 1982; Payvar, et al., 1983). Based on the footprinting analyses of several responsive genes, a consensus DNA binding sequence sharing the core sequence 5' TGT/CTCT 3' has been proposed (Karin, et al., 1984).

The ability of the glucocorticoid-responsive element (GRE) to alter its position and orientation yet still maintain promoter inducibility suggests that it resembles the class of cis-acting regulatory sequences termed enhancers (Chandler, et al., 1983). First discovered in viruses and subsequently in cellular genes, these sequences are necessary for efficient transcription in vivo (Laimonis, et al., 1982; Benoist, et al., 1981; Baerji, et al., 1983). It has been suggested that enhancers are recognized by trans-acting factors that mediate regulatory effects by tissue-specific transcriptional control. Although the enhancer factors have not been well characterized, the glucocorticoid receptor may serve as a paradigm for these putative gene activator proteins.

The availability of radiolabeled high-affinity glucocorticoid analogues such as dexamethasone and triamcinolone acetonide has led to the development of purification strategies resulting in the isolation of nearly pure rat and human receptors (Simons, et al., 1981; Gehring, et al., 1983). Although the receptor migrates as a dimer in sucrose gradients, analysis on denaturing SDS-polyacrylamide gels detects a single polypeptide of relative molecular mass ($M_r$) ~94,000 (94K) (Westpahl, et al., 1982; Wrange, et al., 1979).

The native polypeptide contains intrinsic specificity for steroid binding and DNA sequence recognition. By using as probes monoclonal and polyclonal antibodies raised against the purified rat and human receptors (Okret, et al., 1981; Harmon, et al., 1984; Gametchu, et al., 1984), it has been possible to identify a major immunogenic region in the receptor residing on a portion of the molecule that is distinct from the steroid- and DNA-binding regions (Carlstedt-Duke, et al., 1982; Wrange, et al., 1984; Dellweg, et al., 1982). To gain further information about the structure of this molecule and to begin an analysis of the molecular mechanisms by which it regulates gene transcription, we set out to clone receptor cDNA sequences. By using receptor-specific antibodies as probes, we and others have isolated clones containing human or rat glucocorticoid receptor cDNA inserts (Weinberger, et al., 1985a; Miesfeld, et al., 1984).

I. C. Results (a) Glucocorticoid Receptor cDNA

A library of cDNA clones was constructed in the phage expression vector lambda gt11 using poly(A)$^+$ RNA from the human lymphoid cell line IM-9 as template, as described previously (Weinberger, et al., 1985a). This library was initially screened with a rabbit polyclonal antiserum to the purified glucocorticoid receptor, resulting in the isolation of several immunopositive candidate clones from ~$2.5\times10^5$ plaques. The beta-galactosidase fusion proteins generated from these clones were used to affinity-purify receptor epitope-specific antibody, which was subsequently recovered and identified by binding to protein blots of cellular extracts. Three clones containing inserts expressing antigenic determinants of the human glucocorticoid receptor were isolated. The inserts of these clones, although of different sizes, cross-hybridized, indicating that they contained a common sequence which presumably delimits the major immunogenic domain of the receptor. Together, these clones spanned 1.4 kilobase pairs (kbp) but were clearly not long enough to code for the entire receptor, which was estimated to require ~2,500 nucleotides to encode a polypeptide of $M_r$ 94K.

To isolate additional cDNA clones we again screened the original library and also examined a second library (given by E. Okayama) prepared with poly(A)$^+$ RNA from human fibroblasts in the vector described by Okayama and Berg (1983). Using one of the immunopositive cDNA inserts (hGR1.2) as probe, 12 clones were isolated that, together, covered more than 4.0 kbp. The nucleotide sequences of these clones were determined by the procedure of Maxam and Gilbert (1977) according to the strategy indicated in FIG. 1. RNA blot analysis indicated that a cDNA insert of 5–7 kilobases (kb) would be necessary to obtain a full-length clone and sequence analysis indicated that the overlapping clones OB7 and hGR5.16 spanned an open reading frame of 720 amino acids, not large enough to encode the complete receptor. Therefore, a second human fibroblast cDNA library of ~$2\times10^6$ transformants was screened, yielding a clone (OB10) containing a large insert that extended 150 base pairs (bp) upstream of the putative translation initiation site (see FIGS. 1 and 2). Sequence analysis predicts two protein forms, termed alpha and beta, which diverge at amino acid 727 and contain additional distinct open reading frames of 50 and 15 amino acids, respectively, at their carboxy termini (see FIG. 2). The alpha form, represented by clone OB7, is the predominant form of glucocorticoid receptor because eight cDNA clones isolated from various libraries contain this sequence.

(b) cDNA and Protein Sequences

FIGS. 3A–H show the 4,800-nucleotide sequence encoding the human alpha glucocorticoid receptor, determined using clones hGR1.2, hGR5.16, OB7 and OB10. The translation initiation site was assigned to the methionine codon corresponding to nucleotides 133–135 because this is the first ATG triplet that appears downstream from the in-frame terminator TGA (nucleotides 121–123). However, in the absence of amino-terminal peptide sequence information, unequivocal determination of the initiation site is not yet possible. The codon specifying the lysine at position 777 is followed by the translation termination codon TGA. The remainder of the coding sequence is covered by multiple overlapping clones, with OB7 containing a 4.3-kb insert that continues to the poly(A) addition site and OB10 containing the putative initiator methionine. The 3' regions of clones OB7 and OB10 diverge at nucleotide 2,314, as shown by both restriction endonuclease and DNA sequence analysis. At this junction, the alpha-receptor continues with a unique sequence encoding an additional 50 amino acids whereas the beta-receptor continues for only 15 additional amino acids (FIGS. 4 and 5). The 3'-untranslated region of OB7 is 2,325 nucleotides long, while that of OB10 is 1,433 nucleotides. There is no significant homology between these two regions, as indicated by direct sequence comparison (FIGS. 3A–H, 4 and 5) or by hybridization analysis under stringent conditions (data not shown).

In addition, we have isolated from a human primary fibroblast library another cDNA clone, OB12 (data not shown), which contains sequences identical to OB7 but uses the polyadenylation signal at nucleotide 3,101 (FIGS. 2 and 3A–H), giving rise to a shorter 3'-untranslated region. Use of probes specific for the 3'-untranslated region of OB7 to screen a human placenta cDNA library reveals that most clones terminate at the first poly(A) site in OB7. Thus, messenger RNA variation is the apparent consequence of both alternative polyadenylation and alternative RNA splicing (see below). The fact that the human fibroblast library contained both cDNA's suggests that both receptor forms may be present in the same cell.

(c) Analysis of Alpha- and Beta-Receptor Protein

Sequence analysis reveals that the alpha and beta forms of the human glucocorticoid receptor are 777 and 742 residues long, respectively; the two forms are identical up to residue 727, after which they diverge. To examine the receptor levels in vivo, cytoplasmic extracts from several human and mouse cell lines were probed by immunoblot analysis with a polyclonal antibody directed against the human glucocorticoid receptor (Harmon, 1984). Alpha- and beta-receptor cDNA's were inserted into the SP6 transcription vector to create synthetic mRNA for in vitro translation (FIG. 6). The RNA's were separately added to a rabbit reticulocyte lysate system and the unlabeled products analyzed by SDS-polyacrylamide gel electrophoresis (SDS-PAGE). The two RNA's program the synthesis of distinct translation products whose migration differences are consistent with the predicted polypeptide lengths of the two forms (FIG. 7, lanes 2, 3). Cytoplasmic extracts from untreated IM-9 cells and IM-9 cells treated with 1 microM triamcinolone acetonide serve as markers (FIG. 7, lanes 4,5) for the 94K receptor (the 79K form represents a putative receptor degradation product) (Wrange, et al., 1984). Note that after steroid treatment, the intensity of the 94K band is reduced, corresponding to tighter receptor/chromatin binding and, therefore, receptor translocation to the nucleus. The alpha form co-migrates with the 94K band of the negative receptor while the beta form migrates more rapidly (see FIG. 7, compare lanes 2,3 with lanes 4,5). A comparison of cytoplasmic extracts from various human and mouse cell lines reveals the presence of only the alpha-receptor (see FIG. 7, lanes 6–9). Interestingly, the mouse ADR6 lymphoma cell line (Danielsen, et al., 1984), selected for resistance to steroid-induced lysis, contains no steroid-binding activity and shows no immunoreactive receptor (see FIG. 7, lane 7). Therefore, based on characterization of multiple receptor cDNA clones and receptor protein by immunoblot analysis, we conclude that the predominant physiological form of the glucocorticoid receptor is the alpha (94K) species.

(d) Expression of hGR In Vitro

To provide additional evidence that the cloned receptor is functional, we investigated the possibility that the in vitro-translated products might be able to selectively bind corticosteroids. Accordingly, the rabbit reticulocyte lysate was incubated with the radiolabeled synthetic glucocorticoid analogue $^3$-triamcinolone acetonide ($^3$H-TA) before or after addition of in vitro-synthesized alpha or beta hGR RNA. As shown in FIG. 8, those lysates programmed with alpha-hGR RNA acquired selective steroid-binding capacity; unexpectedly, the beta-receptor synthesized in vitro failed to bind competable $^3$H-TA. The in vitro-synthesized alpha-hGR bound radiolabeled steroid which could be competed with by addition of excess unlabeled cortisol or dexamethasone; however, binding of $^3$H-TA was not effectively competed with by addition of excess unlabeled oestrogen or testosterone. In contrast, excess progesterone constituted an effective competitor, consistent with the previously reported anti-glucocorticoid activities of progesterone (Rousseau, et al., 1972). To confirm these results, the competition experiments were repeated with native glucocorticoid receptor prepared from extracts of human lymphoid cells. Both the in vitro-translated receptor and the natural in vivo receptor have nearly identical properties with regard to steroid binding and competition with excess unlabeled steroid analogue (see FIG. 8).

(e) hGR Sequences Map to at Least Two Genes

The human glucocorticoid receptor gene has been functionally mapped to chromosome 5. Analysis of somatic cell hybrids constructed by fusing receptor-deficient mouse T cells (EL4) with human receptor-containing T cells (CEM-C7) indicated that segregants expressing the wild-type CEM-C7 receptor maintained human chromosome 5 while dexamethasone-resistant segregants had lost this chromosome (Gehring, et al., 1985).

To confirm the authenticity of our cDNA clones, we mapped receptor cDNA sequences using Chinese hamster/human somatic cell hybrids containing only human chromosome 5 (HHW454). DNA's extracted from human placenta, HHW454 hybrid cells and Chinese hamster ovary (CHO) cells were digested with EcoRI or HindIII restriction endonucleases and separated on a 0.8% agarose gel. DNA fragments transferred to nitrocellulose were probed with a portion of the receptor-coding region derived from nucleotides 570–1,640 (See hGR1.2A in FIG. 1). In addition to CHO-specific EcoRI bands of 6.8 and 17 kbp, DNA from the hybrid cell line also contains human-specific bands of 3.0 and 5.0 kbp (see FIG. 6*a*, lanes 2, 3 of Hollenberg, et al., 1985). (The study disclosed herein as Experimental Section I was published as Hollenberg, et al., 1985. FIGS. 6 and 7 appear in the paper but not in the present specification.) Unexpectedly, a DNA fragment of 9.5 kbp is found in total human DNA but not in the hybrid line (see Hollenberg, et al., 1985, FIG. 6*a*, lane 1). Similarly, HindIII digestion revealed a 7.5 bkp band that is not present in the chromosome 5 hybrid cell DNA (see Hollenberg, et al., 1985, FIG. 6*a*, lane 4). These results indicate that the receptor cDNA maps to human chromosome 5, but that there are additional receptor-related sequences elsewhere in the genome. To map these sequences, we used a dual-laser fluorescence-activated cell sorter (FACS) to sort mitotic chromosome suspensions stained with DIPI/chromomycin in conjunction with Hoechst 33258 chromomycin; this technique allows separation of the 24 human chromosome types into 22 fractions (Lebo, et al., 1984). After the chromosomes were sorted directly onto nitrocellulose, the chromosomal DNA was denatured and hybridized to the hGR cDNA probe. In addition to confirming the chromosome 5 localization, additional sequences were found on chromosome 16 (see Hollenberg, et al., 1985, FIG. 6*b*). To confirm this localization, DNA's from mouse erythroleukaemia cells and a mouse erythroleukaemia cell line containing human chromosome 16 (see Bode, et al., 1981) were digested with HindIII and probed with hGR cDNA (see Hollenberg, et al., 1985, FIG. 6*c*); as predicted, the only DNA fragment found in the hybrid and not in the control was the 7.5-kbp DNA fragment, thus establishing the chromosome 16 assignment (see Hollenberg, et al., FIG. 6*c*, lanes 1, 2).

Additional Southern blot analyses using the EcoRI-XbaI fragments from OB7 and OB10 3'-untranslated regions revealed hybridization only to chromosome 5 (data not shown). We conclude that both the alpha- and beta-receptor cDNA's are probably encoded by a single gene on chromosome 5 and suggest that the two cDNA forms are generated by alternative splicing. In addition, we conclude that another gene residing on human chromosome 16 contains homology to the glucocorticoid receptor gene, at least between nucleotides 570 and 1,640. It is not clear whether these sequences on chromosome 16 represent a related steroid receptor gene, a processed gene or pseudogene, or a gene that shares a common domain with the gene for the glucocorticoid receptor. Genomic cloning and DNA sequencing may provide the answer.

To determine the size of the mRNA encoding the glucorcorticoid receptor, Northern blot hybridization (Bode, et al., 1981) experiments were performed using cytoplasmic mRNA isolated from a human fibroblast cell line, HT1080. Using the hGR1.2 coding sequence as probe, multiple mRNA's of 5.6, 6.1 and 7.1 kb were detected. Treatment of these cells with glucocorticoids for 24 h leads to a 2–3-fold reduction in receptor mRNA's, suggesting a potential negative feedback regulation.

I. D. Discussion

Structural analysis of the glucocorticoid receptor is a prerequisite for gaining insight into the mechanisms by which this regulatory molecule exerts its effects on gene transcription. Here, we have presented the primary sequence of the human glucocorticoid receptor deduced from nucleotide sequence analysis of cDNA clones.

Isolation of hGR cDNA's has revealed the existence of multiple mRNA's encoding at least two forms of the polypeptide. The predicted proteins differ at their carboxy termini by the substitution of 50 amino acids in the case of alpha-hGR and 15 amino acids in the case of beta-hGR. The alpha glucocorticoid receptor is the major form identified in several human cell lines and cDNA libraries. However, a recent report by Northrop, et al. (1985) characterizes two forms of the receptor in mouse lymphoid cells. The relationship of alpha- and beta-hGR to the mouse doublet species remains to be established. Also, the cellular distribution and potential function of beta-hGR are unclear, although it is possible that variant receptors are used for tissue-specific functions. We are now generating antisera to synthetic peptides specific for each human receptor form to elucidate their tissue-specific expression.

Among the cDNA's selected using the immunopositive phage DNA insert hGR1.2A as a probe were those containing 3' ends similar to OB7, except that polyadenylation was signaled earlier by the use of an AATAAA at nucleotide 3,101. These clones have been isolated from both human fibroblast and placental libraries (data not shown). Alternative poly(A) site selection is a feature of many eukaryotic transcription units (Darnell, 1982). In some instances, selection of poly(A) sites specifies particular polypeptide products (Amara, et al., 1982; Rosenfeld, et al., 1983; Alt, et al., 1980; Schwarzbauer, et al., 1983) while in other cases, alternative poly(A) site selection produces no change in the primary structure of the polypeptide (Setzer, et al., 1982) while in other cases, alternative poly(A) site selection produces no change in the primary structure of the polypeptide (Setzer, et al., 1982). The selection of poly(A) sites during receptor transcription may (1) alter the stability of the mRNA in a particular tissue, (2) lead to splicing changes, or (3) be random, with no physiological consequence.

The in vitro translated studies described here provide direct evidence that the cloned molecule encodes the complete glucocorticoid receptor. First, the in vitro-translated product is identical in size to the native glucocorticoid receptor and is immunologically reactive with receptor-specific antiserum. Second, the in vitro-translated protein acts functionally as a glucocorticoid receptor in that it is capable of selectively binding the synthetic glucocorticoid triamcinolone acetonide. This binding is specifically competed with by glucocorticoids, glucocorticoid analogues and progesterone but is not competed with by the sex steroids testosterone and oestrogen. In this respect, the in vitro-translated receptor behaves identically to the in vivo receptor from human lymphoid cells, providing the first evidence of a function for the cloned molecule. The acquisition of steroid-binding properties does not appear to require any specific modifications or, if it does, these modifications can occur in the in vitro translation mix.

The results presented here provide the information necessary for studying the molecular interactions of a eukaryotic transcriptional regulatory protein with its target genes. These structural studies provide a basis from which the glucocorticoid receptor, its gene, and its RNA products can be analyzed. Furthermore, the ability to express receptor in vitro provides a novel means by which the consequence of specific in vitro mutagenesis can be rapidly tested. Finally, the isolation of genes responsive to glucocorticoids and specific regulatory elements by both mutagenic and protein-binding studies suggests that this protein can serve as a very useful model for analysis of inducible eukaryotic gene regulation.

I. E. Detailed Description of Figures Referred to in Experimental Section I

FIGS. 1 and 2.

Human glucocorticoid receptor cDNA sequencing strategy and schematic representation of cDNA clones. FIG. 1, the composite cDNA for the alpha glucocorticoid receptor is represented at the top, with noncoding (lines) and coding (stippled portion) sequences indicated. Common 6-nucleotide restriction enzyme sites are shown. Overlapping cDNA inserts used to determine the sequence are shown: arrows beneath the regions sequenced show the direction and extent of sequencing. The dashed line at the 3' end of OB10 indicates divergent sequence. Numbers refer to nucleotide positions in OB10 relative to the 5'-most transcribed sequence. FIG. 2, cDNA's encoding the alpha and beta forms of the receptor (OB7 and OB10, respectively). The 5' end of OB7 (broken lines) is contributed by the OB10 clone. Protein-coding information is represented by wide bars; untranslated sequences are indicated by thin bars. Nucleotides and amino acids are numbered above and below the coding sequence, respectively. Common DNA sequences extend to nucleotide 2,313 (amino-acid residue 727), at which point the alpha- and beta-receptor forms diverge, with the alpha cDNA's (OB12, OB7) continuing in an open reading frame for 150 nucleotides (50 amino acids) and the beta cDNA (OB10) continuing for 45 nucleotides (1.5 amino acids; see FIGS. 4 and 5). Hexanucleotide signals (AATAAA) just upstream of the poly(A) in the clones are indicated, with the first hexanucleotide in OB7 serving as poly(A) in OB12.

FIGS. 1 and 2 Methods

The inserts hGR1.2, hGR2.9 and hGR5.16 were isolated from a lambda gt11 IM-9 lymphoid cell cDNA library as described previously (Weinberger, et al., 1985). Two clones were isolated from cDNA libraries constructed by H. Okayama in pcD (Okayama, et al., 1983) using poly(A)$^+$ mRNA from GM637 human fibroblasts (OB7) and primary human fibroblasts (OB10). Screening was performed with the hGR1.2-cDNA, radiolabeled by nick-translation with $^{32}$P-dCTP. Sequences were determined by the chemical cleavage method of Maxam and Gilbert (1977).

FIGS. 3A–H.

cDNA and predicted protein sequence of human glucocorticoid receptor. The complete alpha coding sequence and OB7 3'-untranslated region are shown, with the deduced amino acids given above the long open reading frame. An upstream in-frame stop codon at nucleotides 121–123 and putative additional polyadenylation signals in OB7 are underlined.

FIGS. 4 and 5.

Restriction map and nucleotide sequence of the 3' end of the human glucocorticoid receptor beta cDNA. FIG. 4, The common 6-nucleotide restriction enzyme sites are shown for the 3'-untranslated region of OB10. FIG. 5, The cDNA sequence of the beta form (OB10) from nucleotide 2,281 to 3,820 compared with the protein-coding information found in the 3'-terminal coding portion of the alpha form (OB7). Amino acids encoded by each of the cDNA's are presented above the nucleotide sequences. Putative polyadenylation signals (AATAAA) in the 3'-untranslated sequence of OB10 are underlined.

FIGS. 6 and 7.

Immunoblot comparison of hGR translated in vitro with in vivo hGR from cell extracts. FIG. 6, The vectors constructed for in vitro transcription of the hGR cDNA sequence. The complete alpha (pGR107) and beta (pGR108) coding sequences were placed under the transcriptional control of the SP6 promoter in pGEM1. Vector sequences, noncoding cDNA sequences and coding sequences are indicated by thin lines, thick bars and boxed regions, respectively. The poly(A) tract of ~60 nucleotides is indicated by $A_{pi}$. Divergent coding sequences are indicated by striped and stippled regions. FIG. 7, Western blot analysis of in vitro translation products and cell extracts. Unlabeled translation products synthesized in a rabbit reticulocyte lysate system with no added RNA (lane 1) or with RNA synthesized from pGR108 (beta, lane 2) or pGR107 (alpha, lane 3) were fractionated on a 7.5% SDS-polyacrylamide gel. Additional lanes are: cytoplasmic extracts from IM-9 (lane 4), IM-9 treated with 1 microM triamcinolone acetonide (lane 5), HeLa (lane 6), ADR6.M1890.AD1 mouse lymphoma (lane 7), S49 mouse lymphoma (lane 8) and EL4 lymphoma (lane 9). Proteins were transferred to nitrocellulose and probed with anti-hGR antibody, followed by $^{125}$I-labeled *Staphylococcus aureus* protein A as described previously (Weinberger, et al., 1985).

FIGS. 6 and 7 Methods.

To construct an expression vector containing the entire alpha coding sequence shown in FIGS. 3A–H, the 3' coding sequence of OB7 was fused to OB10 5' coding information. OB7 was partially digested with EcoRI, completely digested with XbaI, and the 1.20-kbp fragment was gel-purified and ligated with EcoRI/XbaI-digested OB10 to produce the intermediate pOB107. The entire pOB107 cDNA sequence including the 5' poly(G) tract (11 nucleotides, nt) and 3' poly(A) tract (~60 nt) was excised by partial PstI/complete BamHI digestion. The resultant 3.5-kb fragment was gel-purified and inserted between the PstI and BamHI sites of pGEM1 (Promega Biotec) to yield pGR107. Plasmid pGR108 was directly constructed from pOB10 by partial PstI/complete BamHI digestion and insertion of the resulting cDNA insert into the corresponding sites of pGEM1. Capped SP6 transcripts were synthesized from PvuII-linearized pGR107 and pGR108, as described by Krieg and Melton (1984), with simultaneous capping effected by reduction of the GTP concentration from 400 to 100 microM and addition of $m^7$ GppG (Pharmacia) to 500 microM. Transcripts were purified by P60 chromatography and translated with micrococcal nuclease-treated rabbit reticulocyte lysate (Promega Biotec) in conditions suggested by the manufacturer. Preparation of IM-9 cytosol from steroid-treated cells was as described previously (Weinberger, et al., 1985). Size markers are phosphorylase B (97K), bovine serum albumin (66K) and ovalbumin (45K).

FIG. 8.

Steroid-binding of alpha-hGR translated in vitro. Binding to IM-9 cytosol extract (stippled bars) and to reticulocyte lysate containing SP6-generated alpha-hGR RNA (GR107; open bars) are shown. Bars represent bound $^3$H-triamcinolone acetonide (TA) determined with a 100-fold excess of various steroid competitors; 100% competition was determined using unlabeled TA as competitor. The values represent the mean of triplicate determinations, with error bars showing $P<0.05$. Steroid competitors are dexamethasone (Dex), cortisol (Cort), progesterone (Prog), testosterone (Test), and oestradiol (Oest).

FIG. 8 Methods.

Binding assays were performed in 100 microliters containing 10 mM Tris-HCl pH 7.4, 100 mM NaCl, 1 mM EDTA, 10 mM sodium molybdate, 10 dithiothreitol, 150 mM $^3$H-TA (20 Ci mmol$^{-1}$; Amersham) and 10 microliters translation mixture or 100 microgram fresh 1M-9 cytosol. Unlabeled steroid competitor (15 microM) was added as indicated. After 2 h at 0° C., samples were extracted twice for 5 min. each with 5 microliter of 50% dextran-coated charcoal to remove unbound steroid, and counted. Uncompeted and fully competed values for the alpha glucocorticoid receptor (GR107) were 490 and 290 c.p.m., respectively. Reticulocyte lysate translation mixtures without added transcript or programmed with beta-receptor SP6 RNA (GR108) contained no competable $^3$H-TA binding.

Additional Figures.

The scientific study presented here as Experimental Section I was published in *Nature,* 318:635–641 (1985). The *Nature* publication contain two Figures which are not included in this Experimental section. Those figures are: FIG. 6, Chromosome mapping analysis of hGR cDNA; FIG. 7, Northern blot analysis of hGR cDNA.

EXPERIMENTAL SECTION II

Functional Domains of the Human Glucocorticoid Receptor

II. A. Summary

Human glucocorticoid receptor (hGR) produced in CV-1 cells via transfection of an hGR expression vector functions as a necessary and sufficient factor for the transcriptional activation of the MTV-CAT fusion gene. The magnitude of the induction (500–1000 fold) reveals that the hGR may act as a transcriptional "switch", converting a silent promoter containing a glucocorticoid response element to an activated state. Stimulation of transcription of the MTV-CAT gene fusion by hGR is not dependent on transcriptional factors that are limiting in CV-1 cells. Characterization of 27 insertional mutants of the hGR allowed the location of at least four functional domains, two of which correspond to the predicted DNA- and steroid-binding domains. The other two domains are referred to as tau for their potent effects on transcription. This raises the possibility that other regions in the receptor are necessary for full transcriptional activation but are not specifically involved in steroid or DNA binding.

II. B. Introduction

The primary structure of two classes of steroid hormone receptors have been elucidated by cloning and sequencing of their cDNA. As Experimental Section I discloses, identification of cDNA's encoding the human glucocorticoid receptor (hGR) revealed two forms of the protein, of 777 (alpha) and 742 (beta) amino acids, which differ at their carboxyl termini. (The Experimental Section I disclosure has been published as Hollenberg, et al., 1985.) The human estrogen receptor is a somewhat smaller protein of 595 amino acids (Greene, et al., 1986; Green, et al., 1986). Amino acid sequence comparisons revealed extensive regions of homology not only between the two classes of receptors but also with the v-erb-A oncogene product of avian erythroblastosis virus (Weinberger, et al., 1985; Greene, et al., 1986; Green, et al., 1986). This supports the suggestion that steroid receptor genes and the c-erb-A proto-oncogene are derived from a common primordial ancestral regulatory gene (Weinberger, et al., 1985).

On the basis of the amino acid sequence of hGR deduced from the cloned cDNA (see Experimental Section I), the locations of functionally and immunologically important regions of the protein have been proposed (Weinberger, et al., 1985). These include an immunological domain located in the amino-terminal half of the protein, a DNA-binding domain that shows structural similarities with other DNA-binding proteins, and the glucocorticoid-binding site localized near the carboxyl terminus of the molecule. However, the location of each domain is tentative, and no domain involved in the activation of transcription itself has been identified. In this study, we sought to confirm the proposed sites of the functional domains within the hGR and to find other regions of importance by introducing amino acid alterations in the hGR protein. We first developed a novel expression system in monkey kidney cells in which the synthesis of functional hGR is directed by the transcription of the cDNA under the control of the long terminal repeat (LTR) of the Rous sarcoma virus (RSV). The functions of the synthesized receptor were monitored by the induction of transcription of the mouse mammary tumor virus (MTV) LTR as measured by chloramphenicol acetyltransferase (CAT) assays (Gorman, et al., 1982a) and steroid hormone binding. This new expression system allowed us to investigate the effect of insertional mutagenesis on the various functions of the receptor, which led us to propose a more detailed model of the domain structure of the hGR. Our results, based on the analysis of 27 insertional mutations, confirm the notion that the glucocorticoid receptor is composed of discrete functional domains (Weinberger, et al., 1985). In addition, they identify additional sequences outside the proposed DNA- and steroid-binding domains, which, as stated above, we refer to as tau for their potent effects on transcription.

II. C. Results a) Assay System and Experimental Design

The assay system and strategy used to study the expression of functional hGR from the cloned cDNA (See Experimental Section I) is shown in FIG. 11. In these experiments, a glucocorticoid-responsive promoter/enhancer element linked to a reporter gene was introduced into a receptor-negative cell. Thus, in principle, this construction should be transcriptionally inactive. For our assay, we chose to use the MTV LTR fused to the sequence coding for chloramphenicol acetyltransferase (CAT) (EC2.3.1.28). It has been demonstrated previously that glucocorticoid hormones stimulate the rate of transcription of MTV DNA (Ringold, et al., 1977) by increasing the efficiency of transcription initiation at a unique site within the MTV LTR (Ucker, et al., 1983). Moreover, glucocorticoid receptors bind specifically to DNA sequences mapped within the MTV LTR (Payvar, et al., 1983), which can confer glucocorticoid responsiveness to a heterologous promoter (Chandler, et al., 1983). Cotransfection of pMTVCAT (or pGMCAT) with a receptor expression plasmid provides functional receptors that allow induction of CAT activity upon treatment of the transfected cells with glucocorticoid hormone. In addition, biochemical studies such as steroid binding activity and Western blot analysis of the expressed receptors can be performed simultaneously.

The expression vector linking the RSV LTR to full length hGR cDNA (pRShGR alpha) was designed to obtain high levels of expression in a wide range of host cell types. The vector pRShGR alpha is a derivative of pRSVCAT (Gorman, et al., 1982b) in which the coding sequence of the CAT gene was replaced by the hGR cDNA. The origin of replication of SV40 was introduced into the vector to allow the recombinant plasmid to propagate to high copy numbers in COS-1 (referred to as COS) monkey kidney cells that express T antigen (Tag) (Gluzman, 1981). COS cells and parental cell line CV-1 offer the additional advantage of having undetectable levels of glucocorticoid receptors (unpublished observation and FIGS. 12 and 13).

(b) Expression of Functional hGR

The above assay was designed to overcome some of the major difficulties encountered in studying the mechanisms of action of steroid hormone receptors. These difficulties include low intracellular levels of receptor, possible heterogeneity of receptors, and lack of a quantifiable bioassay system to test receptor functions. Accordingly, we first looked at the relative amount of hGR that could be made by COS cells transfected with pRShGR alpha. FIG. 12 (right lane), a Western blot analysis of transfected COS cells, demonstrates that COS cells synthesized an hGR polypeptide of 94 kd that is indistinguishable with respect to mobility from the hGR present in the IM9 cell line (left lane). Moreover, the amount of hGR present in transiently transfected COS cells is greater than the level found in IM9 cells, which contain between 100,000–200,000 receptors per cell (Harmon, et al., 1984). This expression system not only provides us with cells carrying high intracellular levels of hGR, but eliminates the possibility of receptor microheterogeneity, which could interfere in the functional study of hGR.

To test the functional capability of the expressed hGR as a positive transcriptional factor, we performed CAT assays with cell extracts obtained after cotransfection with pMTV-CAT and pRShGR alpha. Transfection into both COS and the parental CV-1 cells was examined. As expected (Alwine, 1985), the presence of SV40 Tag in COS cells increased basal activity of the MTV LTR (data not shown). Thus, CV-1 cells, which do not express the SV40 Tag, were used to achieve maximal induction. As shown in FIG. 13, cotransfection of pMTVCAT with a control plasmid does not generate CAT activity in CV-1 cells. Similarly, cotransfection of pMTVCAT and pRShGR alpha does not produce any CAT activity. However, treatment of the same cotransfected CV-1 cells with dexamethasone (DEX) turns on the transcription of the MTV-CAT fusion gene. The induction factor is very large (approximately 500–1000 fold) since basal levels of CAT activity produced by pMTVCAT are barely detectible (often zero) in CV-1 cells. As a control experiment, we cotransfected the beta form of the hGR (see Experimental Section I), which was shown to be unable to bind steroids (see Table II-1). FIG. 13 demonstrates that hGR beta is not functional in our expression assay. The activation of transcription by hGR is also restricted to promoters containing a glucocorticoid-responsive element. When pMTVCAT was substituted for pMTIaCAT, a plasmid containing the regulatory region of the human metallothionein Ia gene, which is responsive to heavy metals but not to glucocorticoids, no induction of CAT activity was observed after hormonal treatment of the transfected CV-1 (data not shown). These results demonstrate that in cells the hGR acts as a necessary and sufficient factor that functions as a steroid-dependent transcriptional switch.

Based on this assay, the activation of the receptor by steroids could be examined. As shown in FIG. 14, DEX exhibits an $ED_{50}$ value of 3 nM on hGR-induced CAT activity, which is in agreement with $ED_{50}$ values observed for DEX (5 nM) in a variety of psychological actions. Specificity of hGR action was further tested by treating cotransfected CV-1 cells with 100 nM testosterone, oestradiol, and progesterone. These steroids failed to induce CAT activity with the exception of progesterone, which stimulated hGR function at a value of 1% of the maximal induction produced by DEX (data not shown). These results indicate that transfected CV-1 cells synthesize functional hGR that interacts with pharmacological ligands with the specificity and concentrations of the natural receptor.

Studies on specific interaction between enhancer-containing molecules and cellular components have shown that CV-1 cells contain limiting amounts of cellular factors required for the function of certain viral enhancers (Scholer and Gruss, 1984). In those cells, CAT activity generated by transfected pSV2CAT (Gorman, et al., 1982a) reaches a plateau at 0.3 pmol of plasmid per dish. Similarly, if the hGR interacts with limiting factors, we should be able to saturate the CAT activity induced by transfection of increasing amounts of pRShGR alpha with a constant quantity of pMTVCAT. In this experiment, 2 pmol (5 micrograms) of pMTVCAT DNA was used and increasing amounts of pRShGR alpha DNA were added, together with nonspecific carrier DNA, to yield a total of 30 micrograms per dish. FIG.

15 demonstrates that CAT activity could be detected when as little as 0.03 pmol (100 ng) of pRShGR alpha per dish was transfected and that no plateau in CAT activity was reached. These data suggest that stimulation of transcription of the MTV-CAT fusion gene by hGR is not dependent on transcriptional factors that are limiting in CV-1 cells.

(c) Mapping of Functional Domains in hGR

Understanding the mechanisms by which hGR regulates gene transcription first required the characterization of its functional domains. Based on limited proteolysis studies of the glucocorticoid receptor (Carlsdedt-Duke, 1982; Dellweg, et al., 1982; Wrange, et al., 1984; Reichman, et al., 1984) and on the analysis of the primary structure of the hGR (see Experimental Section I), a model for the structure of the receptor has been proposed (Weinberger, et al., 1985). This model identifies three major domains—an immunological domain spanning from amino acid 145 to 280, a DNA-binding domain extending from amino acids 421 to 481, and a steroid-binding domain located near the carboxyl terminus of the protein. To test this model, we generated 27 site-specific insertional mutations in the glucocorticoid receptor coding sequence via a linker-scanning approach. These genetically engineered mutants were then assayed for their ability to stimulate gene transcription and to bind steroid hormone.

To generate linker-insertion mutants of the hGR, the plasmid pRShGR alpha was first linearized by partial cleavage using a restriction enzyme that cleaves DNA molecules with high frequency. The linear form of the plasmid was isolated and a BamHI linker was added to restore the open reading frame encoding the hGR. The resulting mutants carry three or four additional amino acids, which disrupt the wild-type sequence of the protein. Using this technique, we have generated a random series of hGR mutants (FIG. 16). The ability of these mutants to express full-length hGR was estimated by Western blot analysis. The amounts of hGR produced were shown not to vary by more than 30%, and thus none of the mutants appear to destabilize the expressed protein.

The functional properties of each mutant are compared with that of the wild-type hGR in Table II-1. CAT activity induced by 12 out of 27 hGR mutants was comparable with wild-type level. Analysis of the 15 hGR mutants having a diminished or a complete loss of function, as assayed by induction of CAT activity, shows that they belong to four separate groups. A cluster of these mutants located between amino acids 120 and 215 in the so-called immunogenic domain forms the first group. Although no specific function has been assigned to this region of the receptor molecule, three mutants (I120, I204, and I214) show decreased capacity to induce CAT activity. Those mutants retained their full ability to bind steroids.

Perhaps not surprisingly, the second group of defective mutants is found in the putative DNA-binding domain of the receptor. This domain is cysteine-rich and consists of two repeat units of about 25 amino acids each, which could fold into a loop structure coordinated by a $Zn^{2+}$ ligand (Miller, et al., 1985). In mutant I422, the sequence motif Cys-$X_2$-Cys is changed to Cys-$X_5$-Cys. The presence of the additional amino acids completely abolishes receptor function. Mutant I440 bears a similar insertion of four amino acids between the two other cysteines involved in the formation of the first loop and also fails to induce any detectable level of CAT activity. On the other hand, mutant I428 extends the length of the loop itself, from 13 to 17 amino acids. Although severely diminished, induction of CAT activity by I428 is still measurable. Steroid-binding capacity of all three mutants located in the DNA-binding domain was shown to be in the range of wild-type level. The third region affected by the mutations is located next to the DNA-binding domain. Mutants I488 and I490 show low levels of CAT activity but bind steroid efficiently. The fourth group covers the last 200 amino acids of the receptor protein. Five mutants (I582, I589, I599, I626, and I696) show undetectable levels of CAT activity. This lack of functional activity is correlated with their total incapacity to bind dexamethasone. These results show that the steroid-binding region encompasses a large portion of the protein, all clustered near the C terminus. In contrast to the amino terminus of the molecule, this region is extremely sensitive to changes in the primary structure of the receptor.

TABLE II-I

Functional Properties of hGR Mutants

| hGR | Inserted Amino Acids | CAT Activity (%) | DEX Binding (%) |
|---|---|---|---|
| alpha | — | 100 | 100 |
| I9 | RIR | 117 | NT |
| I37 | RIRA | 95 | NT |
| I102 | GSV | 130 | NT |
| I120 | RGSA | 2 | 76 |
| I204 | RIR | 3 | 125 |
| I214 | RGSA | 2 | 79 |
| I262 | ADPR | 97 | NT |
| I289 | RIR | 125 | NT |
| I305 | ADPR | 86 | NT |
| I346 | ADPR | 19 | 107 |
| I384 | RIR | 101 | NT |
| I403 | ADPR | 114 | NT |
| I408 | ADPR | 55 | NT |
| I422 | GSV | 0 | 105 |
| I428 | RIRA | 2 | 92 |
| I440 | ADPR | 0 | 69 |
| I488 | GSV | 15 | 96 |
| I490 | RIRA | 10 | 115 |
| I515 | RIR | 109 | NT |
| I532 | GSV | 115 | NT |
| I550 | ADPR | 5 | 19 |
| I582 | RIR | 0 | 0 |
| I589 | GSV | 0 | 0 |
| I599 | SDP | 0 | 0 |
| I626 | ADPR | 0 | 0 |
| I684 | RGSA | 79 | 81 |
| I696 | RGSA | 0 | 0 |
| beta | C-terminal deletion | 0 | 0 |

CV-1 or COS cells were transfected with pRShGR alpha, pRShGR beta, or a mutated hGR alpha and assayed for CAT activity and steroid-binding capacity. After transfection, CV-1 cells were cultured for 2 days in the presence of 10 nM DEX before cell lysis and CAT assay; COS cells were maintained in normal media. The two parameters are quantified as percentage (%) of wild-type hGR activity. Amino acids inserted in hGR alpha are given in the one-letter code. NT means not tested. Differences in amino acid composition between hGR alpha and hGR beta are represented in FIG. 16 and in Experimental Section I.

II. D. Discussion

We have shown that hGR produced in CV-1 cells via transfection of an hGR expression vector functions as a necessary and sufficient factor for the transcriptional activation of the MTR-CAT fusion gene. The magnitude of the induction reveals the hGR may act as a transcriptional "switch", which can convert a silent promoter containing a glucocorticoid response element to an activated state. Unlike other transcriptional factors that are constitutively active, stimulation of transcription by hGR is totally dependent upon the presence of glucocorticoid hormones (FIGS. 13 and 14). The production of an excessive quantity of the protein within a cell is not sufficient to induce transcription of a regulated gene. The mechanism by which hGR is activated by the hormone is poorly understood but, in analogy with the cyclic AMP-binding protein, is likely to involve allosteric transitions within the protein (McKay and Steitz, 1981; Gages and Adhya, 1985).

We have observed that activation of transcription by hGR is not restricted by factors present in limiting quantity in CV-1 cells (FIG. 15). These results suggest that the binding of hGR-steroid complex to a glucocorticoid-responsive enhancer is sufficient to increase the activity of general transcriptional factors at nearby promoters. Similar properties for several other transcriptional factors have been reported. For example, Adf1, a transcription factor that activates the proximal promoter of the alcohol dehydrogenase (Adh) gene in *D. melanogaster*, binds the Adh template DNA in the absence of other protein factors and requires only endogenous RNA polymerase Ii and a fraction containing another general transcription factor to activate initiation of Adh RNA synthesis (Heberlein, et al., 1985). In a different type of experiment using the recombinant plasmid pSV2CAT, which contains SV40 enhancer/promoter elements, Scholer and Gruss (1984) have shown a requirement of a cellular molecule(s) for the function of enhancer-containing DNA. Their experiments indicated the presence of a limited amount of cellular factor(s) required for the activation of the CAT gene by the SV40 enhancer element. However, no exhaustion of general transcriptional factors was observed. These data suggest that the mechanism of action of specific positive transcriptional factors is likely to involve alterations in chromatin structure induced by the factor itself that would facilitate the activity of general transcription factors or the polymerase itself (Moreau, et al., 1981; Wasylyk, et al., 1983). It has been previously shown that glucocorticoid treatment causes both reversible and persistent changes in chromatin structure in DNA regions containing a segment of the MTV LTR (Zaret and Yamamoto, 1984). The mechanism by which bound receptors protentiate promoter activity remains to be completely elucidated. However, the availability of a system that overexpresses hGR will facilitate the future studies on the molecular basis of transcription activation by positive transcriptional factors.

The results of the characterization of the 27 insertional mutants supports and extends our previous suggestion that the human glucocorticoid receptor is composed of a series of functional domains. It is noteworthy that all mutants that affect steroid binding are clustered at the carboxyl terminus. In addition to suggesting that this region functions as a discrete domain encoding hormone specificity, the results imply the possibility that the other domains identified within the receptor may serve discrete functions. Accordingly, the ability of the receptor to recognize and to interact with specific DNA sequences appears to reside in the Cys-Lys-Arg-rich region, which is highly conserved with the estrogen receptor and the oncogene product v-erb-A. It seems logical that mutations in these regions would diminish the ability of the receptor molecule to activate transcription since activation depends on both the ability of the ligand to induce an allosteric transformation and the ability of the transformed molecule to recognize and interact with the DNA. Based on the initial model of steroid receptor structure (Weinberger, et al., 1985), these were expected outcomes of a mutagenic characterization. The unexpected outcome, however, is the identification of at least two other regions influencing transcriptional activity. This raises the intriguing possibility that other domains are present in the receptor that are necessary for transcriptional activation but are not specifically involved in either steroid or DNA binding. Mutants I120, I204, and I214 bind steroid with wild-type affinity but have diminished transcriptional activity. These mutants clearly demonstrate that this domain, which we refer to as $tau_1$, is functionally important and required to obtain complete activity of the hGR. Interestingly, nonfunctional truncated mutants (i.e., 40 kd) found in several lines of glucocorticoid-resistant cells are retained in nuclei more efficiently than the wild-type receptor, but fail to activate transcription (Yamamoto, et al., 1976; Andreasen and Gehring, 1981; Westphal, et al., 1984). The receptor fragment missing in these "increased nuclear transfer" ($nt^i$) mutants is evidently the amino terminus of the protein since they retain hormone-binding capacity. We note that $tau_1$, coincides with the major immunogenic domain of the hGR (Weinberger, et al., 1985), indicating that it is probably on the external surface of the molecule. Speculations on how this domain can fulfill its functions include self-interaction leading to receptor dimerization, possible interactions with general transcriptional factors such as RNA polymerase II, and/or modulation of DNA binding by exerting allosteric influence over the remainder of the activated receptor (Dellweg, et al., 1982). $Tau_1$ is englobed by the amino terminus of the receptor, a region which is not held in common with the smaller estrogen receptor. Perhaps the estrogen receptor gains the equivalent function of this domain by interacting with a second protein, or, alternatively, $tau_1$ may interact with other residues within the glucocorticoid receptor itself, as opposed to interacting with other regulatory molecules. The other tau region (which we refer to as $tau_2$) that affects transcriptional activation is a region that is present in the estrogen receptor and the v-erb-A oncogene. Its location also suggests that it may act as a "hinge" region linking the steroid- and DNA-binding domains. Thus, these mutants could block the allosteric transformation necessary for receptor activation.

A third region affected by amino acid insertions is located in the putative DNA-binding domain described by Weinberger, et al. (1985). This domain is composed of two repeated units containing a Cys-Lys-Arg-rich sequence and is the most intensively conserved when compared with the v-erb-A oncogene and the estrogen receptor (Weinberger, et al., 1985; Green, et al., 1986; Greene, et al., 1986). These repeated units were first observed in the factor TF-IIIa (Miller, et al., 1985) and have since been found by sequence homology searches in a number of other nucleic acid-binding proteins (Berg, 1986). Based on experimental and theoretical studies of the actor TFIIIa, Miller and colleagues (1985) proposed a novel mechanism by which proteins bind DNA molecules. In their model, each unit is folded into a "fingered" structure centered on a zinc ion. A finger could bind to a half-turn of DNA. Mutants I422 and I440 carry an amino acid insertion that disrupts the motif Cys-$X_2$-Cys central to the finger model. These mutants are totally inactive with respect to transcriptional activation but retain their ability to bind glucocorticoid hormone. Preliminary experiments revealed that these mutants also fail to translocate to the nucleus after hormone treatment and to bind DNA in vitro (S. Hollenberg, unpublished observations). These mutated receptors demonstrate the functional importance of the finger motifs present in hGR. The third mutant located in this region, I428, has the finger extended by the addition of four amino acids. Transcriptional activity of I428 is greatly impaired (2% of wild-type level), but is still detectable. Thus, the loops are apparently more tolerant of change than the zinc-binding motif. The demonstration that finger-like domains are functionally important in hGR leads us to propose that steroid hormone receptors are metallo-proteins, which may have evolved from a primordial ancestral DNA-binding protein.

Together, these data suggest that the receptor is composed of a melange of regulatory domains, which may have been pirated over evolutionary time to condense into the primordial steroid hormone receptor, which in turn gave rise to the large family of hormone response genes present in the mammalian genome. The transcriptional activity of this molecule demonstrates its potential ability to act as a genetic switch, which is consistent with the role of steroid hormones in activating a variety of developmental lineages and homeostatic functions. The design of the mutations allows for the convenient generation of any desired set of small or large deletional mutants and the ability to switch domains between related molecules to study function. In conjunction with the rapid and quantitative functional assays described in his section, it is now possible to direct specific questions as to the functional nature of the tau, DNA-, and steroid-binding domains.

II. E. Detailed Description of Figures Referred to in Experimental Section II

FIG. 11.

Schematic Representation of the hGR Functional Assay

In this assay, an expression vector containing the hGR alpha cDNA or a mutant derived from it is cotransfected into CV-1 or COS cells with a plasmid carrying the CAT gene under the control of the MTV LTR. The cells are then cultured in the presence or absence of hormone. CV-1 cells were used to monitor induction of CAT activity, and COS cells were used to measure steroid-binding capacity and the expression of hGR protein.

FIG. 12.

Expression of hGR Protein

COS cells were mock-transfected (center lane) or transfected with plasmid pRShGR alpha (right lane) and analyzed 2 days later for the presence of hGR protein. Crude cytoplasmic extracts were resolved by SDS-PAGE and analyzed by Western blot. Cytoplasmic extract from IM9 cells was loaded on the same gel for comparison (left lane).

FIG. 13.

Induction of CAT Activity by hGR

Subconfluent CV-1 cells were cotransfected with either pRSVgal (control), pRShGR alpha, or pRShGR beta and the reporter plasmid pMTVCAT and cultured for 2 days in the presence (+) or absence (−) of 10 nM dexamethasone. CAT assays were performed as indicated in Experimental Procedures (see Section II. F.). C, chloramphenicol; AC, 3-acetylchloramphenicol.

FIGS. 14 and 15.

Dose-Response to DEX and Titration of pRShGR Alpha

FIG. 14 CV-1 cells cotransfected with pRShGR alpha and pMTVCAT (10 micrograms each plasmid) were cultured in the presence of increasing concentrations of dexamethasone. The apparent $ED_{50}$ value for DEX was 3 nM. The levels of CAT activity were plotted as percentages of the maximal response observed in a particular experiment. No CAT activity was detected in the absence of DEX.

FIG. 15 Titration. Increasing amounts of pRShGR alpha were cotransfected into subconfluent CV-1 cells with a constant amount of pMTVCAT (5 micrograms). The plasmid pBR322 was used as carrier DNA to yield a total of 30 micrograms DNA per plate. Cells were cultured for 2 days in the presence of 10 nM DEX and CAT activity was measured and plotted as in FIG. 14.

FIG. 16.

Location of Functional Domains in hGR

The hGR is schematically represented with putative domains involved in transcription activation, $tau_1$, and $tau_2$, indicated by hatched areas. The DNA-binding domain is represented by a stippled box; the steroid-binding domain, by a dotted box. The positions of BamHI linker insertions are indicated by triangles and circles. The numbers refer to the amino acid position (see Experimental Section I) after which the insertion occurs. Open symbols represent mutants capable of inducing hormone-dependent transcriptional activity at wild-type levels, as measured by CAT activity, and closed symbols indicate greatly diminished or abolished function. The bar indicates the location of the divergent amino acids present in hGR beta, which is not functional.

II. F. Experimental Procedures (a) Culture Conditions

CV-1 and COS-1 cells were grown at 37° C. in Dulbecco's modified Eagle's medium supplemented with 5% (v/v) fetal calf serum, 400 microg/ml ampicillin, and 100 microg/ml streptomycin. Cells were passed every 3 days and never allowed to reach confluency in order to obtain good transfection efficiency. All transfected cultures were maintained at 37° C. with 5% $CO_2$.

(b) Recombinant Plasmids

Plasmid pRShGR alpha and pRShGR beta, which direct the synthesis of the two forms of hGR in CV-1 and COS cells, were constructed from three DNA fragments. The first fragment is derived from pRSVCAT (Gorman, et al., 1982b) and contains the RSV LTR, pBR322 sequences, and SV40 polyadenylation site. To obtain this fragment, pRSVCAT was cut with HindIII and the ends repaired by treatment with the Klenow fragment of DNA polymerase I. KpnI linkers were added to these ends by standard procedures (Maniatis, et al., 1982), and the plasmid was subsequently cut with HpaI, which removed the CAT coding sequence. The second fragment contains the coding sequence of either hGR alpha or hGR beta. Plasmids pOB113 and pOB117 (S. M. Hollenberg, unpublished results), which contain the entire coding sequences of the alpha and beta form of hGR, respectively, were cut with BamHI. The ends were repaired with Klenow, and the plasmids were cut with KpnI. Ligation of the first and second fragments created plasmid pRhGR alpha and pRhGR beta. The third fragment to be added consists of a PvuII-HindIII fragment containing the SV40 ORI obtained from the plasmid pSV2CAT (Gorman, et al., 1982a). The ends of this fragment were repaired by treatment with Klenow, and NdeI linkers were added to them. This DNA fragment, containing the SV40 ORI, was then introduced into the single NdeI site present in pRhGR alpha and pRhGR beta. Finally, the single BamHI site present in these plasmids was destroyed and replaced with a XhoI site by insertion of a synthetic adaptor. The resulting plasmids are pRShGR alpha and pRShGR beta. Plasmids pMTVCAT and pMTIa-CAT were gifts from S. Gould.

(c) Insertional Mutagenesis

Insertion of amino acids disrupting the wild-type sequence of hGR alpha was performed by the following method. Full-length linear pRShGR alpha DNA was generated by partial digestion with restriction enzymes AluI, DpnI, and BstNI. In the case of DNA cut by BstNI, the ends were first repaired with Klenow. The DNA molecules were then fractionated by agarose gel electrophoresis, and the linear form of the plasmid was extracted. BamHI linkers of 8- or 12-mer were added to restore the original reading frame of the hGR amino acid sequence. Plasmids carrying a single BamHI linker in the coding region of hGR were sequenced (Maxam and Gilbert, 1980) to confirm the position of the linker and the integrity of the hGR mutants.

(d) Cell Transfection and CAT Assay

The recombinant DNA constructs were introduced into CV-1 cells by calcium phosphate coprecipitation (Wigler, et al., 1979) or into COS cells by DEAE-dextran (Deans, et al., 1984). Each plasmid preparation used for transfection was purified using two consecutive CsCl-EtBr equilibrium gradients. After transfection with the CAT gene constructs, CV-1 cells were prepared for CAT assay as described by Gorman, et al. (1982a). The assays were performed with one third of the total cellular extract and an incubation time of 6 hr.

(e) Western Blot Analysis

Crude extracts from COS cells were prepared by lysis with a buffer containing 10 mM Tris-CHl (pH 7.5), 100 mM NaCl, 1 mM EDTA, 0.5% Triton X-100. Equal amounts of protein (100 micrograms) were resolved by 7.5% polyacrylamide gel electrophoresis, transferred to a nitrocellulose filter, and probed with anti-hGR antibody GR884 (Harmon, et al., 1984), followed by $^{125}$I-labeled *Staphylococcus aureus* protein A. Filters were air dried and exposed to film. The amount of receptor was quantitated by scanning the autoradiographs.

(f) Steroid Binding Assay

COS cells were lysed in hypotonic buffer containing 10 mM Tris-HCl (pH 7.5), 10 mM NaCl, 1 mM EDTA, 5 micrograms/ml antipain, 5 micrograms/ml leupeptin, and 0.5 mM PMSF by Dounce homogenization and centrifuged 10 min. at 15,000×g to yield the cytosolic fraction. Incubations were performed in hypotonic buffer adjusted to 100 mM NaCl and contained 100 micrograms of protein from the cytosolic fraction and $2\times10^{-8}$ [$^3$H] DEX (Amersham, 95 Ci/mmol) in total volume of 200 microliters. Nonspecific binding was measured by the addition of $2\times10^{-6}$ unlabeled DEX. Reactions were carried out at 0° C. for 2 hr., followed by a 5 min. incubation with 20 microliters of 50% dextran-coated charcoal (10:1 activated charcoal:dextran) and centrifugation at 15,000×g for 2 min. at 4° C. Supernatants were counted by liquid scintillation methods in a Beckman LS-7800 liquid scintillation spectrophotometer. Each assay usually gave 2500–3000 cpm [$^3$H] labeled steroid; unlabeled DEX competed for 70% of this binding.

EXPERIMENTAL SECTION III

Cloning of Human Mineralocorticoid Receptor Complementary DNA: Structural and Functional Kinship with the Glucocorticoid Receptor

III. A. Summary

Low-stringency hybridization with human glucocorticoid receptor (hGR) complementary DNA was used to isolate a new gene encoding a predicted 107-kilodalton polypeptide. Expression studies demonstrate its ability to bind aldosterone with high affinity and to activate gene transcription in response to aldosterone, thus establishing its identity as human mineralocorticoid receptor (hMR). This molecule also shows high affinity for glucocorticoids and stimulates a glucocorticoid-responsive promoter. Together the hMR and hGR provide unexpected functional diversity in which hormone-binding properties, target gene interactions, and patterns of tissue-specific expression may be used in a combinatorial fashion to achieve complex physiologic control.

III. B. Introduction

The hypothalamic-pituitary-adrenal axis integrates a variety of neuroendocrine inputs to regulate the synthesis and secretion of the adrenal corticosteroids. These steroid hormones exert effects on growth, development, and homeostasis by their interaction with intracellular receptor proteins that directly regulate the transcription of sets of target genes (1,2). Two receptor systems have been defined for the corticosteroids; these are termed the glucocorticoid receptor (GR) and the mineralocorticoid receptor (MR). Early functional assays classified the corticosteroids as either glucocorticoid, by their effect in promoting glycogen deposition in the liver, or mineralocorticoid, by their effect in promoting sodium retention by the kidney. However, each steroid class is not restricted to interacting with only its cognate receptor, and glucocorticoids, in particular, can have substantial mineralocorticoid activity (1–3).

It is now evident that the MR has significant in vitro affinity for both glucocorticoids and mineralocorticoids (3,4). Since the circulating levels of glucocorticoids are several orders of magnitude higher than those of aldosterone, the primary mineralocorticoid, glucocorticoid activation of the MR may be functionally significant. Whereas the secretory epithelia of tissues such as kidney and intestine regulate electrolyte and water balance in response to aldosterone, it is possible that additional mechanisms confer these tissues with sensitivity to mineralocorticoids (5). No clear functional role has emerged for the MR expressed in other tissues, but physiological responses in brain may result from glucocorticoid interactions with the MR (5–7).

Despite the availability of high-affinity radioactively labeled ligands, the MR has been refractory to purification, and its biochemical properties, in comparison to GR, remain poorly understood. Application of the techniques of molecular biology to the study of the MR would facilitate its biochemical characterization and, eventually, an understanding of the genes under its transcriptional control and the roles their products play in homeostasis.

Molecular cloning of the glucocorticoid. (see Experimental Section I and refs. 8,9), estrogen (10), and progesterone (11) receptors has permitted the determination of their primary amino acid structures and prediction of functional domains common to this family of regulatory proteins. Experimental dissection of glucocorticoid (see Experimental Section II and ref. 12) and estrogen (13) receptors has revealed a centrally located DNA-binding domain rich in cysteine, lysine, and arginine, and a carboxyl-terminal region where steroid hormones interact. Functional studies of GR suggest that hormone binding to the carboxyl terminus unmasks the DNA binding region to permit interactions of receptor with DNA and activation of transcription (14, 15). Comparison of the cysteine-rich DNA-binding regions of steroid and thyroid hormone receptors shows a high degree of relatedness between these molecules (16). The invariant cysteine residues have led to the hypothesis that coordination of $Zn^{2+}$ metal atoms maintains a structural configuration for DNA binding analogous to that proposed for *Xenopus* 5S gene transcription factor IIIA (17). The steroid-binding regions of the steroid receptor family also show substantial conservation consistent with evolution of various receptor classes from a common ancestral precursor (11, 16).

We have used the structural similarity between steroid hormone receptors to isolate a gene product closely related to the human glucocorticoid receptor (hGR). Nonstringent hybridization with an hGR probe was used to isolate a human genomic DNA fragment highly related to the hGR cysteine-rich sequence. Using this DNA as a probe, we obtained complementary DNA's (cDNA's) that code for a molecule having a strong homology with the hGR from the cysteine-rich region to the carboxyl terminus. When expressed in cells, this molecule binds aldosterone with high affinity and activates aldosterone-response transcription of the long terminal repeat (LTR) of the mouse mammary tumor virus (MMTV). The overlap of the ligand and DNA sequence specificities of this human mineralocorticoid receptor with those of hGR suggest that the distinct roles traditionally assigned to these regulatory molecules should be reconsidered.

III. C. Isolation of hMR cDNA

For the identification of glucocorticoid receptor-related genes, human placenta DNA was digested with restriction endonucleases, fractionated by agarose gel electrophoresis, and the fractions were hybridized with hGR 1.2, an 1100-bp fragment of hGR cDNA containing sequences encoding the DNA-binding domain (see Experimental Section I; also ref. 15). Southern blot analysis revealed several distinct bands specific to low-stringency hybridization conditions (compare FIGS. 21 and 22). The 2.5-kilobase pair (kbp) HindIII fragment (bracketed by asterisks in FIG. 18) was well resolved from other hybridizing bands and was judged suitable for direct genomic cloning. HindIII-digested DNA from human placenta was preparatively size-fractionated on an agarose gel, and the 2.5-kbp region was isolated for the construction of a genomic library. This lambda gt10 library was then screened under conditions of low-stringency hybridization with hGR 1.2 as the probe. The insert from one positive genomic clone, lambda HGH, was nick-translated and used as a probe on a Southern blot under high-stringency hybridization conditions (FIG. 19). The 2.5-kbp HindIII signal corresponded to that seen under nonstringent conditions, indicating that a portion of the desired genomic fragment had been isolated. Sequence analysis of the insert from lambda hGH revealed an exon of 140 base pair (bp) flanked by intron sequences (FIG. 20). Overall this exon has 68 percent nucleotide identity with the homologous hGR cDNA sequence, but a region conserving 85 nucleotides out of 104 probably confers its cross-hybridization properties. This highly conserved region corresponds to a portion of the hGR DNA-binding domain (15). The lambda HGH exon codes for 46 amino acids beginning with 16 nonconverted residues and followed by the first of the highly conserved cysteine residues characteristic of steroid hormone receptors (8–11). Of the next 30 residues, 28 are identical to hGR. These analyses demonstrated the isolation of a genomic fragment containing a sequence related to, but clearly distinct from, that found in the hGR cDNA sequence (see Experimental Section I).

The insert from lambda HGH was used as a probe to screen cDNA libraries for clones corresponding to this hGR-related gene. Mineralocorticoid receptor was considered a candidate to be encoded by such a gene. Since kidney is known to be a mineralocorticoid-responsive tissue, several human kidney cDNA libraries were screened. Eleven positive clones were isolated from these lambda gt10 libraries at a frequency of three to four per $10^6$ recombinant phage. Two overlapping clones, lambda hk2 and lambda hk10, were subjected to nucleotide sequence analysis and together found to span 5823 nucleotides (FIGS. 21 and 22A–E). The exon-intron boundaries of lambda HGH were verified by sequencing these cDNA clones. The lambda hk10, encompassing nucleotides 1 to 3750, contains a large open reading frame predicting the entire primary amino acid sequence. The DNA insert from lambda hk2 extends from nucleotides 802 to 5823, but contains an internal 351-bp deletion from 2235 to 2586. Three additional clones were examined and determined to have the same structure as lambda hk10 in the deleted region. It is likely that the deletion in lambda hk2 represents either a cloning artifact or a rare messenger RNA (mRNA) splicing error (18). The sequence of the reported 3'-untranslated region downstream of nucleotide 3750 is derived from lambda hk2. The composite sequence of these two cDNA's is termed hMR (FIG. 21). With the first in-frame ATG (position 223) downstream of an in-frame termination codon (position 136), hMR has a 5'-untranslated region of at least 216 nucleotides. The sequence surrounding this first ATG agrees with the consensus described by Kozak (19). This predicted initiator methionine codon begins an open reading frame encoding 984 amino acids. Following a termination codon (position 3175) is a 2.6-kb 3'-untranslated region with a typical polyadenylation signal (AATAAA) found 17 nucleotides upstream of a 70-nucleotide poly(A) (polyadenylated) tract. Long 3'-untranslated regions are a characteristic feature of steroid hormone receptor mRNA's (see Experimental Section I; also refs. 9–11).

III. D. The DNA- and Hormone-Binding Regions

The protein encoded by hMR cDNA has the structural properties of a steroid hormone receptor closely related to hGR. Comparison of the predicted amino acid sequence of hMR with that of hGR demonstrated high degrees of homology with both the hGR DNA binding and steroid binding domains. The hMR gene encodes a protein of 984 amino acids with a predicted molecular size of 107 kD, significantly larger than the 777 residues of hGR. This size discrepancy is primarily due to the large amino terminus, which bears no homology to hGR. Considerable heterogeneity of size and sequence for this region exists between the receptors for glucocorticoid, estrogen, and progesterone (see Experimental Section I; also refs. 9–11). Amino acid homology begins in the centrally located DNA region with 94 percent amino acid identity in 68 residues (FIGS. 23A and B). Separating the DNA-binding domain and the carboxyl-terminal steroid-binding domain is a region with relatively low sequence conservation found between other steroid hormone receptors. It has been speculated that the region may serve as a molecular hinge between the two domains (see Experimental Section II and ref. 13). Comparison with hGR shows this region of hMR to contain an additional 24 amino acids including a sequence of 4 glutamines followed by 8 prolines encoded by repetitive nucleotide elements. The significance of this unusual sequence in terms of origin and function is unclear, but structure-breaking prolines are consistent with a hinge region. A comparison of the carboxyl-terminal 250 amino acids of hMR with hGR shows 57 percent amino acid identity as well as a number of conservative amino acid substitutions. Some of these substitutions may preserve hydrophobic regions necessary for steroid hormone interaction.

III. E. Expression and Hormone Binding

We have used transfection of the monkey kidney cell line CV1 and its derivative (that is, SV40 T antigen-transformed) cell line COS-1 (referred to as COS) to study glucocorticoid receptor function. (See Experimental Section II.) High levels of polypeptide expression from transfected hMR were essential to facilitate steroid-binding experiments in transfected cells. Since plasmids containing the SV40 origin of replication can replicate to high copy numbers in COS cells, an expression vector for hMR coding sequences similar to pRShGR alpha, used previously in hGR studies, was constructed. The plasmid, pRShMR, contains the hMR coding sequence, under the control of the promoter from Rous sarcoma virus, and the SV40 origin of replication (FIG. 24).

Ligand specificity of the hMR protein was determined by preparing cytosol extracts from COS cells transfected with pRShMR. Two days after transfection, cells were harvested, and hormone binding was measured by a dextran-treated charcoal assay. Mock-transfected control extracts had no specific binding activity for [$^3$H] aldosterone, whereas extracts from pRShMR-transfected cells found significant amounts of [$^3$H] aldosterone with high affinity. A dissociation constant ($K_D$) of 1.3 nM for the binding of [$^3$H] aldosterone was determined by a Scatchard analysis (FIG. 25). This value is in good agreement with those reported for aldosterone binding to mineralocorticoid receptor (2, 20). Competition experiments were then performed to examine the ability of different unlabeled steroids to compete with 5 nM [$^3$H] aldosterone for binding when present at 1-, 10-, or 100-fold molar excess (FIGS. 26 and 27). This provided a measure of the relative affinity of each of these steroids for hMR. The results of these experiments show that aldosterone, corticosterone, deoxycorticosterone, hydrocortisone (cortisol) all have very similar affinities for hMR. Dexamethasone, progesterone, and spironolactone demonstrated weaker binding affinity while estradiol competed very poorly for binding to hMR. Overall, this hierarchy of affinities indicated that hMR encoded the human mineralocorticoid receptor (2, 20).

III. F. Transcriptional Activation

Steroid hormone action is characterized by hormone-dependent modulation of target gene transcription. The assay for transcriptional regulation by transfected hGR in CVI cells (see Experimental Section II) was adapted to hMR (FIGS. 28 and 30). The expression plasmid used for steroid-binding assays, pRShMR, was cotransfected with a reporter plasmid called GMCAT, which contains the MMTV LTR linked to the bacterial gene for chloramphenicol acetyltransferase (CAT). Thus CAT activity provides an enzymatic assay for the transcriptional activity of the MMTV promoter. The MMTV promoter contains several glucocorticoid response elements (GRE's), enhancer-like DNA sequences that confer glucocorticoid responsiveness via interaction with the GR (21). It was possible that hMR, because of the near identity of its DNA-binding domain to that of hGR, might also recognize the MMTV LTR. When CV1 cells were cotransfected with pRShMR and GMCAT, we observed full CAT activity. This activity was independent of added aldosterone suggesting that, in contrast to transfected hGR, sufficient hormone was present in serum (fetal calf serum, 5 percent) to fully activate hMR (FIG. 29). In the presence of charcoal-treated serum (22) CAT activity became responsive to the addition of exogenous aldosterone (FIG. 30), indicating that hMR cDNA encodes a functional steroid hormone receptor. While the hMR was also activated by the glucocorticoid agonist dexamethasone, the hGR did not respond to even supraphysiological concentrations (10 nM) of aldosterone.

III. G. Tissue-Specific Expression

We examined the expression of MR mRNA homologous to hMR cDNA in rat tissues by Northern blot hybridization (23). Classical mineralocorticoid target tissues such as kidney (24) and gut (25), as well as tissues such as brain, pituitary, and heart, contained mRNA homologous to hMR (FIG. 31). Aldosterone-sensitive cells in kidney are primarily restricted to the distal and cortical collecting tubules (2), and therefore a modest level of expression in this tissue was not unexpected. High levels of MR (type I corticosteroid-binding sites) have been reported in rat brain, particularly in the hippocampal formation (4, 6). In comparing dissected hippocampal RNA with RNA prepared from total brain, we found a striking enrichment of message in the hippocampus. While aldosterone binding has been reported for pituitary (26), cultured aortic cells (27), and spleen (28), no such activity has been reported in muscle. Liver expresses GR, but has no detectable high-affinity aldosterone-binding activity (29), and as would be expected no hybridization to liver RNA was observed. Reprobing of the same Northern blot with an analogous portion of hGR cDNA demonstrated hybridization to mRNA species of different sizes, and indicated that the MR and GR do show differential patterns of tissue-specific expression.

III. H. Chromosome Mapping

To determine the chromosomal location of the mineralocorticoid receptor gene, we tested hMR against a panel of rodent-human somatic cell hybrids retaining different combinations of human chromosomes (30). The DNA fragments specific for the mineralocorticoid receptor gene segregated concordantly with human chromosome 4 in 15 hybrid cell lines. Discordant segregation was observed for all other human chromosomes, including chromosome 5, site of the glucocorticoid receptor gene (see Experimental Section I and ref. 31). To confirm the assignment to chromosome 4, we tested a restricted set of microcell hybrids, each of which carry one to three human chromosomes (32), for the hMR gene by Southern analysis (FIG. 32). Six EcoRI fragments detected by the coding portion of lambda hk2 co-segregate with chromosome 4 in this hybrid panel. In particular, the hMR gene is present in HDM-1132B, a cell line that carries chromosome 4 as its only human chromosome.

III. I. Implications for Adrenal Corticosteroid Physiology

Human mineralocorticoid receptor cDNA encodes a polypeptide that is highly homologous to the human glucocorticoid receptor. In the DNA-binding domain, hMR maintains approximately 94 percent amino acid identity to hGR while the steroid-binding domain localized in the carboxyl terminus has 57 percent identity. The recently reported sequence. (11) of the rabbit progesterone receptor (rPR) also has a high degree of relatedness to hMR. Comparison of the amino acid identity in hGR and rPR structural domains with that of hMR (FIG. 33) demonstrates the remarkable similarity of these functionally distinct regulatory proteins. The homology of hMR with rPR is almost identical to the hGR-hMR comparison, with 90 percent of the amino acids shared in the DNA-binding domain and 56 percent in the steroid-binding region. In contrast, a comparison of the same regions of hMR with human estrogen receptor (10) indicates 56 percent identity in the DNA binding domain and 21 percent sequence identity in the steroid-binding carboxyl terminus. The degree of structural homology shared by hMR, hGR, and rPR, and the structural relatedness of their ligands, suggests that they may comprise a subfamily of steroid hormone receptors.

Expression of the hMR polypeptide in COS cells by transient transfection permitted the evaluation of its steroid-binding potential. The results of these analyses indicated that hMR cDNA encodes a human mineralocorticoid receptor. Scatchard analysis demonstrated that extracts from cells transfected with pRShMR bound [$^3$H] aldosterone with a $K_D$ of 1.3 nM, while reported $K_D$ values for aldosterone binding to MR range from 0.5 to 3 nM (2). This is the single most important criterion in defining this gene product as the human mineralocorticoid receptor. Steroid-binding competition studies have further supported this identification of hMR. The mineralocorticoid deoxycorticosterone and the glucocorticoids corticosterone and cortisol compete as effectively as aldosterone itself, whereas the synthetic glucocorticoid dexamethasone and progesterone have lower affinities for the hMR.

The extensive amino acid sequence identity in the presumptive steroid-binding domains of hMR, hGR, and rPR is compatible with the similar ligand-binding properties of these receptors. The mineralocorticoid, glucocorticoid, and progesterone receptors exhibit a limited ability to discriminate between the similar 21-carbon atom structures of the mineralocorticoids, glucocorticoids, and progestins. This lack of specificity is particularly relevant to the MR and GR. For example, the MR binds glucocorticoids with an affinity equal to that for aldosterone. Indeed, it may be that only in tissues such as kidney, where additional mechanisms confer selective response to aldosterone, does the MR function as a classical mineralocorticoid receptor (3, 5). The MR also binds progesterone with a high affinity, but one lower than its affinity for corticosteroids. There is some indication that progesterone may act as a partial agonist or antagonist of mineralocorticoid action (33), and it is not clear whether glucocorticoids act as full agonists in binding to the mineralocorticoid receptor. Similarly, the GR binds glucocorticoids with a $K_D$ between 20 to 40 nM and it binds aldosterone with a $K_D$ between 25 to 65 nM (2). Therefore, the important distinction between the hormone-binding properties of MR and GR may not be one of ligand specificity, but rather of a high-affinity versus a lower affinity receptor for the corticosteroids.

The function of the hMR in vivo is complicated by the serum cortisol-binding protein, transcortin. This protein sequesters cortisol and, because of its differential distribution, transcortin could influence local glucocorticoid concentration. High levels of transcortin in kidney would reduce available cortisol from plasma to favor aldosterone sensitivity, whereas low levels of transcortin in the brain would suggest that, in the central nervous system, glucocorticoids may be the predominant hMR ligand. Thus, the preferred physiologic ligand for hMR apparently varies depending on the site of receptor expression (3). This model and others (5) have been proposed to explain the responsiveness of some tissues to aldosterone despite much higher levels of competing glucocorticoids.

The degree of homology between hMR and hGR in the DNA-binding domain (only four amino acid residues differ in this conserved 68-residue region) suggests that these receptors may recognize similar regulatory elements. The activation of the MMTV LTR by the transfected hMR in response to both aldosterone and dexamethasone supports this conclusion, although the progesterone receptor has also been demonstrated to regulate this promoter (21). Furthermore, differences between hMR and hGR in the DNA-binding domain, or in other regions such as the highly divergent amino termini of these molecules, may influence target gene specificity in ways not revealed in this assay. However, we have utilized transcriptional regulation of the MMTV LTR by hMR and hGR to examine their activation by mineralocorticoids and glucocorticoids. While the hMR response was approximately equivalent with either 10 nM aldosterone or dexamethasone, hGR was activated by dexamethasone but was insensitive to aldosterone in this assay. Transcriptional activation by hMR in response to exogenous cortisol was also observed. These data indicate that in transfected cells both mineralocorticoids and glucocorticoids can activate hMR-mediated gene transcription. On the basis of this functional property, we conclude that the hMR is highly responsive to adrenal corticosteroids and therefore may function as a glucocorticoid receptor.

In addition to elucidating the pharmacologic and physiologic function of the mineralocorticoid receptor in coordinating response to corticosteroids, the isolation of hMR cDNA will facilitate investigation of the role of hMR in a number of disease states, among them hypertension and pseudohypoaldosteronism (PHA). An association of mineralocorticoids with hypertension has been recognized for several decades, and it may be that hMR-mediated sodium retention and increased blood volume are, in part, responsible for some forms of hypertension (34). PHA is an autosomal recessive disorder characterized by lack of responsiveness to normal or elevated aldosterone levels. Recent work has demonstrated diminished or complete loss of high-affinity aldosterone-binding sites in patients with this disease (35) which is likely to result from a mineralocorticoid receptor genetic defect. The chromosomal mapping of the hMR gene suggests the PHA locus should reside on chromosome 4.

Cloning and expression of functional hMR has provided unexpected insight and should stimulate new interest into the mechanisms underlying physiologic complexity, and allow the development and testing of new models for the coordinate regulation of gene networks.

III. J. Detailed Description of Figures Referred to in Experimental Section III

FIGS. 17–20.

Isolation of a genomic sequence related to the hGR gene. FIG. 17 High-stringency Southern analysis of human placenta DNA digested with the indicated restriction endonucleases. hGR cDNA (hGR1.2) was used as a probe. Sizes of lambda DNA fragment markers (in kilobase pairs) prepared by HindIII digestion are indicated next to the autoradiogram. FIG. 18 Low-stringency Southern analysis. The 2.5-kbp band bracketed by asterisks in the HindIII lane was the sequence targeted for direct genomic cloning. FIG. 19 Isolation of this genomic sequence in a clone designated lambda HGH is demonstrated by its use as a probe on a similar Southern blot. The lambda HGH genomic fragment contains the hybridizing internal EcoRI fragment isolated from this cloning. FIG. 20 The intron-exon structure of the lambda HGH genomic fragment and its homology with hGR. The hGR-related exon found within lambda HGH is boxed in black with its predicated amino acid sequence. Conserved cysteine residues are indicated with white dots. Portions of intron sequence with consensus splice donor and acceptor sites underlined are shown flanking the exon. Nucleotide homology with the hGR is shown underneath. Nucleotide numbers for hGR are from FIGS. 3A–H, discussed in Experimental Section I; also see Hollenberg, et al. (1985) (ref. 8) for publication of the study used herein as Experimental Section I. For Southern analysis, we digested DNA from human term placenta with restriction endonucleases, and products were separated on a 0.8 percent agarose gel. The DNA's were transferred to nitrocellulose paper and hybridized under either stringent or nonstringent conditions. Stringent hybridization was performed with 50 percent formamide, 5×SSPE (NaCl, $NaH_2PO_4$, EDTA, pH 7.4), 1× Denhardt's, 0.1 percent SDS, salmon sperm DNA at 100 microgram/ml, and probe ($10^6$ cpm/ml) at 42° C. For nonstringent hybridization, 35 percent rather than 50 percent formamide was used. Washing conditions consisted of 0.1× SSC (standard saline citrate) with 0.1 percent SDS at 60° C. for stringent analyses and 2×SSC with 0.1 percent SDS at 55° C. for nonstringent filters. Washing conditions with the 338-bp inset from lambda HGH as probe were modified to 2×SSC with 0.1 percent SDS at 68° C. For isolation of lambda HGH, human placenta DNA (300 microgram) was digested with HindIII and size-fractionated on a 1 percent low-melting agarose gel (Seaplaque, FMC). The gel was sliced in 0.5-cm strips, and the DNA was purified by phenol extraction and ethanol precipitation. DNA (2 microgram) from the fraction corresponding in size to the band bracketed by asterisks in FIG. 32 was repaired with Klenow DNA polymerase for EcoRI linker addition. After digestion with EcoRI and removal of excess linkers on a Sepharose 4B column, this DNA was ligated to EcoRI-digested lambda gt10 DNA and packaged in vitro (lambda arms and extracts from Vector Cloning Systems, San Diego, Calif.). About $4\times10^5$ independent recombinants were screened under conditions identical to those used for the nonstringent Southern analysis to obtain lambda hGH.

FIGS. 21 and 22A–E.

Nucleotide sequence and primary amino acid structure of human mineralocorticoid receptor. FIG. 21 Composite structure of hMR aligned with a line diagram of some restriction endonuclease cleavage sites (EcoRI sites shown at nucleotides I and 5823 and derived from linkers). The composite was assembled from two overlapping lambda gt10 clones, lambda hk10 and lambda hk2. Parentheses in the line diagram of lambda hk2 indicate a 351-bp deletion. The hatched box indicates predicted coding sequence with initiator and termination codons indicated. FIGS. 22A–E Complete nucleotide sequence of hMR and its predicted primary amino acid sequence. Underlined are a 5' in-frame termination codon upstream of the predicted initiator methionine and four potential polyadenylation sites (AATAAA). Human kidney lambda gt10 libraries (18) were screened with the insert from lambda HGH under the same conditions described for Southern analysis under high-stringency conditions with this probe. Overlapping deletions of each cDNA were obtained (36) by the Cyclone rapid deletion subcloning method (International Biotechnologies). Deletion clones were sequenced by the dideoxy procedure (37), and any gaps or ambiguities were resolved by the chemical cleavage method (38). DNA sequences were compiled and analyzed by the programs of Devereux, et al. (39) and Staden (40).

FIGS. 22A and B.

Amino acid homology of mineralocorticoid receptor with glucocorticoid receptor. The primary amino acid sequence of hMR has been aligned with that of hGR for maximum homology by introducing gaps as indicated by dots. Numbers were taken from FIGS. 21 and 22A–E for hMR and from FIGS. 3A–H for hGR. No significant homology was found upstream of the region shown. Vertical lines indicate identical amino acid residues. Arrows show putative boundaries of the DNA-binding (DNA) and steroid-binding (Steroid) domains. The amino-terminal border of the DNA-binding domain was arbitrarily defined by the first conserved cysteine residue while the carboxyl-terminal limit was chosen on the basis of mutagenesis studies which indicated sequences necessary for DNA-binding and transcriptional activation (15). Several conserved basic residues that follow the DNA binding domain may also be important for these functions. The limits of the steroid-binding domain, while defined by the region of amino acid homology, are also consistent with mutational analysis. Single letter abbreviations for the amino acid residues are: A, Ala; C, Cys; D, Asp; E, Glu; F, Phe, G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

FIGS. 24–27.

Steroid-binding properties of expressed hMR. FIG. 24 Structure of pRShMR, the hMR expression plasmid (41). FIG. 25 Scatchard analysis of tritiated aldosteone binding in extracts prepared from pRShMR-transfected COS cells. Each point was assayed in triplicate with 100 micrograms of extract protein in a 200-microliter incubation at 0° C. for 2.5 hours. The nonspecific binding determined with a 500-fold excess of unlabeled aldosterone was approximately 20 percent of total counts. No specific binding was seen in mock-transfected cells. FIGS. 26 and 27 Competition of unlabeled steroids for binding with 5 nM [$^3$H] aldosterone in transfected COS cell extracts. The results of two independent trials representative of these competition experiments are shown. Cold competitor was present in 1-, 10-, or 100-fold molar excess. The value for 100 percent binding was determined by subtracting the number of counts per minute bound in the presence of 1000-fold excess of unlabeled aldosterone from the counts bound in the absence of competitor. Abbreviations: Aldo, aldosterone, Doc, deoxycorticosterone; Dex, desamethasone; Spiro, sprionolactone; E21, 17 beta-estradiol; CS, corticosterone; HC, hydrocortisone; and Prog, progesterone. Subconfluent COS cells were transfected by the DEAE-dextran method (42) with 10 micrograms of pRShMR per dish. Cells were maintained for 2 days in DMEM (Dulbecco's modification of Eagle's minimum essential medium) with 5 percent charcoal-treated fetal calf serum, then harvested [in 40 mM tris-HCl (pH 7.8), 10 mM NaCl, 1 mM EDTA, 10 mM $Na_2MoO_4$, 5 mM dithiothreitol, antipain (5 microgram/ml), leupeptin (5 microgram/ml), and 500 microM phenylmethylsulfonyl fluoride. After centrifugation at 15,000×g for 10 minutes, extracts were adjusted to 100 mM NaCl and 5 percent glycerol before binding. Labeling reactions with [$^3$H] aldosterone (specific activity 78 Ci/mmol, Amersham) were incubated for 2.5 hours at 0° C. in a total volume of 200 microliters, and then for 10 minutes with 20 microliters of 50 percent dextran-coated charcoal (10:1 activated charcoal:dextran). After centrifugation at 15,000×g for 2 minutes at 4° C., tritium in supernatant was quantified by liquid scintillation spectrophotometry.

FIGS. 28–30.

Transcriptional activation of MMTV LTR by hMR and hGR expression plasmids in transfected CVI cells. FIG. 28 Structure of GMCAT. This plasmid was cotransfected with the steroid receptors as a reporter gene for hormone-dependent transcriptional activation (see Experimental Section II). FIG. 29 Differential CAT enzyme activity found after hMr or hGR transfection with normal serum. Transfected cells were maintained in DMEM with 5 percent fetal calf serum. Serum was treated with charcoal to eliminate free steroids in subsequent experiments so that the effects of exogenous steroids could be determined. FIG. 30 Differential induction of CAT activity by aldosterone or dexamethasone in cells transfected with hMR or hGR. CVI cells were cotransfected with 10 micrograms of either pRSVgal (control), pRShMR, or pRShGR alpha and 10 micrograms of the reporter GMCAT and cultured in the absence (–) or presence of 10 nM aldosterone (A) or 10 nM dexamethasone (D) AC, 3-acetylchloramphenicol; C, chloramphenicol. Two days after transfection by calcium phosphate coprecipitation (43), extracts were prepared for CAT assay (44). The assays were incubated for 6 hours with 50 micrograms of protein extract.

FIG. 31.

Northern analysis of mineralocorticoid receptor mRNA's in rat tissues. The 1270-bp EcoRI fragment (1770 to 3040) from lambda hk10 was used as a probe for the expression of homologous mRNA's in rat. Ten micrograms of poly(A)$^+$ mRNA were used in all lanes. Migration of ribosomal RNA's (28S and 18S) are indicated for size markers. After hybridization under stringent conditions, the filter was washed twice for 30 minutes each time in 2×SSC with 0.1 percent SDS at 68° C.

FIG. 33.

Chromosomal localization of hMR gene by Southern analysis of microcell hybrids. The construction and characterization of these hybrids has been previously described (32). The human chromosome content of each is as follows: HDm-4A (chromosome 20), HDm-5 (chromosome 14 and an unspecified E group chromosome), HDm-9 (chromosomes 20, 14, and 21), HDm-15 (chromosomes 21, 11, and 4), HDm-20 (chromosomes 7 and 14), and HDm-1132B (chromosome 4 only). Human (HeLa) and mouse (3T#) control DNA samples are also shown. Genomic DNA from microcell lines (10 micrograms) was digested with EcoRI and subjected to electrophoresis through a 1.0 percent agarose gel, transferred to a nylon membrane (Nytran, Schleicher & Schuell), and hybridized with a hMR cDNA probe under high-stringency conditions (FIG. 30–33). Radioactive probe was synthesized by the Klenow fragment of *Escherichia coli* DNA polymerase from two randomly primed (45) hMR cDNA templates (the 1000- and 800-bp EcoRI fragments of lambda hk2). The sizes of HindIII-digested lambda DNA fragments are indicated next to the autoradiogram.

FIG. 33.

Schematic amino acid comparisons of the hGR, hMR, and rPR structures. Primary amino acid sequences have been aligned schematically with the percentage amino acid identity indicated for each region of homology in the intervals between dotted lines. The amino acid position of each domain boundary is shown for each receptor. N and C represent the amino and carboxyl termini, respectively. Cys corresponds to the cysteine-rich region encoding the putative DNA-binding domain while Steroid (cortisol, aldosterone, or progesterone) designates the steroid-binding domain. The immunogenic region (IMM) of the hGR is also indicated. Amino acid residue numbers are taken from (see Experimental Section I) for hGR, Loosfelt, et al. (11) for rPR, and from our data for hMR.

SPECIFICATION SUMMARY

From the foregoing description, one of ordinary skill in the art can understand that the present invention provides substantially pure DNA's comprised of sequences which encode proteins having the hormone-binding and/or transcription-activating characteristics of a glucocorticoid receptor, a mineralocorticoid receptor, or a thyroid hormone receptor. The invention also provides various plasmids containing receptor sequences which exemplify the DNA's of the invention. Exemplary plasmids of the invention have been deposited with the American Type culture Collection for patent purposes.

The invention is also comprised of receptor proteins, including modified functional forms thereof, expressed from the DNA's (or mRNA's) of the invention.

In addition to novel receptor DNA, RNA and protein compositions, the present invention involves a bioassay for determining the functionality of a receptor protein. It also involves two new methods for producing desired proteins in genetically engineered cells. The first is a method for inducing transcription of a gene whose transcription is activated by hormones with complexed the receptors. The second is a method for engineering a cell and then increasing and controlling production of a protein encoded by a gene whose transcription is activated by hormones complexed with receptor proteins.

The DNA's of the invention can be used to make the hormone receptor proteins, and functional modified forms thereof, in quantities that were not previously possible. With the quantities of receptor available as a result of the present invention, detailed structural analyses of the proteins can now be made by using X-ray diffraction methods to analyze receptor crystals. In addition, adequate supplies of the receptor proteins mean that they can now be used to screen compounds for receptor-agonists or receptor-antagonist activity. Availability of the receptor proteins also means that they can be used in diagnostic assays.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An expression system for production of functional recombinant glucocorticoid receptor protein(s), wherein said system comprises host cells containing exogenous DNA encoding said glucocorticoid receptor protein(s), wherein the DNA is operably linked to control sequences compatible with said host cells, and wherein said glucocorticoid receptor is a member of the steroid/thyroid hormone receptor superfamily and comprises a DNA binding domain and a ligand binding domain.

2. An expression system according to claim 1 wherein the host cells are mammalian.

3. An expression system according to claim 2 wherein the host cells are CV-1 cells.

4. A method to produce glucocorticoid receptor protein(s), said method comprising culturing the cells of the expression system of claim 1 and recovering the functional glucocorticoid receptor protein(s) produced thereby.

5. A method according to claim 4 wherein the functional glucocorticoid receptor protein is recovered by disrupting the cells, removing cell debris, and recovering clarified lysate.

6. Recombinant DNA capable of hybridizing with DNA encoding glucocorticoid receptor having the amino acid sequence shown in FIGS. 3(A) and 3(B), or DNA complementary thereto, under nonstringent hybridization conditions comprising hybridization in 35% formamide, 5×SSPE, 1% Denhardt's reagent, 0.1% sodium dodecyl sulfate, 100 μg/mL salmon sperm DNA, at 42° C.; and washing with 2×SSC, 0.1% sodium dodecyl sulfate, at 55° C.

7. DNA according to claim 6 capable of hybridizing with DNA encoding glucocorticoid receptor having the amino acid sequence shown in FIGS. 3(A) and 3(B), or DNA complementary thereto, under stringent hybridization conditions comprising hybridization in 50% formamide, 5×SSPE, 1% Denhardt's reagent, 0.1% sodium dodecyl sulfate, 100 μg/mL salmon sperm DNA, at 42° C.; and washing with 0.1×SSC, 0.1% sodium dodecyl sulfate, at 60° C.

8. A nucleic acid probe comprising a glucocorticoid receptor encoding portion of DNA according to claim 6.

9. An isolated nucleic acid having the nucleotide sequence set forth in FIGS. 3(A) and 3(B).

10. Recombinant DNA encoding a glucocorticoid receptor having the amino acid sequence set forth in FIGS. 3(A) and 3(B).

11. The plasmid pRShGR-alpha (ATCC No. 67200).

12. Isolated mRNA complementary to DNA which hybridizes with DNA encoding glucocorticoid receptor having the amino acid sequence shown in FIGS. 3(A) and 3(B), or DNA complementary thereto, under nonstringent hybridization conditions comprising hybridization in 35% formamide, 5×SSPE, 1% Denhardt's reagent, 0.1% sodium dodecyl sulfate, 100 μg/mL salmon sperm DNA, at 42° C.; and washing with 2×SSC, 0.1% sodium dodecyl sulfate, at 55° C.

13. Cells transformed with DNA of claim 6.

14. Isolated mRNA complementary to DNA which hybridizes with DNA encoding glucocorticoid receptor having the amino acid sequence shown in FIGS. 3(A) and 3(B), or DNA complementary thereto, under stringent hybridization conditions comprising hybridization in 50% formamide, 5×SSPE, 1% Denhardt's reagent, 0.1% sodium dodecyl sulfite, 100 μg/mL salmon sperm DNA, at 42° C.; and washing with 0.1×SSC, 0.1% sodium dodecyl sulfate, at 60° C.

15. Isolated mRNA complementary to DNA encoding a glucocorticoid receptor having the amino acid sequence set forth in FIGS. 3(A) and 3(B) or DNA complementary thereto.

16. Isolated mRNA complementary to the nucleotide sequence of set forth in FIGS. 3(A) and 3(B).

* * * * *